US012195812B2

(12) United States Patent
Eaton et al.

(10) Patent No.: US 12,195,812 B2
(45) Date of Patent: Jan. 14, 2025

(54) **COMPOSITIONS AND METHODS FOR DETECTING *BORDETELLA PERTUSSIS* AND *BORDETELLA PARAPERTUSSIS* NUCLEIC ACID**

(71) Applicant: Gen-Probe Incorporated, San Diego, CA (US)

(72) Inventors: Barbara L. Eaton, San Diego, CA (US); Benjamin Grobarczyk, Saive (BE); Samira Barhdadi, Seraing (BE)

(73) Assignee: Gen-Probe Incorporated, San Diego, CA (US)

( * ) Notice: Subject to any disclaimer, the term of this patent is extended or adjusted under 35 U.S.C. 154(b) by 930 days.

(21) Appl. No.: 17/210,280

(22) Filed: Mar. 23, 2021

(65) Prior Publication Data

US 2021/0207195 A1 Jul. 8, 2021

Related U.S. Application Data

(63) Continuation of application No. PCT/US2019/053099, filed on Sep. 26, 2019.

(60) Provisional application No. 62/737,713, filed on Sep. 27, 2018.

(51) Int. Cl.
*C12Q 1/689* (2018.01)
*C12Q 1/6816* (2018.01)

(52) U.S. Cl.
CPC ........... *C12Q 1/689* (2013.01); *C12Q 1/6816* (2013.01)

(58) Field of Classification Search
None
See application file for complete search history.

(56) References Cited

U.S. PATENT DOCUMENTS

| | | | | |
|---|---|---|---|---|
| 8,507,201 | B2 | 8/2013 | Cockerill, III et al. | |
| 11,332,783 | B2 * | 5/2022 | Metsky | C12Q 1/686 |
| 2009/0197262 | A1 * | 8/2009 | Tabb | C12Q 1/689 536/23.7 |
| 2010/0330573 | A1 | 12/2010 | Larson et al. | |
| 2018/0030493 | A1 | 2/2018 | Hanamura et al. | |
| 2018/0030509 | A1 | 2/2018 | Hanamura et al. | |

FOREIGN PATENT DOCUMENTS

| | | | | |
|---|---|---|---|---|
| CN | 109988854 | A | 7/2019 | |
| WO | WO200261141 | * | 8/2002 | |
| WO | 2004070062 | A2 | 8/2004 | |
| WO | 2010124281 | A2 | 10/2010 | |
| WO | 2013049891 | A1 | 4/2013 | |
| WO | WO-2017165599 | A1 * | 9/2017 | A61K 31/407 |
| WO | 2018061877 | A1 | 4/2018 | |

OTHER PUBLICATIONS

Lanotte et al. Evaluation of four commercial real-time PCR assays for detection of *Bordetella* spp. in nasopharyngeal aspirates. J Clin Microbiol. Nov. 2011;49(11):3943-6. doi: 10.1128/JCM.00335-11. Epub Sep. 1, 20114. PMID: 21918018; PMCID: PMC3209097 (Year: 2011).*
Templeton et al. Evaluation of real-time PCR for detection of and discrimination between Bordetella pertussis, *Bordetella parapertussis*, and *Bordetella holmesii* for clinical diagnosis. J Clin Microbiol. Sep. 2003;41(9):4121-6. doi: 10.1128/JCM.41.9.4121-4126.2003 (Year: 2003).*
Ngoc Quang Minh (2014). Outpatient antibiotic use in acute respiratory infections in Ho Chi Minh City, Vietnam. PhD thesis The Open University (Year: 2014).*
Arbefeville et al. "Optimizing polymerase chain reaction testing for the diagnosis of pertussis: current perspectives," Pathology and Laboratory Medicine International, pp. 67-73 (2015).
English Translation of Chinese Patent No. CN109988854 A, dated Jul. 9, 2019, 29 pages.
English Translation of WO2018-061877 A1, dated Apr. 5, 2018 19 pages.
Lanotte et al., "Evaluation of Four Commercial Real-Time PCR Assays for Detection of *Bordetella* spp. in Nasopharyngeal Aspirates," Journal of Clinical Microbiology, 49(11): 3943-3946 (2011).
Loeffelholz "Towards Improved Accuracy of *Bordetella pertussis* Nucleic Acid Amplification Tests," Journal of Clinical Microbiology, 50(7): 2186-2190 (2012).
PCT, International Search Report and Written Opinion for PCT/US2019/053099, dated Aug. 31, 2020 (20 pages).
Pittet et al. "Diagnosis of Whooping Cough in Switzerland: Differentiating *Bordetella pertussis* from *Bordetella holmesii* by Polymerase Chain Reaction," PLOS One, 9(2): e88936 (2014).
Templeton et al. "Evaluation of Real-Time PCR for Detection of and Discrimination between *Bordetella pertussis*, *Bordetella parapertussis*, and *Bordetella holmesii* for Clinical Diagnosis," Journal of Clinical Microbiology, 41(9): 4121-4126 (2003).

* cited by examiner

*Primary Examiner* — Aaron A Priest
*Assistant Examiner* — Tian N Yu
(74) *Attorney, Agent, or Firm* — Christensen O'Connor Johnson Kindness PLLC; Jeffrey E. Landes

(57) ABSTRACT

Disclosed are nucleic acid oligomers, including amplification oligomers and detection probes, for detection of *Bordetella pertussis* and *Bordetella parapertussis* nucleic acid. Also disclosed are methods of specific nucleic acid amplification and detection using the disclosed oligomers, as well as corresponding reaction mixtures and kits.

20 Claims, No Drawings

Specification includes a Sequence Listing.

SEQUENCE LISTING

<160> NUMBER OF SEQ ID NOS: 46

<210> SEQ ID NO 1
<211> LENGTH: 3791
<212> TYPE: DNA
<213> ORGANISM: Bordetella pertussis
<300> PUBLICATION INFORMATION:
<308> DATABASE ACCESSION NUMBER: AB670737.1
<309> DATABASE ENTRY DATE: 2012-03-06
<313> RELEVANT RESIDUES IN SEQ ID NO: (1)..(3791)

<400> SEQUENCE: 1
atgaacatgt ctctgtcacg cattgtcaag gcggcgcccc tgcgccgcac cacgctggcc 60
atggcgctgg gcgcgctggg cgccgccccg gcggcgcatg ccgactggaa caaccagtcc 120
atcgtcaaga ccggtgagcg ccagcatggc atccatatcc agggctccga cccgggcggc 180
gtacggaccg ccagcggaac caccatcaag gtaagcggcc gtcaggccca gggcatcctg 240
ctagaaaatc ccgcggccga gctgcagttc cggaacggca gtgtcacgtc gtcgggacag 300
ttgtccgacg atggcatccg gcgctttctg ggcaccgtca ccgtcaaggc cggcaagctg 360
gtcgccgatc acgccacgct ggccaacgtt ggcgacacct gggacgacga cggcatcgcg 420
ctctatgtgg ccggcgaaca ggcccaggcc agcatcgccg acagcaccct gcagggcgct 480
ggcggcgtgc agatcgagcg cggcgccaat gtcacggtcc aacgcagcgc catcgtcgac 540
gggggcttgc atatcggcgc cctgcagtca ttgcagccgg aagaccttcc gcccagccgg 600
gtggtgctgc gcgacaccaa cgtgaccgcc gtgcccgcca gcggcgcgcc cgcggcggtg 660
tctgtgttgg gggccagtga gcttacgctc gacggcgggc acatcaccgg cgggcgggca 720
gcgggggtgg cggccatgca aggggcggtc gtgcatctgc agcgcgcgac gatacggcgc 780
ggggacgcgc ctgccggcgg tgcggttccc ggcggtgcgg ttcccggtgg tgcggttccc 840
ggcggcttcg gtcccggcgg cttcggtccc gtcctcgacg gctggtatgg cgtggacgta 900
tcgggctcca gcgtggagct cgcccagtcg atcgtcgagg cgccggagct gggcgccgca 960
atccgggtgg gccgcggcgc cagggtgacg gtgtcgggcg gcagcttgtc cgcaccgcac 1020
ggcaatgtca tcgagaccgg cggcgcgcgt cgctttgcgc ctcaagccgc gcccctgtcg 1080
atcaccttgc aggccggcgc gcatgcccag gggaaagcgc tgctgtaccg ggtcctgccg 1140
gagcccgtga agctgacgct gaccgggggc gccgatgcgc agggcgacat cgtcgcgacg 1200
gagctgccct ccattcccgg cacgtcgatc gggccgctcg acgtggcgct ggccagccag 1260
gcccgatgga cgggcgctac ccgcgcggtc gactcgctgt ccatcgacaa cgccacctgg 1320

-continued

```
gtcatgacgg acaactcgaa cgtcggtgcg ctacggctgg ccagcgacgg cagcgtcgat   1380
ttccagcagc cggccgaagc tgggcggttc aaggtcctga cggtcaatac gctggcgggt   1440
tcggggctgt tccgcatgaa tgtcttcgcg gacctggggc tgagcgacaa gctggtcgtc   1500
atgcaggacg ccagcggcca gcacaggctg tgggtccgca acagcggcag cgagccggcc   1560
agcgccaaca ccctgctgct ggtgcagacg ccactaggtg tgaagattca ataggttgta   1620
tgcatggttc atccgaaccg gatttgagaa actggaaatc gccaaccccc cagttcactc   1680
aaggagcccg gccggatgaa cacccataag catgcccgat tgaccttcct acgtcgactc   1740
gaaatggtcc agcaattgat cgcccatcaa gtttgtgtgc ctgaagcggc ccgcgcctat   1800
ggggtcaccg cgccgactgt gcgcaaatgg ctgggccgct tcctggctca gggccaggcg   1860
ggcttggccg atgcgtcctc gcgcccgacg gtctcgcccc gagcgattgc gccggccaag   1920
gcgctggcta tcgtggagct gcgccgcaag cggctgaccc aagcgcgcat cgcccaggcg   1980
ctgggcgtgt cagccagcac cgtcagccgc gtcctggccc gcgccggtct gtcgcacctg   2040
gccgacctgg agccggccga gccggtggtg cgctacgagc atcaggcccc cggcgatctg   2100
ctgcacatcg acatcaagaa gctgggacgt atccagcgcc ctggtcaccg ggtcacgggc   2160
aaccgacgcg ataccgttga gggggccggc tgggacttcg tcttcgtggc catcgatgac   2220
cacgcccgcg tggccttcac cgacatccac cccgacgagc gcttccccag cgccgtccag   2280
ttcctcaagg acgcagtggc ctactaccag cgcctgggcg tgaccatcca gcgcttgctc   2340
accgacaatg gctcggcctt tcgcagccgc gccttcgccg cgctgtgcca tgagctgggc   2400
atcaagcacc gctttacccg accttaccgc ccacagacca atggcaaggc cgaacgcttc   2460
atccagtcgg ccttgcgtga gtgggcttac gctcacacct accagaactc ccaacaccga   2520
gccgatgcca tgaaatcctg gctacaccac tacaactggc atcgacccca ccaaggcatc   2580
gggcgcgctg tacccatctc cagactcaac ctggacgaat acaacctatt gacagttcac   2640
aactaggcag cgcggcgacc tttacccttg ccaacaagga cggcaaggtc gatatcggta   2700
cctatcgcta tcgattggcc gccaacggca atgggcagtg gagcctggtg ggcgcgaagg   2760
cgccgccggc gcccaagccc gcgccgcagc cgggtcccca gccgccgcag ccgccgcagc   2820
cgcagccgga agcgccggcg ccgcaaccgc cggcgggcag ggagttgtcc gccgccgcca   2880
acgcggcggt caacacgggt ggggtgggcc tggccagcac gctctggtac gccgaaagca   2940
atgcgttgtc caagcgcctg ggcgagttgc gcctgaatcc ggacgccggc ggcgcctggg   3000
gccgcggctt cgcgcaacgc cagcagctgg acaaccgcgc cgggcggcgc ttcgaccaga   3060
aggtggccgg cttcgagctg ggcgccgacc acgcggtggc ggtggccggc ggacgctggc   3120
acctgggcgg gctggccggc tatacgcgcg gcgaccgcgg cttcaccggc gacggcggcg   3180
gccacaccga cagcgtgcat gtcgggggct atgccacata tatcgccgac agcggtttct   3240
acctggacgc gacgctgcgc gccagccgcc tggagaatga cttcaaggtg gcgggcagcg   3300
acgggtacgc ggtcaagggc aagtaccgca cccatggggt gggcgcctcg ctcgaggcgg   3360
gccggcgctt tacccatgcc gacggctggt tcctcgagcc gcaggccgag ctggcggtat   3420
tccgggccgg cggcggtgcg taccgcgcgg ccaacggcct gcgggtgcgc gacgaaggcg   3480
gcagctcggt gctgggtcgc ctgggcctgg aggtcggcaa gcgcatcgaa ctggcaggcg   3540
gcaggcaggt gcagccatac atcaaggcca gcgtgctgca ggagttcgac ggcgcgggta   3600
cggtacacac caacggcatc gcgcaccgca ccgaactgcg cggcacgcgc gccgaactgg   3660
```

gcctgggcat ggccgccgcg ctgggccgcg gccacagcct gtatgcctcg tacgagtact 3720
ccaagggccc gaagctggcc atgccgtgga ccttccacgc gggctaccgg tacagctggt 3780
aaagcgagga g 3791

<210> SEQ ID NO 2
<211> LENGTH: 1190
<212> TYPE: DNA
<213> ORGANISM: Bordetella parapertussis
<300> PUBLICATION INFORMATION:
<308> DATABASE ACCESSION NUMBER: JX013522.1
<309> DATABASE ENTRY DATE: 2012-10-01
<313> RELEVANT RESIDUES IN SEQ ID NO: (1)..(1190)

<400> SEQUENCE: 2
gctggatcgc aagttgctgg agtcgctggg aggctggcag ggctatggcg tcgaacgcgt 60
ggaatggccc gaagacccag ggcgcacgct gtcgatctat ttgaagccaa cggccaaggt 120
gatgctgtgc gagcagtgcg gcgcgcggtg tcgccaggtg catgagacca cggttcgacg 180
ggtgcgagat ctgccgttat tcgagtatcg ggtcgttctg cacgtgccgc gccgacgctt 240
gtggtgtgag caatgcggcg gcccgcgcct ggagcggctt gcctggctgg ggcgatatca 300
acgggtgacg gatcggctgg cgcaggcctg cagccaattg ctgcaatcga gcaacgtgca 360
ggcggtggcg aggttcttcg agctgggttg gcataccgtc aagacgctgg acaaggctcg 420
gctgcgtgcg tcggtgcgcg aaccggattg gtccaagatc gagtatttgg cgatggacga 480
gtttgccctg cacaaagggc atcgctacgc gacagtggtg gtcgatccga tcggcaggca 540
ggtgctgtgg attggcccag gacgctcacg cgagacggcc cgggcgttct tcgaacaatt 600
gccgcctggg gccgcccaac gcatcaaggc cgttgccatc gacatgacca ccgcctacga 660
gttggagatc caggcccaca gcccacaggc ggagatcgtc tatgacttgt tccatgtcgt 720
ggccaagtat ggacgagagg tcattgatcg ggtgcgcgtg gatcaggcca atcaactacg 780
ccaggatcgt cccgcacgca ggatcatcaa atcgagtcgc tggctgctgc tgcgcaaccg 840
tgacaacctg gatcggcagc aggccgtccg gctcgacgaa ttgctgcaag ccaaccagcc 900
gctgctgacg gtctatgtcc tgcgtgacga actcaaacgg ctctggttct accaaagacc 960
tgcctgggca agacaagcct ggaaccactg gtacgagcag gccgagcaaa gcggaatagc 1020
cgccttgaac accttcgctc agcgcttgaa aggctatctg cacggcatcc tggccagatg 1080
ccgacatccc ctgaacacca gcattgtcga gggcatcaac aacactatca aggtcatcaa 1140
gcggcgcgct tacggctacc gcgaccagga atacttcttc ctcaaaatcc 1190

<210> SEQ ID NO 3
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 3
ttgcgtgagt gggctta 17

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
aacaccgagc cgatgccatg 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
atgccagttg tagtggtgta 20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
ccttgcgtga gtgggcttac 20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
cccaacaccg agccgatgcc 20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
gtggggtcga tgccagttgt 20

<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 9
ttacgctcac acctacca 18

<210> SEQ ID NO 10
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 10
tacaccacta caactggcat cgac 24

<210> SEQ ID NO 11
<211> LENGTH: 19
<212> TYPE: DNA

-continued

<213> ORGANISM: Artificial Sequence
<220> FEATURE:
<223> OTHER INFORMATION: Synthetic Oligonucleotide

<400> SEQUENCE: 11
agtctggaga tgggtacag 19

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 12
ccgatgccat gaaatcct 18

<210> SEQ ID NO 13
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 13
tacaccacta caactggcat cgac 24

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
gtattcgtcc aggttgagtc 20

<210> SEQ ID NO 15
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 15
cacatatatc gccgacagc 19

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
tttctacctg gacgcgacgc 20

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
cgccaccttg aagtcatt 18

-continued

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
ccgaaccgga tttgagaaac 20

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 19
ccggccggat gaacacccat aa 22

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
taggaaggtc aatcgggcat 20

<210> SEQ ID NO 21
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 21
gattcaatag gttgtatgca tggtt 25

<210> SEQ ID NO 22
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 22
tcgccaaccc cccagttcac tca 23

<210> SEQ ID NO 23
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 23
ttcaggcaca caaacttgat gggcg 25

<210> SEQ ID NO 24
<211> LENGTH: 24
<212> TYPE: DNA
<213> ORGANISM: Artificial Sequence
<220> FEATURE:

<223> OTHER INFORMATION: Synthetic Oligonucleotide

<400> SEQUENCE: 24
atcgggcatg cttatgggtg ttca 24

<210> SEQ ID NO 25
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 25
cttgagtgaa ctggggggtc ggcgatttcc agtt 34

<210> SEQ ID NO 26
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 26
gcgggctaac tgtgaagatt caatag 26

<210> SEQ ID NO 27
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 27
gattcaatag gttgtatgca tgg 23

<210> SEQ ID NO 28
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 28
ataagcatgc ccgattgacc ttcc 24

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 29
ttcaggcaca caaacttgat gg 22

<210> SEQ ID NO 30
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 30
gagatcgtct atgacttgtt cc 22

<210> SEQ ID NO 31
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 31
aatgacctct cgtccatact tggc 24

<210> SEQ ID NO 32
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 32
acgatcctgg cgtagtt 17

<210> SEQ ID NO 33
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 33
ttcgagtatc gggtcgtt 18

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 34
cttgtggtgt gagcaatgcg g 21

<210> SEQ ID NO 35
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 35
atccgtcacc cgttgata 18

<210> SEQ ID NO 36
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 36
caccgcctac gagttcgaga t 21

<210> SEQ ID NO 37
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 37
gttctaccaa agacctgcct gggc 24

<210> SEQ ID NO 38
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 38
cctcgacaat gctggtgttc a 21

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
ccatgtcgtg gccaagtatg 20

<210> SEQ ID NO 40
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 40
acgcaggatc atcaaatcga gtcg 24

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
gctggttggc ttgcagcaat 20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
tcaagacgct ggacaaggct 20

<210> SEQ ID NO 43
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 43
cggctgcgtg cgtcggtg 18

<210> SEQ ID NO 44
<211> LENGTH: 20

-continued

```
<212> TYPE: DNA
<213> ORGANISM: Artificial Sequence
<220> FEATURE:
<223> OTHER INFORMATION: Synthetic Oligonucleotide

<400> SEQUENCE: 44

gcagggcaaa ctcgtccatc                                              20


<210> SEQ ID NO 45
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 45

cttacgctca cacctacca                                               19


<210> SEQ ID NO 46
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 46

cgatgccagt tgtagtggt                                               19
```

COMPOSITIONS AND METHODS FOR DETECTING *BORDETELLA PERTUSSIS* AND *BORDETELLA PARAPERTUSSIS* NUCLEIC ACID

CROSS-REFERENCE TO RELATED APPLICATIONS

This application is a continuation of International application No. PCT/US2019/053099, filed Sep. 26, 2019, which claims the benefit of priority of U.S. Provisional Patent Application No. 62/737,713, filed Sep. 27, 2018, which is incorporated by reference herein in its entirety for all purposes.

SEQUENCE LISTING

The present application is filed with a Sequence Listing in electronic format. The Sequence Listing is provided as a file entitled "2019-09-24_01159-0040-00PCT_Seq_List_PATENTIN_ST25" created on Sep. 24, 2019, which is 15,862 bytes in size. The information in the electronic format of the sequence listing is incorporated herein by reference in its entirety.

BACKGROUND

The genus *Bordetella* contains eight species, of which four are known to cause more or less severe respiratory diseases in humans: *Bordetella bronchiseptica, holmesii, parapertussis*, and pertussis. *Bordetella holmesii* is less virulent than the other three species (CDC guidance, report 2012; WHO, report 2014). *Bordetella pertussis* is described as a strictly human pathogen whereas *Bordetella parapertussis* is found in sheep and humans. *Bordetella bronchiseptica* can cause respiratory infections in many animal species and, infrequently, in humans. An increasing number of pertussis-like cases are attributed to the emerging pathogen *Bordetella holmesii*, but it is still unclear whether this species is truly pathogenic to humans (Von Konig et al., 2011; Pittet et al., 2014).

Several commercial kits based on nucleic acids detection are available for *Bordetella pertussis* and *parapertussis* detection in clinical specimens (review in Arbefeville S. & Ferrieri P., Optimizing polymerase chain reaction testing for the diagnosis of pertussis; current perspectives, *Pathology and Laboratory Medicine International,* 2015; Lanotte P. et al., Evaluation of Four of Four Commercial Real-Time PCR Assays for Detection of *Bordetella* spp. in Nasopharyngeal Aspirates, *Journal of Clinical Microbiology,* 2011). These kits include RT-PCR assays such as the Simplexa *Bordetella* assay (Focus Diagnostics), the SmartCycler *Bordetella pertussis/parapertussis* assay (Cepheid), and the *Bordetella* R-gene assay (Argene).

SUMMARY

The present invention provides the following embodiments, including compositions and methods for determining the presence or absence of each of *Bordetella pertussis* (Bp) and *Bordetella parapertussis* (Bpp) in a sample.

Embodiment 1 is a composition for determining the presence or absence of each of *Bordetella pertussis* (Bp) and *Bordetella parapertussis* (Bpp) in a sample, said composition comprising:

a first amplification oligomer combination and a second amplification oligomer combination, wherein (I) the first amplification oligomer combination comprises first and second Bp-specific amplification oligomers capable of amplifying a target region of a Bp target nucleic acid, wherein the first and second Bp-specific amplification oligomers comprise, respectively, first (A) and second (B) Bp-specific target-hybridizing sequences selected from the group consisting of (a) (A) SEQ ID NO:3, SEQ ID NO:6, SEQ ID NO:9, SEQ ID NO:12, or SEQ ID NO: 45, or an RNA equivalent or DNA/RNA chimeric thereof, and (B) SEQ ID NO:5, SEQ ID NO:8, SEQ ID NO:11, SEQ ID NO:14, or SEQ ID NO:46, or an RNA equivalent or DNA/RNA chimeric thereof; and (b) (A) SEQ ID NO:18, SEQ ID NO:21, or SEQ ID NO:27, or an RNA equivalent or DNA/RNA chimeric thereof, and (B) SEQ ID NO:20, SEQ ID NO:23, or SEQ ID NO:29, or an RNA equivalent or DNA/RNA chimeric thereof; and (II) the second amplification oligomer combination comprises first and second Bpp-specific amplification oligomers capable of amplifying a target region of a Bpp target nucleic acid, wherein the first and second Bpp-specific amplification oligomers comprise, respectively, first (A') and second (B') Bpp-specific target-hybridizing sequences selected from the group consisting of (a) (A') SEQ ID NO:30, SEQ ID NO:36, or SEQ ID NO:39, or an RNA equivalent or DNA/RNA chimeric thereof, and (B') SEQ ID NO:32, SEQ ID NO:38, or SEQ ID NO:41, or an RNA equivalent or DNA/RNA chimeric thereof;

(b) (A') SEQ ID NO:33, or an RNA equivalent or DNA/RNA chimeric thereof, and (B') SEQ ID NO:35, or an RNA equivalent or DNA/RNA chimeric thereof; and (c) (A') SEQ ID NO:42, or an RNA equivalent or DNA/RNA chimeric thereof, and (B') SEQ ID NO:44, or an RNA equivalent or DNA/RNA chimeric thereof.

Embodiment 2 is the composition of embodiment 1, further comprising a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 3 is the composition of embodiment 1, wherein the first (A) and second (B) Bp specific target-hybridizing sequences are selected from the group consisting of (A) SEQ ID NO:3, or an RNA equivalent or DNA/RNA chimeric thereof, and (B) SEQ ID NO: 5, or an RNA equivalent or DNA/RNA chimeric thereof;

(A) SEQ ID NO:6, or an RNA equivalent or DNA/RNA chimeric thereof, and (B) SEQ ID NO: 8, or an RNA equivalent or DNA/RNA chimeric thereof;

(A) SEQ ID NO:9, or an RNA equivalent or DNA/RNA chimeric thereof, and (B) SEQ ID NO: 11, or an RNA equivalent or DNA/RNA chimeric thereof;

(A) SEQ ID NO:12, or an RNA equivalent or DNA/RNA chimeric thereof, and (B) SEQ ID NO:14, or an RNA equivalent or DNA/RNA chimeric thereof;

(A) SEQ ID NO:18, or an RNA equivalent or DNA/RNA chimeric thereof, and (B) SEQ ID NO:20, or an RNA equivalent or DNA/RNA chimeric thereof;

(A) SEQ ID NO:21, or an RNA equivalent or DNA/RNA chimeric thereof, and (B) SEQ ID NO:23, or an RNA equivalent or DNA/RNA chimeric thereof; and (A) SEQ ID NO:27, or an RNA equivalent or DNA/RNA chimeric thereof, and (B) SEQ ID NO:29, or an RNA equivalent or DNA/RNA chimeric thereof.

Embodiment 4 is the composition of embodiment 3, further comprising a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 5 is the composition of embodiment 4, wherein a. the first and second Bp-specific target-hybridizing sequences are the target-hybridizing sequences of (i) and the Bp-specific detection probe target-hybridizing sequence is SEQ ID NO:4, or an RNA equivalent or DNA/RNA chimeric thereof;

b. the first and second Bp-specific target-hybridizing sequences are the target-hybridizing sequences of (ii) and the Bp-specific detection probe target-hybridizing sequence is SEQ ID NO:7, or an RNA equivalent or DNA/RNA chimeric thereof;

c. the first and second Bp-specific target-hybridizing sequences are the target-hybridizing sequences of (iii) and the Bp-specific detection probe target-hybridizing sequence is SEQ ID NO: 10, or an RNA equivalent or DNA/RNA chimeric thereof;

d. the first and second Bp-specific target-hybridizing sequences are the target-hybridizing sequences of (iv) and the Bp-specific detection probe target-hybridizing sequence is SEQ ID NO: 13, or an RNA equivalent or DNA/RNA chimeric thereof;

e. the first and second Bp-specific target-hybridizing sequences are the target-hybridizing sequences of (v) and the Bp-specific detection probe target-hybridizing sequence is SEQ ID NO: 16, or an RNA equivalent or DNA/RNA chimeric thereof;

f. the first and second Bp-specific target-hybridizing sequences are the target-hybridizing sequences of (vi) and the Bp-specific detection probe target-hybridizing sequence is SEQ ID NO: 19, or an RNA equivalent or DNA/RNA chimeric thereof;

g. the first and second Bp-specific target-hybridizing sequences are the target-hybridizing sequences of (vii) and the Bp-specific detection probe target-hybridizing sequence is SEQ ID NO:22, or an RNA equivalent or DNA/RNA chimeric thereof; or h. the first and second Bp-specific target-hybridizing sequences are the target-hybridizing sequences of (viii) and the Bp-specific detection probe target-hybridizing sequence is SEQ ID NO:28, or an RNA equivalent or DNA/RNA chimeric thereof.

Embodiment 6 is the composition of any one of embodiments 2, 4, and 5, wherein the Bp-specific detection probe oligomer further comprises a detectable label.

Embodiment 7 is the composition of embodiment 6, wherein the detectable label is a fluorescent or chemiluminescent label.

Embodiment 8 is the composition of embodiment 6, wherein the detectable label is a fluorescent label and the Bp-specific detection probe oligomer further comprises a non-fluorescent quencher.

Embodiment 9 is the composition of any one of embodiments 1 to 9, further comprising a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 10 is the composition of any one of embodiments 1-9, wherein the first (A') and second (B') Bpp-specific target-hybridizing sequences are selected from the group consisting of (i') (A') SEQ ID NO:30, or an RNA equivalent or DNA/RNA chimeric thereof, and (B') SEQ ID NO:32, or an RNA equivalent or DNA/RNA chimeric thereof;

(ii') (A') SEQ ID NO:33, or an RNA equivalent or DNA/RNA chimeric thereof, and (B') SEQ ID NO:35, or an RNA equivalent or DNA/RNA chimeric thereof;

(iii') (A') SEQ ID NO:36, or an RNA equivalent or DNA/RNA chimeric thereof, and (B') SEQ ID NO:38, or an RNA equivalent or DNA/RNA chimeric thereof;

(iv') (A') SEQ ID NO:39, or an RNA equivalent or DNA/RNA chimeric thereof, and (B') SEQ ID NO:41, or an RNA equivalent or DNA/RNA chimeric thereof; and (v') (A') SEQ ID NO:42, or an RNA equivalent or DNA/RNA chimeric thereof, and (B') SEQ ID NO:44, or an RNA equivalent or DNA/RNA chimeric thereof.

Embodiment 11 is the composition of embodiment 10, further comprising a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 12 is the composition of embodiment 11, wherein the first and second Bpp-specific target-hybridizing sequences are the target-hybridizing sequences of (i') and the Bpp-specific detection probe target-hybridizing sequence is SEQ ID NO: 31, or an RNA equivalent or DNA/RNA chimeric thereof;

the first and second Bpp-specific target-hybridizing sequences are the target-hybridizing sequences of (ii') and the Bpp-specific detection probe target-hybridizing sequence is SEQ ID NO: 34, or an RNA equivalent or DNA/RNA chimeric thereof;

the first and second Bpp-specific target-hybridizing sequences are the target-hybridizing sequences of (iii') and the Bpp-specific detection probe target-hybridizing sequence is SEQ ID NO: 37, or an RNA equivalent or DNA/RNA chimeric thereof;

the first and second Bpp-specific target-hybridizing sequences are the target-hybridizing sequences of (iv') and the Bpp-specific detection probe target-hybridizing sequence is SEQ ID NO: 40, or an RNA equivalent or DNA/RNA chimeric thereof; or the first and second Bpp-specific target-hybridizing sequences are the target-hybridizing sequences of (v') and the Bpp-specific detection probe target-hybridizing sequence is SEQ ID NO: 43, or an RNA equivalent or DNA/RNA chimeric thereof.

Embodiment 13 is the composition of any one of embodiments 9, 11, and 12, wherein the Bpp-specific detection probe oligomer further comprises a detectable label.

Embodiment 14 is the composition of embodiment 13, wherein the detectable label is a fluorescent or chemiluminescent label.

Embodiment 15 is the composition of embodiment 13, wherein the detectable label is a fluorescent label and the detection probe oligomer further comprises a non-fluorescent quencher.

Embodiment 16 is a composition for determining the presence or absence of *Bordetella pertussis* (Bp) in a sample, said composition comprising:

an amplification oligomer combination comprising first and second Bp-specific amplification oligomers capable of amplifying a target region of a Bp target nucleic acid, wherein the first and second Bp-specific amplification oligomers comprise, respectively, first (A) and second (B) Bp-specific target-hybridizing sequences selected from the group consisting of (a) (A) SEQ ID NO:3, SEQ ID NO:6, SEQ ID NO:9, SEQ ID NO:12, or SEQ ID NO: 45, or an RNA equivalent or DNA/RNA chimeric thereof, and (B) SEQ ID NO:5, SEQ ID NO:8, SEQ ID NO:11, SEQ ID NO:14, or SEQ ID NO:46, or an RNA equivalent or DNA/RNA chimeric thereof; and (b) (A) SEQ ID NO:18, SEQ ID NO:21, or SEQ ID NO:27, or an RNA equivalent or DNA/RNA chimeric thereof, and (B) SEQ ID NO:20, SEQ ID NO:23, or SEQ ID NO:29, or an RNA equivalent or DNA/RNA chimeric thereof.

Embodiment 17 is the composition of embodiment 16, further comprising a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 18 is the composition of embodiment 16, wherein the first (A) and second (B) Bp specific target-hybridizing sequences are selected from the group consisting of (i) (A) SEQ ID NO:3, or an RNA equivalent or DNA/RNA chimeric thereof, and (B) SEQ ID NO:5, or an RNA equivalent or DNA/RNA chimeric thereof;

(ii) (A) SEQ ID NO:6, or an RNA equivalent or DNA/RNA chimeric thereof, and (B) SEQ ID NO:8, or an RNA equivalent or DNA/RNA chimeric thereof;

(iii) (A) SEQ ID NO:9, or an RNA equivalent or DNA/RNA chimeric thereof, and (B) SEQ ID NO:11, or an RNA equivalent or DNA/RNA chimeric thereof;

(iv) (A) SEQ ID NO:12, or an RNA equivalent or DNA/RNA chimeric thereof, and (B) SEQ ID NO:14, or an RNA equivalent or DNA/RNA chimeric thereof;

(v) (A) SEQ ID NO:18, or an RNA equivalent or DNA/RNA chimeric thereof, and (B) SEQ ID NO:20, or an RNA equivalent or DNA/RNA chimeric thereof;

(vi) (A) SEQ ID NO:21, or an RNA equivalent or DNA/RNA chimeric thereof, and (B) SEQ ID NO:23, or an RNA equivalent or DNA/RNA chimeric thereof; and (A) SEQ ID NO:27, or an RNA equivalent or DNA/RNA chimeric thereof, and (B) SEQ ID NO:29, or an RNA equivalent or DNA/RNA chimeric thereof.

Embodiment 19 is the composition of embodiment 18, further comprising a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 20 is the composition of embodiment 19, wherein the first and second Bp-specific target-hybridizing sequences are the target-hybridizing sequences of (i) and the Bp-specific detection probe target-hybridizing sequence is SEQ ID NO: 4, or an RNA equivalent or DNA/RNA chimeric thereof;

the first and second Bp-specific target-hybridizing sequences are the target-hybridizing sequences of (ii) and the Bp-specific detection probe target-hybridizing sequence is SEQ ID NO: 7, or an RNA equivalent or DNA/RNA chimeric thereof;

the first and second Bp-specific target-hybridizing sequences are the target-hybridizing sequences of (iii) and the Bp-specific detection probe target-hybridizing sequence is SEQ ID NO: 10, or an RNA equivalent or DNA/RNA chimeric thereof;

the first and second Bp-specific target-hybridizing sequences are the target-hybridizing sequences of (iv) and the Bp-specific detection probe target-hybridizing sequence is SEQ ID NO: 13, or an RNA equivalent or DNA/RNA chimeric thereof;

the first and second Bp-specific target-hybridizing sequences are the target-hybridizing sequences of (v) and the Bp-specific detection probe target-hybridizing sequence is SEQ ID NO: 16, or an RNA equivalent or DNA/RNA chimeric thereof;

the first and second Bp-specific target-hybridizing sequences are the target-hybridizing sequences of (vi) and the Bp-specific detection probe target-hybridizing sequence is SEQ ID NO: 19, or an RNA equivalent or DNA/RNA chimeric thereof;

the first and second Bp-specific target-hybridizing sequences are the target-hybridizing sequences of (vii) and the Bp-specific detection probe target-hybridizing sequence is SEQ ID NO: 22, or an RNA equivalent or DNA/RNA chimeric thereof; or the first and second Bp-specific target-hybridizing sequences are the target-hybridizing sequences of (viii) and the Bp-specific detection probe target-hybridizing sequence is SEQ ID NO: 28, or an RNA equivalent or DNA/RNA chimeric thereof.

Embodiment 21 is the composition of any one of embodiments 17, 19, and 20, wherein the Bp-specific detection probe oligomer further comprises a detectable label.

Embodiment 22 is the composition of embodiment 21, wherein the detectable label is a fluorescent or chemiluminescent label.

Embodiment 23 is the composition of embodiment 21, wherein the detectable label is a fluorescent label and the Bp-specific detection probe oligomer further comprises a non-fluorescent quencher.

Embodiment 24 is the composition of any one of embodiments 16 to 23, further comprising a second amplification oligomer combination capable of amplifying a target region of a *Bordetella parapertussis* (Bpp) target nucleic acid.

Embodiment 25 is a composition for determining the presence or absence of *Bordetella parapertussis* (Bpp) in a sample, said composition comprising:

an amplification oligomer combination comprising first and second Bpp-specific amplification oligomers capable of amplifying a target region of a Bpp target nucleic acid, wherein the first and second Bpp-specific amplification oligomers comprise, respectively, first (A') and second (B') Bpp-specific target-hybridizing sequences selected from the group consisting of (a) (A') SEQ ID NO:30, SEQ ID NO:36, or SEQ ID NO:39, or an RNA equivalent or DNA/RNA chimeric thereof, and (B') SEQ ID NO:32, SEQ ID NO:38, or SEQ ID NO:41, or an RNA equivalent or DNA/RNA chimeric thereof;

(b) (A') SEQ ID NO:33, or an RNA equivalent or DNA/RNA chimeric thereof, and (B') SEQ ID NO:35, or an RNA equivalent or DNA/RNA chimeric thereof; and (c) (A') SEQ ID NO:42, or an RNA equivalent or DNA/RNA chimeric thereof, and (B') SEQ ID NO:44, or an RNA equivalent or DNA/RNA chimeric thereof.

Embodiment 26 is the composition of embodiment 25, further comprising a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 27 is the composition of embodiment 25, wherein the first (A') and second (B') Bpp-specific target-hybridizing sequences are selected from the group consisting of (i') (A') SEQ ID NO:30, or an RNA equivalent or DNA/RNA chimeric thereof, and (B') SEQ ID NO:32, or an RNA equivalent or DNA/RNA chimeric thereof;

(ii') (A') SEQ ID NO:33, or an RNA equivalent or DNA/RNA chimeric thereof, and (B') SEQ ID NO:35, or an RNA equivalent or DNA/RNA chimeric thereof;

(iii') (A') SEQ ID NO:36, or an RNA equivalent or DNA/RNA chimeric thereof, and (B') SEQ ID NO:38, or an RNA equivalent or DNA/RNA chimeric thereof;

(iv') (A') SEQ ID NO:39, or an RNA equivalent or DNA/RNA chimeric thereof, and (B') SEQ ID NO:41, or an RNA equivalent or DNA/RNA chimeric thereof; and (v") (A') SEQ ID NO:42, or an RNA equivalent or DNA/RNA chimeric thereof, and (B') SEQ ID NO:44, or an RNA equivalent or DNA/RNA chimeric thereof.

Embodiment 28 is the composition of embodiment 27, further comprising a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 29 is the composition of embodiment 28, wherein the first and second Bpp-specific target-hybridizing sequences are the target-hybridizing sequences of (i') and the Bpp-specific detection probe target-hybridizing sequence is SEQ ID NO: 31, or an RNA equivalent or DNA/RNA chimeric thereof;

the first and second Bpp-specific target-hybridizing sequences are the target-hybridizing sequences of (ii') and the Bpp-specific detection probe target-hybridizing sequence is SEQ ID NO: 34, or an RNA equivalent or DNA/RNA chimeric thereof;

the first and second Bpp-specific target-hybridizing sequences are the target-hybridizing sequences of (iii') and the Bpp-specific detection probe target-hybridizing sequence is SEQ ID NO: 37, or an RNA equivalent or DNA/RNA chimeric thereof;

the first and second Bpp-specific target-hybridizing sequences are the target-hybridizing sequences of (iv') and the Bpp-specific detection probe target-hybridizing sequence is SEQ ID NO: 40, or an RNA equivalent or DNA/RNA chimeric thereof; or the first and second Bpp-specific target-hybridizing sequences are the target-hybridizing sequences of (v') and the Bpp-specific detection probe target-hybridizing sequence is SEQ ID NO: 43, or an RNA equivalent or DNA/RNA chimeric thereof.

Embodiment 30 is the composition of any one of embodiments 26, 28, and 29, wherein the Bpp-specific detection probe oligomer further comprises a detectable label.

Embodiment 31 is the composition of embodiment 30, wherein the detectable label is a fluorescent or chemiluminescent label.

Embodiment 32 is the composition of embodiment 30, wherein the detectable label is a fluorescent label and the detection probe oligomer further comprises a non-fluorescent quencher.

Embodiment 33 is the composition of any one of embodiments 25 to 32, further comprising a second amplification oligomer combination capable of amplifying a target region of a *Bordetella pertussis* (Bp) target nucleic acid.

Embodiment 34 is a kit for determining the presence or absence of each of *Bordetella pertussis* (Bp) and *Bordetella parapertussis* (Bpp) in a sample, said kit comprising: a first amplification oligomer combination and a second amplification oligomer combination, wherein (I) the first amplification oligomer combination comprises first and second Bp-specific amplification oligomers capable of amplifying a target region of a Bp target nucleic acid, wherein the first and second Bp-specific amplification oligomers comprise, respectively, first (A) and second (B) Bp-specific target-hybridizing sequences selected from the group consisting of (a) (A) SEQ ID NO:3, SEQ ID NO:6, SEQ ID NO:9, SEQ ID NO:12, or SEQ ID NO: 45, or an RNA equivalent or DNA/RNA chimeric thereof, and (B) SEQ ID NO:5, SEQ ID NO:8, SEQ ID NO:11, SEQ ID NO:14, or SEQ ID NO:46, or an RNA equivalent or DNA/RNA chimeric thereof; and (b) (A) SEQ ID NO:18, SEQ ID NO:21, or SEQ ID NO:27, or an RNA equivalent or DNA/RNA chimeric thereof, and (B) SEQ ID NO:20, SEQ ID NO:23, or SEQ ID NO:29, or an RNA equivalent or DNA/RNA chimeric thereof;

and (II) the second amplification oligomer combination comprises first and second Bpp-specific amplification oligomers capable of amplifying a target region of a Bpp target nucleic acid, wherein the first and second Bpp-specific amplification oligomers comprise, respectively, first (A') and second (B') Bpp-specific target-hybridizing sequences selected from the group consisting of (c) (A') SEQ ID NO:30, SEQ ID NO:36, or SEQ ID NO:39, or an RNA equivalent or DNA/RNA chimeric thereof, and (B') SEQ ID NO:32, SEQ ID NO:38, or SEQ ID NO:41, or an RNA equivalent or DNA/RNA chimeric thereof;

(d) (A') SEQ ID NO:33, or an RNA equivalent or DNA/RNA chimeric thereof, and (B') SEQ ID NO:35, or an RNA equivalent or DNA/RNA chimeric thereof; and (e) (A') SEQ ID NO:42, or an RNA equivalent or DNA/RNA chimeric thereof, and (B') SEQ ID NO:44, or an RNA equivalent or DNA/RNA chimeric thereof.

Embodiment 35 is the kit of embodiment 34, further comprising a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 36 is the kit of embodiment 34, wherein the first (A) and second (B) Bp specific target-hybridizing sequences are selected from the group consisting of (i) (A) SEQ ID NO:3, or an RNA equivalent or DNA/RNA chimeric thereof, and (B) SEQ ID NO:5, or an RNA equivalent or DNA/RNA chimeric thereof;

(ii) (A) SEQ ID NO:6, or an RNA equivalent or DNA/RNA chimeric thereof, and (B) SEQ ID NO:8, or an RNA equivalent or DNA/RNA chimeric thereof;

(iii) (A) SEQ ID NO:9, or an RNA equivalent or DNA/RNA chimeric thereof, and (B) SEQ ID NO:11, or an RNA equivalent or DNA/RNA chimeric thereof;

(iv) (A) SEQ ID NO:12, or an RNA equivalent or DNA/RNA chimeric thereof, and (B) SEQ ID NO:14, or an RNA equivalent or DNA/RNA chimeric thereof;

(v) (A) SEQ ID NO:18, or an RNA equivalent or DNA/RNA chimeric thereof, and (B) SEQ ID NO:20, or an RNA equivalent or DNA/RNA chimeric thereof;

(vi) (A) SEQ ID NO:21, or an RNA equivalent or DNA/RNA chimeric thereof, and (B) SEQ ID NO:23, or an RNA equivalent or DNA/RNA chimeric thereof; and (vii) (A) SEQ ID NO:27, or an RNA equivalent or DNA/RNA chimeric thereof, and (B) SEQ ID NO:29, or an RNA equivalent or DNA/RNA chimeric thereof.

Embodiment 37 is the kit of embodiment 36, further comprising a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 38 is the kit of embodiment 37, wherein the first and second Bp-specific target-hybridizing sequences are the target-hybridizing sequences of (i) and the Bp-specific detection probe target-hybridizing sequence is SEQ ID NO: 4, or an RNA equivalent or DNA/RNA chimeric thereof;

the first and second Bp-specific target-hybridizing sequences are the target-hybridizing sequences of (ii) and the Bp-specific detection probe target-hybridizing sequence is SEQ ID NO: 7, or an RNA equivalent or DNA/RNA chimeric thereof;

the first and second Bp-specific target-hybridizing sequences are the target-hybridizing sequences of (iii) and the Bp-specific detection probe target-hybridizing sequence is SEQ ID NO: 10, or an RNA equivalent or DNA/RNA chimeric thereof;

the first and second Bp-specific target-hybridizing sequences are the target-hybridizing sequences of (iv) and the Bp-specific detection probe target-hybridizing sequence is SEQ ID NO: 13, or an RNA equivalent or DNA/RNA chimeric thereof;

the first and second Bp-specific target-hybridizing sequences are the target-hybridizing sequences of (v) and the Bp-specific detection probe target-hybridizing sequence is SEQ ID NO: 16, or an RNA equivalent or DNA/RNA chimeric thereof;

the first and second Bp-specific target-hybridizing sequences are the target-hybridizing sequences of (vi) and the Bp-specific detection probe target-hybridizing sequence is SEQ ID NO: 19, or an RNA equivalent or DNA/RNA chimeric thereof;

the first and second Bp-specific target-hybridizing sequences are the target-hybridizing sequences of (vii) and the Bp-specific detection probe target-hybridizing sequence is SEQ ID NO: 22, or an RNA equivalent or DNA/RNA chimeric thereof; or the first and second Bp-specific target-hybridizing sequences are the target-hybridizing sequences of (viii) and the Bp-specific detection probe target-hybridizing sequence is SEQ ID NO: 28, or an RNA equivalent or DNA/RNA chimeric thereof.

Embodiment 39 is the kit of any one of embodiments 35, 37, and 38, wherein the Bp-specific detection probe oligomer further comprises a detectable label.

Embodiment 40 is the kit of embodiment 39, wherein the detectable label is a fluorescent or chemiluminescent label.

Embodiment 41 is the kit of embodiment 39, wherein the detectable label is a fluorescent label and the Bp-specific detection probe oligomer further comprises a non-fluorescent quencher.

Embodiment 42 is the kit of any one of embodiments 34 to 42, further comprising a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 43 is the kit of any one of embodiments 34 to 42, wherein the first (A') and second (B') Bpp-specific target-hybridizing sequences are selected from the group consisting of (i') (A') SEQ ID NO:30, or an RNA equivalent or DNA/RNA chimeric thereof, and (B') SEQ ID NO:32, or an RNA equivalent or DNA/RNA chimeric thereof;

(ii') (A') SEQ ID NO:33, or an RNA equivalent or DNA/RNA chimeric thereof, and (B') SEQ ID NO:35, or an RNA equivalent or DNA/RNA chimeric thereof;

(iii') (A') SEQ ID NO:36, or an RNA equivalent or DNA/RNA chimeric thereof, and (B') SEQ ID NO:38, or an RNA equivalent or DNA/RNA chimeric thereof;

(iv') (A') SEQ ID NO:39, or an RNA equivalent or DNA/RNA chimeric thereof, and (B') SEQ ID NO:41, or an RNA equivalent or DNA/RNA chimeric thereof; and (v') (A') SEQ ID NO:42, or an RNA equivalent or DNA/RNA chimeric thereof, and (B') SEQ ID NO:44, or an RNA equivalent or DNA/RNA chimeric thereof.

Embodiment 44 is the kit of embodiment 43, further comprising a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 45 is the kit of embodiment 44, wherein the first and second Bpp-specific target-hybridizing sequences are the target-hybridizing sequences of (i') and the Bpp-specific detection probe target-hybridizing sequence is SEQ ID NO: 31, or an RNA equivalent or DNA/RNA chimeric thereof;

the first and second Bpp-specific target-hybridizing sequences are the target-hybridizing sequences of (ii') and the Bpp-specific detection probe target-hybridizing sequence is SEQ ID NO: 34, or an RNA equivalent or DNA/RNA chimeric thereof;

the first and second Bpp-specific target-hybridizing sequences are the target-hybridizing sequences of (iii') and the Bpp-specific detection probe target-hybridizing sequence is SEQ ID NO: 37, or an RNA equivalent or DNA/RNA chimeric thereof;

the first and second Bpp-specific target-hybridizing sequences are the target-hybridizing sequences of (iv') and the Bpp-specific detection probe target-hybridizing sequence is SEQ ID NO: 40, or an RNA equivalent or DNA/RNA chimeric thereof; or the first and second Bpp-specific target-hybridizing sequences are the target-hybridizing sequences of (v') and the Bpp-specific detection probe target-hybridizing sequence is SEQ ID NO: 43, or an RNA equivalent or DNA/RNA chimeric thereof.

Embodiment 46 is the kit of any one of embodiments 42, 44, and 45, wherein the Bpp-specific detection probe oligomer further comprises a detectable label.

Embodiment 47 is the kit of embodiment 46, wherein the detectable label is a fluorescent or chemiluminescent label.

Embodiment 48 is the kit of embodiment 46, wherein the detectable label is a fluorescent label and the detection probe oligomer further comprises a non-fluorescent quencher.

Embodiment 49 is a kit for determining the presence or absence of *Bordetella pertussis* (Bp) in a sample, said kit comprising:

an amplification oligomer combination comprising first and second Bp-specific amplification oligomers capable of amplifying a target region of a Bp target nucleic acid, wherein the first and second Bp-specific amplification oligomers comprise, respectively, first (A) and second (B) Bp-specific target-hybridizing sequences selected from the group consisting of (a) (A) SEQ ID NO:3, SEQ ID NO:6, SEQ ID NO:9, SEQ ID NO:12, or SEQ ID NO: 45, or an RNA equivalent or DNA/RNA chimeric thereof, and (B) SEQ ID NO:5, SEQ ID NO:8, SEQ ID NO:11, SEQ ID NO:14, or SEQ ID NO:46, or an RNA equivalent or DNA/RNA chimeric thereof; and (b) (A) SEQ ID NO:18, SEQ ID NO:21, or SEQ ID NO:27, or an RNA equivalent or DNA/RNA chimeric thereof, and (B) SEQ ID NO:20, SEQ ID NO:23, or SEQ ID NO:29, or an RNA equivalent or DNA/RNA chimeric thereof.

Embodiment 50 is the kit of embodiment 49, further comprising a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 51 is the kit of embodiment 49, wherein the first (A) and second (B) Bp specific target-hybridizing sequences are selected from the group consisting of (i) (A) SEQ ID NO:3, or an RNA equivalent or DNA/RNA chimeric thereof, and (B) SEQ ID NO:5, or an RNA equivalent or DNA/RNA chimeric thereof;

(ii) (A) SEQ ID NO:6, or an RNA equivalent or DNA/RNA chimeric thereof, and (B) SEQ ID NO:8, or an RNA equivalent or DNA/RNA chimeric thereof;

(iii) (A) SEQ ID NO:9, or an RNA equivalent or DNA/RNA chimeric thereof, and (B) SEQ ID NO:11, or an RNA equivalent or DNA/RNA chimeric thereof;

(iv) (A) SEQ ID NO:12, or an RNA equivalent or DNA/RNA chimeric thereof, and (B) SEQ ID NO:14, or an RNA equivalent or DNA/RNA chimeric thereof;

(v) (A) SEQ ID NO:18, or an RNA equivalent or DNA/RNA chimeric thereof, and (B) SEQ ID NO:20, or an RNA equivalent or DNA/RNA chimeric thereof;

(vi) (A) SEQ ID NO:21, or an RNA equivalent or DNA/RNA chimeric thereof, and (B) SEQ ID NO:23, or an RNA equivalent or DNA/RNA chimeric thereof; and (vii) (A) SEQ ID NO:27, or an RNA equivalent or DNA/RNA chimeric thereof, and (B) SEQ ID NO:29, or an RNA equivalent or DNA/RNA chimeric thereof.

Embodiment 52 is the kit of embodiment 51, further comprising a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 53 is the kit of embodiment 52, wherein the first and second Bp-specific target-hybridizing sequences are the target-hybridizing sequences of (i) and the Bp-specific detection probe target-hybridizing sequence is SEQ ID NO: 4, or an RNA equivalent or DNA/RNA chimeric thereof;

the first and second Bp-specific target-hybridizing sequences are the target-hybridizing sequences of (ii) and the Bp-specific detection probe target-hybridizing sequence is SEQ ID NO: 7, or an RNA equivalent or DNA/RNA chimeric thereof;

the first and second Bp-specific target-hybridizing sequences are the target-hybridizing sequences of (iii) and the Bp-specific detection probe target-hybridizing sequence is SEQ ID NO: 10, or an RNA equivalent or DNA/RNA chimeric thereof;

the first and second Bp-specific target-hybridizing sequences are the target-hybridizing sequences of (iv) and the Bp-specific detection probe target-hybridizing sequence is SEQ ID NO: 13, or an RNA equivalent or DNA/RNA chimeric thereof;

the first and second Bp-specific target-hybridizing sequences are the target-hybridizing sequences of (v) and the Bp-specific detection probe target-hybridizing sequence is SEQ ID NO: 16, or an RNA equivalent or DNA/RNA chimeric thereof;

the first and second Bp-specific target-hybridizing sequences are the target-hybridizing sequences of (vi) and the Bp-specific detection probe target-hybridizing sequence is SEQ ID NO: 19, or an RNA equivalent or DNA/RNA chimeric thereof;

the first and second Bp-specific target-hybridizing sequences are the target-hybridizing sequences of (vii) and the Bp-specific detection probe target-hybridizing sequence is SEQ ID NO: 22, or an RNA equivalent or DNA/RNA chimeric thereof; or the first and second Bp-specific target-hybridizing sequences are the target-hybridizing sequences of (viii) and the Bp-specific detection probe target-hybridizing sequence is SEQ ID NO: 28, or an RNA equivalent or DNA/RNA chimeric thereof.

Embodiment 54 is the kit of any one of embodiments 50, 52, and 53, wherein the Bp-specific detection probe oligomer further comprises a detectable label.

Embodiment 55 is the kit of embodiment 54, wherein the detectable label is a fluorescent or chemiluminescent label.

Embodiment 56 is the kit of embodiment 54, wherein the detectable label is a fluorescent label and the Bp-specific detection probe oligomer further comprises a non-fluorescent quencher.

Embodiment 57 is the kit of any one of embodiments 49 to 56, further comprising a second amplification oligomer combination capable of amplifying a target region of a *Bordetella parapertussis* (Bpp) target nucleic acid.

Embodiment 58 is a kit for determining the presence or absence of *Bordetella parapertussis* (Bpp) in a sample, said kit comprising:

an amplification oligomer combination comprising first and second Bpp-specific amplification oligomers capable of amplifying a target region of a Bpp target nucleic acid, wherein the first and second Bpp-specific amplification oligomers comprise, respectively, first (A') and second (B') Bpp-specific target-hybridizing sequences selected from the group consisting of (a) (A') SEQ ID NO:30, SEQ ID NO:36, or SEQ ID NO:39, or an RNA equivalent or DNA/RNA chimeric thereof, and (B') SEQ ID NO:32, SEQ ID NO:38, or SEQ ID NO:41, or an RNA equivalent or DNA/RNA chimeric thereof;

(b) (A') SEQ ID NO:33, or an RNA equivalent or DNA/RNA chimeric thereof, and (B') SEQ ID NO:35, or an RNA equivalent or DNA/RNA chimeric thereof; and (c) (A') SEQ ID NO:42, or an RNA equivalent or DNA/RNA chimeric thereof, and (B') SEQ ID NO:44, or an RNA equivalent or DNA/RNA chimeric thereof.

Embodiment 59 is the kit of embodiment 58, further comprising a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 60 is the kit of embodiment 58, wherein the first (A') and second (B') Bpp-specific target-hybridizing sequences are selected from the group consisting of (i') (A') SEQ ID NO:30, or an RNA equivalent or DNA/RNA chimeric thereof, and (B') SEQ ID NO:32, or an RNA equivalent or DNA/RNA chimeric thereof;

(ii') (A') SEQ ID NO:33, or an RNA equivalent or DNA/RNA chimeric thereof, and (B') SEQ ID NO:35, or an RNA equivalent or DNA/RNA chimeric thereof;

(iii') (A') SEQ ID NO:36, or an RNA equivalent or DNA/RNA chimeric thereof, and (B') SEQ ID NO:38, or an RNA equivalent or DNA/RNA chimeric thereof;

(iv') (A') SEQ ID NO:39, or an RNA equivalent or DNA/RNA chimeric thereof, and (B') SEQ ID NO:41, or an RNA equivalent or DNA/RNA chimeric thereof; and (v") (A') SEQ ID NO:42, or an RNA equivalent or DNA/RNA chimeric thereof, and (B') SEQ ID NO:44, or an RNA equivalent or DNA/RNA chimeric thereof.

Embodiment 61 is the kit of embodiment 60, further comprising a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 62 is the kit of embodiment 61, wherein the first and second Bpp-specific target-hybridizing sequences are the target-hybridizing sequences of (i') and the Bpp-specific detection probe target-hybridizing sequence is SEQ ID NO: 31, or an RNA equivalent or DNA/RNA chimeric thereof;

the first and second Bpp-specific target-hybridizing sequences are the target-hybridizing sequences of (ii') and the Bpp-specific detection probe target-hybridizing sequence is SEQ ID NO: 34, or an RNA equivalent or DNA/RNA chimeric thereof;

the first and second Bpp-specific target-hybridizing sequences are the target-hybridizing sequences of (iii') and the Bpp-specific detection probe target-hybridizing sequence is SEQ ID NO: 37, or an RNA equivalent or DNA/RNA chimeric thereof;

the first and second Bpp-specific target-hybridizing sequences are the target-hybridizing sequences of (iv') and the Bpp-specific detection probe target-hybridizing sequence is SEQ ID NO: 40, or an RNA equivalent or DNA/RNA chimeric thereof; or the first and second Bpp-specific target-hybridizing sequences are the target-hybridizing sequences of (v') and the Bpp-specific detection probe target-hybridizing sequence is SEQ ID NO: 43, or an RNA equivalent or DNA/RNA chimeric thereof.

Embodiment 63 is the kit of any one of embodiments 59, 61, and 62, wherein the Bpp-specific detection probe oligomer further comprises a detectable label.

Embodiment 64 is the kit of embodiment 63, wherein the detectable label is a fluorescent or chemiluminescent label.

Embodiment 65 is the kit of embodiment 63, wherein the detectable label is a fluorescent label and the detection probe oligomer further comprises a non-fluorescent quencher.

Embodiment 66 is the kit of any one of embodiments 58 to 65, further comprising a second amplification oligomer combination capable of amplifying a target region of a *Bordetella pertussis* (Bp) target nucleic acid.

Embodiment 67 is a method for determining the presence or absence of each of *Bordetella pertussis* (Bp) and *Bordetella parapertussis* (Bpp) in a sample, said method comprising:

(1) contacting a sample suspected of containing at least one of *Bordetella pertussis* (Bp) and *Bordetella parapertussis* (Bpp) with a first amplification oligomer combination and a second amplification oligomer combination, wherein (I) the first amplification oligomer combination comprises first and second Bp-specific amplification oligomers capable of amplifying a target region of a Bp target nucleic acid, wherein the first and second Bp-specific amplification oligomers comprise, respectively, first (A) and second (B) Bp-specific target-hybridizing sequences selected from the group consisting of (a) (A) SEQ ID NO:3, SEQ ID NO:6, SEQ ID NO:9, SEQ ID NO:12, or SEQ ID NO: 45, or an RNA equivalent or DNA/RNA chimeric thereof, and (B) SEQ ID NO:5, SEQ ID NO:8, SEQ ID NO:11, SEQ ID NO:14, or SEQ ID NO:46, or an RNA equivalent or DNA/RNA chimeric thereof; and (b) (A) SEQ ID NO:18, SEQ ID NO:21, or SEQ ID NO:27, or an RNA equivalent or DNA/RNA chimeric thereof, and (B) SEQ ID NO:20, SEQ ID NO:23, or SEQ ID NO:29, or an RNA equivalent or DNA/RNA chimeric thereof;

and (II) the second amplification oligomer combination comprises first and second Bpp-specific amplification oligomers capable of amplifying a target region of a Bpp target nucleic acid, wherein the first and second Bpp-specific amplification oligomers comprise, respectively, first (A') and second (B') Bpp-specific target-hybridizing sequences selected from the group consisting of (a) (A') SEQ ID NO:30, SEQ ID NO:36, or SEQ ID NO:39, or an RNA equivalent or DNA/RNA chimeric thereof, and (B') SEQ ID NO:32, SEQ ID NO:38, or SEQ ID NO:41, or an RNA equivalent or DNA/RNA chimeric thereof;

(b) (A') SEQ ID NO:33, or an RNA equivalent or DNA/RNA chimeric thereof, and (B') SEQ ID NO:35, or an RNA equivalent or DNA/RNA chimeric thereof; and (c) (A') SEQ ID NO:42, or an RNA equivalent or DNA/RNA chimeric thereof, and (B') SEQ ID NO:44, or an RNA equivalent or DNA/RNA chimeric thereof;

(2) performing an in vitro nucleic acid amplification reaction, wherein any Bp and/or Bpp target nucleic acid, if present in the sample, is used as a template for generating one or more amplicons corresponding to at least one of the Bp and Bpp target regions; and (3) detecting the presence or absence of the one or more amplicons, thereby determining the presence or absence of Bp and Bpp in the sample.

Embodiment 68 is the method of embodiment 67, wherein the method is a multiplex method comprising contacting the sample with the first and second amplification oligomer combinations within the same reaction mixture.

Embodiment 69 is the method of embodiment 67 or 68, wherein the detecting step comprises contacting the in vitro nucleic acid amplification reaction with a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 70 is the method of embodiment 67 or 68, wherein the first (A) and second (B) Bp specific target-hybridizing sequences are selected from the group consisting of (i) (A) SEQ ID NO:3, or an RNA equivalent or DNA/RNA chimeric thereof, and (B) SEQ ID NO:5, or an RNA equivalent or DNA/RNA chimeric thereof;

(ii) (A) SEQ ID NO:6, or an RNA equivalent or DNA/RNA chimeric thereof, and (B) SEQ ID NO:8, or an RNA equivalent or DNA/RNA chimeric thereof;

(iii) (A) SEQ ID NO:9, or an RNA equivalent or DNA/RNA chimeric thereof, and (B) SEQ ID NO:11, or an RNA equivalent or DNA/RNA chimeric thereof;

(iv) (A) SEQ ID NO:12, or an RNA equivalent or DNA/RNA chimeric thereof, and (B) SEQ ID NO:14, or an RNA equivalent or DNA/RNA chimeric thereof;

(v) (A) SEQ ID NO:18, or an RNA equivalent or DNA/RNA chimeric thereof, and (B) SEQ ID NO:20, or an RNA equivalent or DNA/RNA chimeric thereof;

(vi) (A) SEQ ID NO:21, or an RNA equivalent or DNA/RNA chimeric thereof, and (B) SEQ ID NO:23, or an RNA equivalent or DNA/RNA chimeric thereof; and (vii) (A) SEQ ID NO:27, or an RNA equivalent or DNA/RNA chimeric thereof, and (B) SEQ ID NO:29, or an RNA equivalent or DNA/RNA chimeric thereof.

Embodiment 71 is the method of embodiment 70, wherein the detecting step comprises contacting the in vitro nucleic acid amplification reaction with a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 72 is the method of embodiment 71, wherein the first and second Bp-specific target-hybridizing sequences are the target-hybridizing sequences of (i) and the Bp-specific detection probe target-hybridizing sequence is SEQ ID NO: 4, or an RNA equivalent or DNA/RNA chimeric thereof;

the first and second Bp-specific target-hybridizing sequences are the target-hybridizing sequences of (ii) and the Bp-specific detection probe target-hybridizing sequence is SEQ ID NO: 7, or an RNA equivalent or DNA/RNA chimeric thereof;

the first and second Bp-specific target-hybridizing sequences are the target-hybridizing sequences of (iii) and the Bp-specific detection probe target-hybridizing sequence is SEQ ID NO: 10, or an RNA equivalent or DNA/RNA chimeric thereof;

the first and second Bp-specific target-hybridizing sequences are the target-hybridizing sequences of (iv) and the Bp-specific detection probe target-hybridizing sequence is SEQ ID NO: 13, or an RNA equivalent or DNA/RNA chimeric thereof;

the first and second Bp-specific target-hybridizing sequences are the target-hybridizing sequences of (v) and the Bp-specific detection probe target-hybridizing sequence is SEQ ID NO: 16, or an RNA equivalent or DNA/RNA chimeric thereof;

the first and second Bp-specific target-hybridizing sequences are the target-hybridizing sequences of (vi) and the Bp-specific detection probe target-hybridizing sequence is SEQ ID NO: 19, or an RNA equivalent or DNA/RNA chimeric thereof;

the first and second Bp-specific target-hybridizing sequences are the target-hybridizing sequences of (vii) and the Bp-specific detection probe target-hybridizing sequence is SEQ ID NO: 22, or an RNA equivalent or DNA/RNA chimeric thereof; or the first and second Bp-specific target-hybridizing sequences are the target-hybridizing sequences of (viii) and the Bp-specific detection probe target-hybridizing sequence is SEQ ID NO: 28, or an RNA equivalent or DNA/RNA chimeric thereof.

Embodiment 73 is the method of any one of embodiments 69, 71, and 72, wherein the Bp-specific detection probe oligomer further comprises a detectable label.

Embodiment 74 is the method of embodiment 73, wherein the detectable label is a fluorescent or chemiluminescent label.

Embodiment 75 is the method of embodiment 73, wherein the detectable label is a fluorescent label and the Bp-specific detection probe oligomer further comprises a non-fluorescent quencher.

Embodiment 76 is the method of any one of embodiments 67 to 75, wherein the detecting step comprises contacting the in vitro nucleic acid amplification reaction with a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 77 is the method of any one of embodiments 67 to 75, wherein the first (A') and second (B') Bpp-specific target-hybridizing sequences are selected from the group consisting of (i') (A') SEQ ID NO:30, or an RNA equivalent or DNA/RNA chimeric thereof, and (B') SEQ ID NO:32, or an RNA equivalent or DNA/RNA chimeric thereof;

(ii') (A') SEQ ID NO:33, or an RNA equivalent or DNA/RNA chimeric thereof, and (B') SEQ ID NO:35, or an RNA equivalent or DNA/RNA chimeric thereof;

(iii') (A') SEQ ID NO:36, or an RNA equivalent or DNA/RNA chimeric thereof, and (B') SEQ ID NO:38, or an RNA equivalent or DNA/RNA chimeric thereof;

(iv') (A') SEQ ID NO:39, or an RNA equivalent or DNA/RNA chimeric thereof, and (B') SEQ ID NO:41, or an RNA equivalent or DNA/RNA chimeric thereof; and (v'') (A') SEQ ID NO:42, or an RNA equivalent or DNA/RNA chimeric thereof, and (B') SEQ ID NO:44, or an RNA equivalent or DNA/RNA chimeric thereof.

Embodiment 78 is the method of embodiment 77, wherein the detecting step comprises contacting the in vitro nucleic acid amplification reaction with a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 79 is the method of embodiment 78, wherein the first and second Bpp-specific target-hybridizing sequences are the target-hybridizing sequences of (i') and the Bpp-specific detection probe target-hybridizing sequence is SEQ ID NO: 31, or an RNA equivalent or DNA/RNA chimeric thereof;

the first and second Bpp-specific target-hybridizing sequences are the target-hybridizing sequences of (ii') and the Bpp-specific detection probe target-hybridizing sequence is SEQ ID NO: 34, or an RNA equivalent or DNA/RNA chimeric thereof;

the first and second Bpp-specific target-hybridizing sequences are the target-hybridizing sequences of (iii') and the Bpp-specific detection probe target-hybridizing sequence is SEQ ID NO: 37, or an RNA equivalent or DNA/RNA chimeric thereof;

the first and second Bpp-specific target-hybridizing sequences are the target-hybridizing sequences of (iv') and the Bpp-specific detection probe target-hybridizing sequence is SEQ ID NO: 40, or an RNA equivalent or DNA/RNA chimeric thereof; or the first and second Bpp-specific target-hybridizing sequences are the target-hybridizing sequences of (v') and the Bpp-specific detection probe target-hybridizing sequence is SEQ ID NO: 43, or an RNA equivalent or DNA/RNA chimeric thereof.

Embodiment 80 is the method of any one of embodiments 76, 78, and 79, wherein the Bpp-specific detection probe oligomer further comprises a detectable label.

Embodiment 81 is the method of embodiment 80, wherein the detectable label is a fluorescent or chemiluminescent label.

Embodiment 82 is the method of embodiment 80, wherein the detectable label is a fluorescent label and the detection probe oligomer further comprises a non-fluorescent quencher.

Embodiment 83 is the method of any one of embodiments 69, 71-76, and 78-82, wherein the detecting step is performed in real time.

Embodiment 84 is the method of any one of embodiments 67 to 83, wherein the in vitro nucleic acid amplification reaction is a PCR amplification reaction.

Embodiment 85 is the method of embodiment 68, wherein the detecting step comprises contacting the in vitro nucleic acid amplification reaction with (i) a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers, and (ii) a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers, wherein each of said Bp-specific and Bpp-specific detection probe oligomers comprises a fluorescent label and a non-fluorescent quencher.

Embodiment 86 is the method of embodiment 85, wherein the in vitro nucleic acid amplification reaction is a real-time PCR amplification reaction.

Embodiment 87 is the method of any one of embodiments 65 to 86, wherein the method is performed on an automated system comprising an amplification module and a detection module.

Embodiment 88 is the method of embodiment 87, wherein the automated system is a Panther Fusion system.

Embodiment 89 is a method for determining the presence or absence of *Bordetella pertussis* (Bp) in a sample, said method comprising:

(1) contacting a sample suspected of containing Bp with an amplification oligomer combination comprising first and second Bp-specific amplification oligomers capable of amplifying a target region of a Bp target nucleic acid, wherein the first and second Bp-specific amplification oligomers comprise, respectively, first (A) and second (B) Bp-specific target-hybridizing sequences selected from the group consisting of a. (A) SEQ ID NO:3, SEQ ID NO:6, SEQ ID NO:9, SEQ ID NO:12, or SEQ ID NO:45, or an RNA equivalent or DNA/RNA chimeric thereof, and (B) SEQ ID NO:5, SEQ ID NO:8, SEQ ID NO:11, SEQ ID NO: 14, or SEQ ID NO:46, or an RNA equivalent or DNA/RNA chimeric thereof; and b. (A) SEQ ID NO:18, SEQ ID NO:21, or SEQ ID NO:27, or an RNA equivalent or DNA/RNA chimeric thereof, and (B) SEQ ID NO:20, SEQ ID NO:23, or SEQ ID NO:29, or an RNA equivalent or DNA/RNA chimeric thereof;

(2) performing an in vitro nucleic acid amplification reaction, wherein any Bp target nucleic acid, if present in the sample, is used as a template for generating an amplicon corresponding to the Bp target region; and (3) detecting the presence or absence of the amplicon, thereby determining the presence or absence of Bp in the sample.

Embodiment 90 is the method of embodiment 89, wherein the detecting step comprises contacting the in vitro nucleic acid amplification reaction with a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 91 is the method of embodiment 89, wherein the first (A) and second (B) Bp specific target-hybridizing sequences are selected from the group consisting of (i) (A) SEQ ID NO:3, or an RNA equivalent or DNA/RNA chimeric thereof, and (B) SEQ ID NO:5, or an RNA equivalent or DNA/RNA chimeric thereof;

(ii) (A) SEQ ID NO:6, or an RNA equivalent or DNA/RNA chimeric thereof, and (B) SEQ ID NO:8, or an RNA equivalent or DNA/RNA chimeric thereof;

(iii) (A) SEQ ID NO:9, or an RNA equivalent or DNA/RNA chimeric thereof, and (B) SEQ ID NO:11, or an RNA equivalent or DNA/RNA chimeric thereof;

(iv) (A) SEQ ID NO:12, or an RNA equivalent or DNA/RNA chimeric thereof, and (B) SEQ ID NO:14, or an RNA equivalent or DNA/RNA chimeric thereof;

(v) (A) SEQ ID NO:18, or an RNA equivalent or DNA/RNA chimeric thereof, and (B) SEQ ID NO:20, or an RNA equivalent or DNA/RNA chimeric thereof;

(vi) (A) SEQ ID NO:21, or an RNA equivalent or DNA/RNA chimeric thereof, and (B) SEQ ID NO:23, or an RNA equivalent or DNA/RNA chimeric thereof; and (vii) (A) SEQ ID NO:27, or an RNA equivalent or DNA/RNA chimeric thereof, and (B) SEQ ID NO:29, or an RNA equivalent or DNA/RNA chimeric thereof.

Embodiment 92 is the method of embodiment 91, wherein the detecting step comprises contacting the in vitro nucleic acid amplification reaction with a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers.

Embodiment 93 is the method of embodiment 92, wherein the first and second Bp-specific target-hybridizing sequences are the target-hybridizing sequences of (i) and the Bp-specific detection probe target-hybridizing sequence is SEQ ID NO: 4, or an RNA equivalent or DNA/RNA chimeric thereof;

the first and second Bp-specific target-hybridizing sequences are the target-hybridizing sequences of (ii) and the Bp-specific detection probe target-hybridizing sequence is SEQ ID NO: 7, or an RNA equivalent or DNA/RNA chimeric thereof;

the first and second Bp-specific target-hybridizing sequences are the target-hybridizing sequences of (iii) and the Bp-specific detection probe target-hybridizing sequence is SEQ ID NO: 10, or an RNA equivalent or DNA/RNA chimeric thereof;

the first and second Bp-specific target-hybridizing sequences are the target-hybridizing sequences of (iv) and the Bp-specific detection probe target-hybridizing sequence is SEQ ID NO: 13, or an RNA equivalent or DNA/RNA chimeric thereof;

the first and second Bp-specific target-hybridizing sequences are the target-hybridizing sequences of (v) and the Bp-specific detection probe target-hybridizing sequence is SEQ ID NO: 16, or an RNA equivalent or DNA/RNA chimeric thereof;

the first and second Bp-specific target-hybridizing sequences are the target-hybridizing sequences of (vi) and the Bp-specific detection probe target-hybridizing sequence is SEQ ID NO: 19, or an RNA equivalent or DNA/RNA chimeric thereof;

the first and second Bp-specific target-hybridizing sequences are the target-hybridizing sequences of (vii) and the Bp-specific detection probe target-hybridizing sequence is SEQ ID NO: 22, or an RNA equivalent or DNA/RNA chimeric thereof; or the first and second Bp-specific target-hybridizing sequences are the target-hybridizing sequences of (viii) and the Bp-specific detection probe target-hybridizing sequence is SEQ ID NO: 28, or an RNA equivalent or DNA/RNA chimeric thereof.

Embodiment 94 is the method of any one of embodiments 90, 92, and 93, wherein the Bp-specific detection probe oligomer further comprises a detectable label.

Embodiment 95 is the method of embodiment 94, wherein the detectable label is a fluorescent or chemiluminescent label.

Embodiment 96 is the method of embodiment 94, wherein the detectable label is a fluorescent label and the Bp-specific detection probe oligomer further comprises a non-fluorescent quencher.

Embodiment 97 is the method of any one of embodiments 89 to 93, wherein the detecting step is performed in real time.

Embodiment 98 is the method of any one of embodiments 89 to 97, wherein the in vitro nucleic acid amplification reaction is a PCR amplification reaction.

Embodiment 99 is the method of embodiment 96, wherein the in vitro nucleic acid amplification reaction is a real-time PCR amplification reaction.

Embodiment 100 is the method of any one of embodiments 89 to 99, further comprising contacting the sample with a second amplification oligomer combination comprising first and second *Bordetella parapertussis* (Bpp)-specific amplification oligomers capable of amplifying a target region of a Bpp target nucleic acid, wherein, at the amplification step, any Bpp target nucleic acid, if present in the sample, is used as a template for generating an amplicon corresponding to the Bpp target region, and wherein the detecting step comprises detecting the presence or absence of the amplicon corresponding to the Bpp target region.

Embodiment 101 is a method for determining the presence or absence of *Bordetella parapertussis* (Bpp) in a sample, said method comprising:

(1) contacting a sample suspected of containing Bpp with an amplification oligomer combination comprising first and second Bpp-specific amplification oligomers capable of amplifying a target region of a Bpp target nucleic acid, wherein the first and second Bpp-specific amplification oligomers comprise, respectively, first (A') and second (B') Bpp-specific target-hybridizing sequences selected from the group consisting of a. (A') SEQ ID NO:30, SEQ ID NO:36, or SEQ ID NO:39, or an RNA equivalent or DNA/RNA chimeric thereof, and (B') SEQ ID NO:32, SEQ ID NO:38, or SEQ ID NO:41, or an RNA equivalent or DNA/RNA chimeric thereof;

b. (A') SEQ ID NO:33, or an RNA equivalent or DNA/RNA chimeric thereof, and (B') SEQ ID NO:35, or an RNA equivalent or DNA/RNA chimeric thereof; and c. (A') SEQ ID NO:42, or an RNA equivalent or DNA/RNA chimeric thereof, and (B') SEQ ID NO:44, or an RNA equivalent or DNA/RNA chimeric thereof;

(2) performing an in vitro nucleic acid amplification reaction, wherein any Bpp target nucleic acid, if present in the sample, is used as a template for generating an amplicon corresponding to the Bpp target region; and (3) detecting the presence or absence of the amplicon, thereby determining the presence or absence of Bpp in the sample.

Embodiment 102 is the method of embodiment 101, wherein the detecting step comprises contacting the in vitro nucleic acid amplification reaction with a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 103 is the method of embodiment 101, wherein the first (A') and second (B') Bpp-specific target-hybridizing sequences are selected from the group consisting of (i') (A') SEQ ID NO:30, or an RNA equivalent or DNA/RNA chimeric thereof, and (B') SEQ ID NO:32, or an RNA equivalent or DNA/RNA chimeric thereof;

(ii') (A') SEQ ID NO:33, or an RNA equivalent or DNA/RNA chimeric thereof, and (B') SEQ ID NO:35, or an RNA equivalent or DNA/RNA chimeric thereof;

(iii') (A') SEQ ID NO:36, or an RNA equivalent or DNA/RNA chimeric thereof, and (B') SEQ ID NO:38, or an RNA equivalent or DNA/RNA chimeric thereof;

(iv') (A') SEQ ID NO:39, or an RNA equivalent or DNA/RNA chimeric thereof, and (B') SEQ ID NO:41, or an RNA equivalent or DNA/RNA chimeric thereof; and (v') (A') SEQ ID NO:42, or an RNA equivalent or DNA/RNA chimeric thereof, and (B') SEQ ID NO:44, or an RNA equivalent or DNA/RNA chimeric thereof.

Embodiment 104 is the method of embodiment 103, wherein the detecting step comprises contacting the in vitro nucleic acid amplification reaction with a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers.

Embodiment 105 is the method of embodiment 104, wherein the first and second Bpp-specific target-hybridizing sequences are the target-hybridizing sequences of (i') and the Bpp-specific detection probe target-hybridizing sequence is SEQ ID NO: 31, or an RNA equivalent or DNA/RNA chimeric thereof;

the first and second Bpp-specific target-hybridizing sequences are the target-hybridizing sequences of (ii') and the Bpp-specific detection probe target-hybridizing sequence is SEQ ID NO: 34, or an RNA equivalent or DNA/RNA chimeric thereof;

the first and second Bpp-specific target-hybridizing sequences are the target-hybridizing sequences of (iii') and the Bpp-specific detection probe target-hybridizing sequence is SEQ ID NO: 37, or an RNA equivalent or DNA/RNA chimeric thereof;

the first and second Bpp-specific target-hybridizing sequences are the target-hybridizing sequences of (iv') and the Bpp-specific detection probe target-hybridizing sequence is SEQ ID NO: 40, or an RNA equivalent or DNA/RNA chimeric thereof; or the first and second Bpp-specific target-hybridizing sequences are the target-hybridizing sequences of (v') and the Bpp-specific detection probe target-hybridizing sequence is SEQ ID NO: 43, or an RNA equivalent or DNA/RNA chimeric thereof.

Embodiment 106 is the method of any one of embodiments 102, 104, and 105, wherein the Bpp-specific detection probe oligomer further comprises a detectable label.

Embodiment 107 is the method of embodiment 106, wherein the detectable label is a fluorescent or chemiluminescent label.

Embodiment 108 is the method of embodiment 106, wherein the detectable label is a fluorescent label and the detection probe oligomer further comprises a non-fluorescent quencher.

Embodiment 109 is the method of any one of embodiments 101 to 105, wherein the detecting step is performed in real time.

Embodiment 110 is the method of any one of embodiments 101 to 109, wherein the in vitro nucleic acid amplification reaction is a PCR amplification reaction.

Embodiment 111 is the method of embodiment 108, wherein the in vitro nucleic acid amplification reaction is a real-time PCR amplification reaction.

Embodiment 112 is the method of any one of embodiments 101 to 111, further comprising contacting the sample with a second amplification oligomer combination comprising first and second *Bordetella pertussis* (Bp)-specific amplification oligomers capable of amplifying a target region of a Bp target nucleic acid, wherein, at the amplification step, any Bp target nucleic acid, if present in the sample, is used as a template for generating an amplicon corresponding to the Bp target region, and wherein the detecting step comprises detecting the presence or absence of the amplicon corresponding to the Bp target region.

Embodiment 113 is a detection probe oligomer comprising:

a *Bordetella pertussis* (Bp)-specific detection probe target-hybridizing sequence that is from about 15 to about 35 nucleotides in length and is configured to hybridize to a target sequence contained within a Bp amplicon amplifiable by a first amplification oligomer combination comprising first and second Bp-specific amplification oligomers capable of amplifying a target region of a Bp target nucleic acid, wherein the first and second Bp-specific amplification oligomers comprise, respectively, first (A) and second (B) Bp-specific target-hybridizing sequences selected from the group consisting of (a) (A) SEQ ID NO:3, SEQ ID NO:6, SEQ ID NO:9, SEQ ID NO:12, or SEQ ID NO: 45, or an RNA equivalent or DNA/RNA chimeric thereof, and (B) SEQ ID NO:5, SEQ ID NO:8, SEQ ID NO:11, SEQ ID NO:14, or SEQ ID NO:46, or an RNA equivalent or DNA/RNA chimeric thereof; and (b) (A) SEQ ID NO:18, SEQ ID NO:21, or SEQ ID NO:27, or an RNA equivalent or DNA/RNA chimeric thereof, and (B) SEQ ID NO:20, SEQ ID NO:23, or SEQ ID NO:29, or an RNA equivalent or DNA/RNA chimeric thereof.

Embodiment 114 is the detection probe oligomer of embodiment 113, wherein the Bp-specific detection probe target-hybridizing sequence is selected from the group consisting of SEQ ID NO:4, SEQ ID NO:7, SEQ ID NO:10, SEQ ID NO: 13, SEQ ID NO: 16, SEQ ID NO: 19, SEQ ID NO:22, and SEQ ID NO:28, including RNA equivalents and DNA/RNA chimerics thereof.

Embodiment 115 is a detection probe oligomer comprising:

a *Bordetella parapertussis* (Bpp)-specific detection probe target-hybridizing sequence that is from about 15 to about 35 nucleotides in length and is configured to hybridize to a target sequence contained within a Bpp amplicon amplifiable by a first amplification oligomer combination comprising first and second Bpp-specific amplification oligomers capable of amplifying a target region of a Bpp target nucleic acid, wherein the first and second Bp-specific amplification oligomers comprise, respectively, first (A') and second (B') Bpp-specific target-hybridizing sequences selected from the group consisting of (a) (A') SEQ ID NO:30, SEQ ID NO:36, or SEQ ID NO:39, or an RNA equivalent or DNA/RNA chimeric thereof, and (B') SEQ ID NO:32, SEQ ID NO:38, or SEQ ID NO:41, or an RNA equivalent or DNA/RNA chimeric thereof;

(b) (A') SEQ ID NO:33, or an RNA equivalent or DNA/RNA chimeric thereof, and (B') SEQ ID NO:35, or an RNA equivalent or DNA/RNA chimeric thereof; and (c) (A') SEQ ID NO:42, or an RNA equivalent or DNA/RNA chimeric thereof, and (B') SEQ ID NO:44, or an RNA equivalent or DNA/RNA chimeric thereof.

Embodiment 116 is the detection probe oligomer of embodiment 115, wherein the Bpp-specific detection probe target-hybridizing sequence is selected from the group consisting of SEQ ID NO:31, SEQ ID NO:34, SEQ ID NO:37, SEQ ID NO:40, and SEQ ID NO:43, including RNA equivalents and DNA/RNA chimerics thereof.

Embodiment 117 is the detection probe oligomer of any one of embodiments 113 to 116, wherein the detection probe oligomer further comprises a detectable label.

Embodiment 118 is the detection probe oligomer of embodiment 117, wherein the detectable label is a fluorescent or chemiluminescent label.

Embodiment 119 is a composition comprising:

(1) a *Bordetella pertussis* (Bp)-specific detection probe target-hybridizing sequence that is from about 15 to about 35 nucleotides in length and is configured to hybridize to a target sequence contained within a Bp amplicon amplifiable by a first amplification oligomer combination comprising first and second Bp-specific amplification oligomers capable of amplifying a target region of a Bp target nucleic acid, wherein the first and second Bp-specific amplification oligomers comprise, respectively, first (A) and second (B) Bp-specific target-hybridizing sequences selected from the group consisting of a. (A) SEQ ID NO:3, SEQ ID NO:6, SEQ ID NO:9, SEQ ID NO: 12, or SEQ ID NO:45, or an RNA equivalent or DNA/RNA chimeric thereof, and (B) SEQ ID NO:5, SEQ ID NO:8, SEQ ID NO:11, SEQ ID NO:14, or SEQ ID NO:46, or an RNA equivalent or DNA/RNA chimeric thereof; and b. (A) SEQ ID NO:18, SEQ ID NO:21, or SEQ ID NO:27, or an RNA equivalent or DNA/RNA chimeric thereof, and (B) SEQ ID NO:20, SEQ ID NO:23, or SEQ ID NO:29, or an RNA equivalent or DNA/RNA chimeric thereof; and (2) a *Bordetella parapertussis* (Bpp)-specific detection probe target-hybridizing sequence that is from about 15 to about 35 nucleotides in length and is configured to hybridize to a target sequence contained within a Bpp amplicon amplifiable by a first amplification oligomer combination comprising first and second Bpp-specific amplification oligomers capable of amplifying a target region of a Bpp target nucleic acid, wherein the first and second Bp-specific amplification oligomers comprise, respectively, first (A') and second (B') Bpp-specific target-hybridizing sequences selected from the group consisting of a. (A') SEQ ID NO:30, SEQ ID NO:36, or SEQ ID NO:39, or an RNA equivalent or DNA/RNA chimeric thereof, and (B') SEQ ID NO:32, SEQ ID NO:38, or SEQ ID NO:41, or an RNA equivalent or DNA/RNA chimeric thereof;

b. (A') SEQ ID NO:33, or an RNA equivalent or DNA/RNA chimeric thereof, and (B') SEQ ID NO:35, or an RNA equivalent or DNA/RNA chimeric thereof; and c. (A') SEQ ID NO:42, or an RNA equivalent or DNA/RNA chimeric thereof, and (B') SEQ ID NO:44, or an RNA equivalent or DNA/RNA chimeric thereof.

Embodiment 120 is the composition of embodiment 119, wherein the (Bp)-specific detection probe target-hybridizing sequence is selected from the group consisting of SEQ ID NO: 4, SEQ ID NO:7, SEQ ID NO: 10, SEQ ID NO: 13, SEQ ID NO: 16, SEQ ID NO: 19, SEQ ID NO: 22, and SEQ ID NO:28, including RNA equivalents and DNA/RNA chimerics thereof.

Embodiment 121 is the composition of embodiment 119 or 120, wherein the (Bpp)-specific detection probe target-hybridizing sequence is selected from the group consisting of SEQ ID NO:31, SEQ ID NO:34, SEQ ID NO:37, SEQ ID NO:40, and SEQ ID NO:43, including RNA equivalents and DNA/RNA chimerics thereof.

Embodiment 122 is the composition of any one of embodiments 119 to 121, wherein the Bp-specific detection probe oligomer further comprises a detectable label.

Embodiment 123 is the composition of any one of embodiments 119 to 122, wherein the Bpp-specific detection probe oligomer further comprises a detectable label.

Embodiment 124 is the composition of embodiment 122 or 123, wherein the detectable label is a fluorescent or chemiluminescent label.

Embodiment 125 is an aqueous formulation for the amplification of at least one of *Bordetella pertussis* (Bp) nucleic acid and *Bordetella parapertussis* (Bpp) nucleic acid, wherein the aqueous formulation comprises:

a. a composition as in any one of embodiments 1 to 15, and b. an organic buffer.

Embodiment 126 is an aqueous formulation for the amplification of *Bordetella pertussis* (Bp) nucleic acid, wherein the aqueous formulation comprises:

a. a composition as in any one of embodiments 16 to 24, and b. an organic buffer.

Embodiment 127 is an aqueous formulation for the amplification of *Bordetella parapertussis* (Bpp) nucleic acid, wherein the aqueous formulation comprises:

a. a composition as in any one of embodiments 25 to 33, and b. an organic buffer.

Embodiment 128 is the aqueous formulation of any one of embodiments 125 to 127, further comprising a DNA polymerase enzyme.

Embodiment 129 is the aqueous formulation of any one of embodiments 125 to 128, further comprising a reverse transcriptase enzyme.

Embodiment 130 is the aqueous formulation of any one of embodiments 125 to 129, further comprising a detection probe oligomer.

Embodiment 131 is the aqueous formulation of any one of embodiments 125 to 130, further comprising a bulking agent selected from the group consisting of trehalose, raffinose, and a combination thereof.

Embodiment 132 is the aqueous formulation of any one of embodiments 125 to 131, wherein the formulation contains inorganic salt at a concentration of 4 mM or less.

Embodiment 133 is a dried formulation for the amplification of at least one of *Bordetella pertussis* (Bp) nucleic acid and *Bordetella parapertussis* (Bpp) nucleic acid, wherein the dried formulation comprises:

a. a composition as in any one of embodiments 1 to 15, and b. a bulking agent.

Embodiment 134 is a dried formulation for the amplification of *Bordetella pertussis* (Bp) nucleic acid, wherein the dried formulation comprises:

a. a composition as in any one of embodiments 16 to 24, and b. a bulking agent.

Embodiment 135 is a dried formulation for the amplification of *Bordetella parapertussis* (Bpp) nucleic acid, wherein the dried formulation comprises:

a. a composition as in any one of embodiments 25 to 33, and b. a bulking agent.

Embodiment 136 is the dried formulation of any one of embodiments 133 to 135, wherein the bulking agent is selected from the group consisting of trehalose, raffinose, and a combination thereof.

Embodiment 137 is the dried formulation of any one of embodiments 133 to 136, further comprising an inorganic salt, wherein the percent mass of the inorganic salt to the mass of the dried formulation is 0.249% or less.

Embodiment 138 is the dried formulation of any one of embodiments 133 to 137, further comprising a DNA polymerase enzyme.

Embodiment 139 is the dried formulation of any one of embodiments 133 to 138, further comprising a reverse transcriptase enzyme.

Embodiment 140 is the dried formulation of any one of embodiments 133 to 139, further comprising a detection probe oligomer.

Embodiment 141 is the dried formulation of any one of embodiments 133 to 140, wherein the formulation is a lyophilized formulation.

Embodiment 142 is an aqueous formulation for the detection of at least one of *Bordetella pertussis* (Bp) nucleic acid and *Bordetella parapertussis* (Bpp) nucleic acid, wherein the aqueous formulation comprises:

a. a composition as in any one of embodiments 119 to 124, and b. an organic buffer.

Embodiment 143 is an aqueous formulation for the detection of *Bordetella pertussis* (Bp) nucleic acid, wherein the aqueous formulation comprises:

a. a detection probe oligomer as in embodiment 113 or 114, and b. an organic buffer.

Embodiment 144 is an aqueous formulation for the detection of *Bordetella parapertussis* (Bpp) nucleic acid, wherein the aqueous formulation comprises:

a. a detection probe oligomer as in embodiment 115 or 116, and b. an organic buffer.

Embodiment 145 is the aqueous formulation of embodiment 142 to 144, further comprising a surfactant.

Embodiment 146 is the aqueous formulation of embodiment 145, wherein the surfactant is a non-linear surfactant.

Embodiment 147 is the aqueous formulation of embodiment 145, wherein the surfactant is selected from the group consisting of a. polyethylene glycol mono [4-(1,1,3,3-tetramethylbutyl) phenyl] ether, b. polysorbate 20, and c. a combination thereof.

Embodiment 148 is the aqueous formulation of any one of embodiments 142 to 147, further comprising a DNA polymerase enzyme.

Embodiment 149 is the aqueous formulation of any one of embodiments 142 to 148, further comprising a reverse transcriptase enzyme.

Embodiment 150 is the aqueous formulation of any one of embodiments 142 to 149, further comprising at least one amplification oligomer.

Embodiment 151 is the aqueous formulation of any one of embodiments 142 to 150, further comprising a bulking agent selected from the group consisting of trehalose, raffinose, and a combination thereof.

Embodiment 152 is the aqueous formulation of any one of embodiments 142 to 151, wherein the formulation contains inorganic salt at a concentration of 4 mM or less.

Embodiment 153 is a dried formulation for the detection of at least one of *Bordetella pertussis* (Bp) nucleic acid and *Bordetella parapertussis* (Bpp) nucleic acid, wherein the dried formulation comprises:

a. a composition as in any one of embodiments 119 to 124, and b. a bulking agent.

Embodiment 154 is a dried formulation for the detection of *Bordetella pertussis* (Bp) nucleic acid, wherein the dried formulation comprises:

a. a detection probe oligomer as in embodiment 113 or 114, and b. a bulking agent.

Embodiment 155 is a dried formulation for the detection of *Bordetella parapertussis* (Bpp) nucleic acid, wherein the dried formulation comprises:

a. a detection probe oligomer as in embodiment 115 or 116, and b. a bulking agent.

Embodiment 156 is the dried formulation of any one of embodiments 153 to 155, wherein the bulking agent is selected from the group consisting of trehalose, raffinose, and a combination thereof.

Embodiment 157 is the dried formulation of any one of embodiments 153 to 156, further comprising an inorganic salt, wherein the percent mass of the inorganic salt to the mass of the dried formulation is 0.249% or less.

Embodiment 158 is the dried formulation of any one of embodiments 153 to 157, further comprising a DNA polymerase enzyme.

Embodiment 159 is the dried formulation of any one of embodiments 153 to 158, further comprising a reverse transcriptase enzyme.

Embodiment 160 is the dried formulation of any one of embodiments 153 to 159, further comprising at least one amplification oligomer.

Embodiment 161 is the dried formulation of any one of embodiments 153 to 160, further comprising a surfactant.

Embodiment 162 is the dried formulation of embodiment 161, wherein the surfactant is a non-linear surfactant.

Embodiment 163 is the dried formulation of embodiment 161, wherein the surfactant is selected from the group consisting of a. polyethylene glycol mono [4-(1,1,3,3-tetramethylbutyl) phenyl] ether, b. polysorbate 20, and c. a combination thereof.

Embodiment 164 is the dried formulation of any one of embodiments 153 to 163, wherein the formulation is a lyophilized formulation.

Embodiment 165 is an amplification reaction mixture comprising an aqueous formulation as in any one of embodiments 125 to 132.

Embodiment 166 is an amplification reaction mixture reconstituted with water or an organic buffer from a dried formulation as in any one of embodiments 133 to 141.

Embodiment 167 is the reaction mixture of embodiment 166, wherein the reaction mixture contains an inorganic salt.

Embodiment 168 is the reaction mixture of embodiment 167, wherein the inorganic salt is selected from the group consisting of magnesium, potassium, and sodium.

Embodiment 169 is the reaction mixture of embodiment 167 or 168, wherein the concentration of the inorganic salt is 4 mM or less.

Embodiment 170 is a detection reaction mixture comprising an aqueous formulation as in any one of embodiments 142 to 152.

Embodiment 171 is a detection reaction mixture reconstituted with water or an organic buffer from a dried formulation as in any one of embodiments 152 to 164.

Embodiment 172 is the reaction mixture of embodiment 171, wherein the reaction mixture contains an inorganic salt.

Embodiment 173 is the reaction mixture of embodiment 172, wherein the inorganic salt is selected from the group consisting of magnesium, potassium, and sodium.

Embodiment 174 is the reaction mixture of embodiment 172 or 173, wherein the concentration of the inorganic salt is 4 mM or less.

These and other aspects of the invention will become evident upon reference to the following detailed description of the invention and the attached drawings.

DEFINITIONS

Unless defined otherwise, all technical and scientific terms used herein have the same meaning as commonly understood by one of ordinary skill in the art pertinent to the methods and compositions described. General definitions may be found in technical books relevant to the art of molecular biology, e.g., Dictionary of Microbiology and Molecular Biology, 2nd ed. (Singleton et al., 1994, John Wiley & Sons, New York, NY) or The Harper Collins Dictionary of Biology (Hale & Marham, 1991, Harper Perennial, New York, NY). As used herein, the following terms and phrases have the meanings ascribed to them unless specified otherwise.

The terms “a,” “an,” and “the” include plural referents, unless the context clearly indicates otherwise. For example, “a nucleic acid” as used herein is understood to represent one or more nucleic acids. As such, the terms “a” (or “an”), “one or more,” and “at least one” can be used interchangeably herein.

It will be appreciated that there is an implied “about” prior to the temperatures, concentrations, times, etc. discussed in the present disclosure, such that slight and insubstantial deviations are within the scope of the present teachings herein. In general, the term “about” indicates insubstantial variation in a quantity of a component of a composition not having any significant effect on the activity or stability of the composition. All ranges are to be interpreted as encompassing the endpoints in the absence of express exclusions such as "not including the endpoints"; thus, for example, "within 10-15" includes the values 10 and 15 as well as all integer and (where possible) non-integer values between the endpoints, e.g., 11, 11.5, 12 and one third, 4×, etc. Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

The conjunction "or" is to be interpreted in the inclusive sense, i.e., as equivalent to "and/or," unless the inclusive sense would be unreasonable in the context.

The term "about" indicates insubstantial variation in a quantity of a component of a composition not having any significant effect on the activity or stability of the composition. In some embodiments, "about" encompasses variation within 10%, 5%, 2%, 1%, or 0.5% of a stated value.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). "Consisting essentially of" means that additional component(s), composition(s) or method step(s) that do not materially change the basic and novel characteristics of the compositions and methods described herein may be included in those compositions or methods. Such characteristics include the ability to detect a *Bordetella pertussis* and/or *Bordetella parapertussis* nucleic acid sequence present in a sample with specificity that distinguishes the *B. pertussis* or *B. parapertussis* nucleic acid from other known pathogens, optionally at a sensitivity that can detect the bacterium present in a sample at a concentration of about 100 CFU/ml, and, optionally within about 60 minutes and/or within about 40 cycles from the beginning of an amplification reaction when a cycled amplification reaction is used.

"Sample" includes any specimen that may contain *Bordetella pertussis* and/or *Bordetella parapertussis* or components thereof, such as nucleic acids or fragments of nucleic acids. Samples include "biological samples" which include any tissue or material derived from a living or dead human that may contain *B. pertussis* and/or *B. parapertussis* or target nucleic acid derived therefrom, including, e.g., vaginal swab samples, cervical brush samples, respiratory tissue or exudates such as bronchoscopy, bronchoalveolar lavage (BAL) or lung biopsy, sputum, saliva, peripheral blood, plasma, serum, lymph node, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" and "polynucleotide" refer to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT Publication No. WO 95/32305), phosphorothioate linkages, methylphosphonate linkages, or combinations thereof. Sugar moieties of a nucleic acid may be ribose, deoxyribose, or similar compounds with substitutions, e.g., 2' methoxy or 2' halide substitutions. Nitrogenous bases may be conventional bases (A, G, C, T, U), analogs thereof (e.g., inosine or others; see *The Biochemistry of the Nucleic Acids* 5-36, Adams et al., ed., $11^{th}$ ed., 1992), derivatives of purines or pyrimidines (e.g., $N^4$-methyl deoxyguanosine, deaza- or aza-purines, deaza- or aza-pyrimidines, pyrimidine bases with substituent groups at the 5 or 6 position, purine bases with a substituent at the 2, 6, or 8 positions, 2-amino-6-methylaminopurine, 06 methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT Publication No. WO 93/13121). Nucleic acids may include one or more "abasic" residues where the backbone includes no nitrogenous base for position(s) of the polymer (U.S. Pat. No. 5,585,481). A nucleic acid may comprise only conventional RNA or DNA sugars, bases and linkages, or may include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43 (42): 13233-41). Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates). 5-methylcytosines may be used in conjunction with any of the foregoing backbones/sugars/linkages including RNA or DNA backbones (or mixtures thereof) unless otherwise indicated. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24, and 25).

A "nucleotide" as used herein is a subunit of a nucleic acid consisting of a phosphate group, a 5-carbon sugar, and a nitrogenous base (also referred to herein as "nucleobase"). The 5-carbon sugar found in RNA is ribose. In DNA, the 5-carbon sugar is 2'-deoxyribose. The term also includes analogs of such subunits, such as a methoxy group at the 2' position of the ribose (also referred to herein as "2'-O-Me" or "2'-methoxy").

By "RNA and DNA equivalents" is meant RNA and DNA molecules having essentially the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence. By "DNA/RNA chimeric" is meant a nucleic acid comprising both DNA and RNA nucleotides. Unless the context clearly dictates otherwise, reference to a *Bordetella pertussis* or *Bordetella parapertussis* nucleic acid includes *B. pertussis* or *B. parapertussis* RNA and DNA equivalents and DNA/RNA chimerics thereof.

A "target nucleic acid" as used herein is a nucleic acid comprising a target sequence to be amplified. Target nucleic acids may be DNA or RNA and may be either single-stranded or double-stranded. The target nucleic acid may include other sequences besides the target sequence, which may not be amplified.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., PCR, TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands.

"Target-hybridizing sequence" or "target-specific sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species. It is understood that other reasons exist for configuring a target-hybridizing sequence to have less than 100% complementarity to a target nucleic acid.

The term "target a sequence," as used herein in reference to a region of *Bordetella pertussis* or *Bordetella parapertussis* nucleic acid, refers to a process whereby an oligonucleotide hybridizes to a target sequence in a manner that allows for amplification and detection as described herein. In one preferred embodiment, the oligonucleotide is complementary with the targeted *B. pertussis* or *B. parapertussis* nucleic acid sequence and contains no mismatches. In another preferred embodiment, the oligonucleotide is complementary but contains 1, 2, 3, 4, or 5 mismatches with the targeted *B. pertussis* or *B. parapertussis* nucleic acid sequence. Preferably, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also, as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced *Bordetella pertussis* or *Bordetella parapertussis* target region. Such an oligonucleotide is not limited to targeting that sequence only, but is rather useful as a composition, in a kit, or in a method for targeting a *B. pertussis* or *B. parapertussis* target nucleic acid. The oligonucleotide is designed to function as a component of an assay for amplification and detection of *B. pertussis* or *B. parapertussis* from a sample, and therefore is designed to target *B. pertussis* or *B. parapertussis* in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion. Similarly, and also as example only, when the nucleic acid is a *Bordetella pertussis* or *Bordetella parapertussis* target nucleic acid, the term "region" may be used to refer to a smaller area of the nucleic acid, wherein the smaller area is targeted by one or more oligonucleotides of the present disclosure. As another non-limiting example, when the nucleic acid in reference is an amplicon, the term region may be used to refer to the smaller nucleotide sequence identified for hybridization by the target-hybridizing sequence of a probe.

"Oligomer," "oligonucleotide," or "oligo" refers to a nucleic acid of generally less than 1,000 nucleotides (nt), including those in a size range having a lower limit of about 2 to 5 nt and an upper limit of about 500 to 900 nt. Some particular embodiments are oligomers in a size range with a lower limit of about 5 to 15, 16, 17, 18, 19, or 20 nt and an upper limit of about 50 to 600 nt, and other particular embodiments are in a size range with a lower limit of about 10 to 20 nt and an upper limit of about 22 to 100 nt. Oligomers may be purified from naturally occurring sources, but may be synthesized by using any well-known enzymatic or chemical method. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound). Oligomers may be referred to by a functional name (e.g., capture probe, primer or promoter primer) but those skilled in the art will understand that such terms refer to oligomers.

As used herein, an oligonucleotide “substantially corresponding to” a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that “substantially corresponding oligonucleotides” can vary from a reference sequence and still hybridize to the same target nucleic acid sequence. It is also understood that a first nucleic acid corresponding to a second nucleic acid includes the RNA or DNA equivalent thereof as well as DNA/RNA chimerics thereof, and includes the complements thereof, unless the context clearly dictates otherwise. This variation from the nucleic acid may be stated in terms of a percentage of identical bases within the sequence or the percentage of perfectly complementary bases between the probe or primer and its target sequence; thus, in certain embodiments, an oligonucleotide “substantially corresponds” to a reference nucleic acid sequence if these percentages of base identity or complementarity are from 100% to about 80%, preferably from 100% to about 85%, or more preferably from 100% to about 90% or from 100% to about 95%. This variation from the nucleic acid may also be stated in terms of the number of nucleobase substitutions in a nucleic acid sequence relative to a reference sequence, or the number of mismatches within a sequence relative to a target sequence; thus, in certain embodiments, an oligonucleotide “substantially corresponds” to a reference nucleic acid sequence if this number of nucleobase substitutions or mismatches is up to four, preferable up to three, or more preferably up to two or up to one substitution(s) or mismatch(es) (i.e., from zero to four, preferably from zero to three, or more preferably from zero to two or from zero to one, inclusive). Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

As used herein, the phrase “or its complement, or an RNA equivalent or DNA/RNA chimeric thereof,” with reference to a DNA sequence, includes (in addition to the referenced DNA sequence) the complement of the DNA sequence, an RNA equivalent of the referenced DNA sequence, an RNA equivalent of the complement of the referenced DNA sequence, a DNA/RNA chimeric of the referenced DNA sequence, and a DNA/RNA chimeric of the complement of the referenced DNA sequence. Similarly, the phrase “or its complement, or a DNA equivalent or DNA/RNA chimeric thereof,” with reference to an RNA sequence, includes (in addition to the referenced RNA sequence) the complement of the RNA sequence, a DNA equivalent of the referenced RNA sequence, a DNA equivalent of the complement of the referenced RNA sequence, a DNA/RNA chimeric of the referenced RNA sequence, and a DNA/RNA chimeric of the complement of the referenced RNA sequence.

An “amplification oligonucleotide” or “amplification oligomer” is an oligonucleotide that hybridizes to a target nucleic acid, or its complement, and participates in a nucleic acid amplification reaction, e.g., serving as a primer or and promoter-primer. Particular amplification oligomers contain at least about 10 contiguous bases, and optionally at least 11, 12, 13, 14, 15, 16, 17, 18, 19, or 20 contiguous bases, that are complementary to a region of the target nucleic acid sequence or its complementary strand. The contiguous bases may be at least about 80%, at least about 90%, or completely complementary to the target sequence to which the amplification oligomer binds. One skilled in the art will understand that the recited ranges include all whole and rational numbers within the range (e.g., 92% or 98.377%). Particular amplification oligomers are about 10 to about 60 bases long and optionally may include modified nucleotides.

A “primer” is an oligomer that hybridizes to a template nucleic acid and has a 3' hydroxyl that is extended by polymerization. A primer may be optionally modified, e.g., by including a 5' region that is non-complementary to the target sequence. Such modification can include functional additions, such as tags, promoters, or other non-target-specific sequences used or useful for manipulating or amplifying the primer or target oligonucleotide.

Within the context of transcription-mediated amplification, a primer modified with a 5' promoter sequence is referred to herein as a “promoter-primer.” A person of ordinary skill in the art of molecular biology or biochemistry will understand that an oligomer that can function as a primer can be modified to include a 5' promoter sequence and then function as a promoter-primer, and, similarly, any promoter-primer can serve as a primer with or without its 5' promoter sequence. A promoter-primer modified to incorporate a 3' blocked end is referred to herein as a “promoter provider,” which is capable of hybridizing to a target nucleic acid and providing an upstream promoter sequence that serves to initiate transcription, but does not provide a primer for oligo extension.

“Non-target-specific sequence” or “non-target-hybridizing sequence” as used herein refers to a region of an oligomer sequence, wherein said region does not stably hybridize with a target sequence under standard hybridization conditions. Oligomers with non-target-specific sequences include, but are not limited to, promoter primers and molecular beacons.

“Nucleic acid amplification” refers to any in vitro procedure that produces multiple copies of a target nucleic acid sequence, or its complementary sequence, or fragments thereof (i.e., an amplified sequence containing less than the complete target nucleic acid). Examples of nucleic acid amplification procedures include transcription associated methods, such as transcription-mediated amplification (TMA), nucleic acid sequence-based amplification (NASBA) and others (e.g., U.S. Pat. Nos. 5,399,491, 5,554,516, 5,437,990, 5,130,238, 4,868,105, and 5,124,246), replicase-mediated amplification (e.g., U.S. Pat. No. 4,786,600), the polymerase chain reaction (PCR) (e.g., U.S. Pat. Nos. 4,683,195, 4,683,202, and 4,800,159), ligase chain reaction (LCR) (e.g., EP U.S. Pat. No. 320,308), helicase-dependent amplification (e.g., U.S. Pat. No. 7,282,328), and strand-displacement amplification (SDA) (e.g., U.S. Pat. No. 5,422,252). Amplification may be linear or exponential. Replicase-mediated amplification uses self-replicating RNA molecules, and a replicase such as QB-replicase. PCR amplification uses DNA polymerase, primers, and thermal cycling steps to synthesize multiple copies of the two complementary strands of DNA or cDNA. LCR amplification uses at least four separate oligonucleotides to amplify a target and its complementary strand by using multiple cycles of hybridization, ligation, and denaturation. Helicase-dependent amplification uses a helicase to separate the two strands of a DNA duplex generating single-stranded templates, followed by hybridization of sequence-specific primers hybridize to the templates and extension by DNA polymerase to amplify the target sequence. SDA uses a primer that contains a recognition site for a restriction endonuclease that will nick one strand of a hemimodified DNA duplex that includes the target sequence, followed by amplification in a series of primer extension and strand displacement steps. Particular embodiments use PCR or TMA, but it will be apparent to persons of ordinary skill in the art that oligomers disclosed herein may be readily used as primers in other amplification methods.

Transcription associated amplification uses a DNA polymerase, an RNA polymerase, deoxyribonucleoside triphosphates, ribonucleoside triphosphates, a promoter-containing oligonucleotide, and optionally may include other oligonucleotides, to ultimately produce multiple RNA transcripts from a nucleic acid template (described in detail in, e.g., U.S. Pat. Nos. 5,399,491 and 5,554,516 to Kacian et al.; U.S. Pat. No. 5,437,990 to Burg et al.; PCT Publication Nos. WO 88/01302 and WO 88/10315 (Gingeras et al.); U.S. Pat. No. 5,130,238 to Malek et al.; U.S. Pat. Nos. 4,868,105 and 5,124,246 to Urdea et al.; PCT Publication No. WO 94/03472 (McDonough et al.); and PCT Publication No. WO 95/03430 (Ryder et al.)). Methods that use TMA are described in detail previously (e.g., U.S. Pat. Nos. 5,399,491 and 5,554,516).

In cyclic amplification methods that detect amplicons in real-time, the term "Threshold cycle" (Ct) is a measure of the emergence time of a signal associated with amplification of target and is generally 10× standard deviation of the normalized reporter signal. Once an amplification reaches the "threshold cycle," generally there is considered to be a positive amplification product of a sequence to which the probe binds. The identity of the amplification product can then be determined through methods known to one of skill in the art, such as gel electrophoresis, nucleic acid sequencing, and other such analytical procedures.

By "amplicon" or "amplification product" is meant a nucleic acid molecule generated in a nucleic acid amplification reaction and which is derived from a target nucleic acid. An amplicon or amplification product contains a target nucleic acid sequence that may be of the same or opposite sense as the target nucleic acid.

As used herein, the term "relative fluorescence unit" ("RFU") is a unit of measurement of fluorescence intensity. RFU varies with the characteristics of the detection means used for the measurement and can be used as a measurement to compare relative intensities between samples and controls.

"Detection probe oligomer," "detection probe," or "probe" refers to an oligomer that hybridizes specifically to a target sequence, including an amplified sequence, under conditions that promote nucleic acid hybridization, for detection of the target nucleic acid. Detection may either be direct (i.e., probe hybridized directly to the target) or indirect (i.e., a probe hybridized to an intermediate structure that links the probe to the target). Detection probes may be DNA, RNA, analogs thereof or combinations thereof (e.g., DNA/RNA chimerics), and they may be labeled or unlabeled. Detection probes may further include alternative backbone linkages such as, e.g., 2'-O-methyl linkages. A probe's target sequence generally refers to the specific sequence within a larger sequence which the probe hybridizes specifically. A detection probe may include target-specific sequence(s) and non-target-specific sequence(s). Such non-target-specific sequences can include sequences which will confer a desired secondary or tertiary structure, such as a hairpin structure, which can be used to facilitate detection and/or amplification (see, e.g., U.S. Pat. Nos. 5,118,801, 5,312,728, 6,835,542, and 6,849,412). Probes of a defined sequence may be produced by techniques known to those of ordinary skill in the art, such as by chemical synthesis, and by in vitro or in vivo expression from recombinant nucleic acid molecules.

By "hybridization" or "hybridize" is meant the ability of two completely or partially complementary nucleic acid strands to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. See, e.g., R. L. P. Adams et al., *The Biochemistry of the Nucleic Acids* (11th ed. 1992).

By "preferentially hybridize" is meant that under stringent hybridization conditions, an amplification or detection probe oligomer can hybridize to its target nucleic acid to form stable oligomer:target hybrid, but not form a sufficient number of stable oligomer: non-target hybrids. Amplification and detection oligomers that preferentially hybridize to a target nucleic acid are useful to amplify and detect target nucleic acids, but not non-targeted organisms, especially phylogenetically closely related organisms. Thus, the oligomer hybridizes to target nucleic acid to a sufficiently greater extent than to non-target nucleic acid to enable one having ordinary skill in the art to accurately amplify and/or detect the presence (or absence) of nucleic acid derived from the specified target as appropriate. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. In some embodiments, there is at least a 10-fold difference between target and non-target hybridization signals in a test sample, at least a 100-fold difference, or at least a 1,000-fold difference. In some embodiments, non-target hybridization signals in a test sample are no more than the background signal level.

By "stringent hybridization conditions," or "stringent conditions" is meant conditions permitting an oligomer to preferentially hybridize to a target nucleic acid and not to nucleic acid derived from a closely related non-target nucleic acid. While the definition of stringent hybridization conditions does not vary, the actual reaction environment that can be used for stringent hybridization may vary depending upon factors including the GC content and length of the oligomer, the degree of similarity between the oligomer sequence and sequences of non-target nucleic acids that may be present in the test sample, and the target sequence. Hybridization conditions include the temperature and the composition of the hybridization reagents or solutions. Exemplary hybridization assay conditions for amplifying and/or detecting target nucleic acids derived from *Bordetella pertussis* or *Bordetella parapertussis* with the oligomers of the present disclosure correspond to a temperature of about 60° C. when the salt concentration, such as a monovalent salt, e.g., KCl, is in the range of about 0.6-0.9 M. Other acceptable stringent hybridization conditions are readily ascertained by those having ordinary skill in the art.

By "assay conditions" is meant conditions permitting stable hybridization of an oligonucleotide to a target nucleic acid. Assay conditions do not require preferential hybridization of the oligonucleotide to the target nucleic acid.

"Label" or "detectable label" refers to a moiety or compound joined directly or indirectly to a probe that is detected or leads to a detectable signal. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal. Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g., bioluminescent, phosphorescent, or chemiluminescent compound), and fluorescent compound (i.e., fluorophore). Embodiments of fluorophores include those that absorb light in the range of about 495 to 650 nm and emit light in the range of about 520 to 670 nm, which include those known as FAM™, TET™, CAL FLUOR™ (Orange or Red), and QUASAR™ compounds. Fluorophores may be used in combination with a quencher molecule that absorbs light when in close proximity to the fluorophore to diminish background fluorescence. Such quenchers are well known in the art and include, e.g., BLACK HOLE QUENCHER™ (or BHQ™) or TAMRA™ compounds. Particular embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 5,283,174, 5,656,207, and 5,658,737). Particular homogeneous detectable labels include chemiluminescent compounds, including acridinium ester ("AE") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are well known (e.g., Sambrook et al., *Molecular Cloning, A Laboratory Manual,* 2nd ed. (Cold Spring Harbor Laboratory Press, Cold Spring Harbor, NY, 1989) at Chapt. 10, and U.S. Pat. Nos. 5,658,737, 5,656,207, 5,547,842, 5,283,174, and 4,581,333, and EP Pat. App. 0 747 706). Particular methods of linking an AE compound to a nucleic acid are known (e.g., U.S. Pat. Nos. 5,585,481 and 5,639,604, see column 10, line 6 to column 11, line 3, and Example 8). Particular AE labeling positions are a probe's central region and near a region of A/T base pairs, at a probe's 3' or 5' terminus, or at or near a mismatch site with a known sequence that is the probe should not detect compared to the desired target sequence. Other detectably labeled probes include TaqMan™ probes, molecular torches, and molecular beacons. TaqMan™ probes include a donor and acceptor label wherein fluorescence is detected upon enzymatically degrading the probe during amplification in order to release the fluorophore from the presence of the quencher. Molecular torches and beacons exist in open and closed configurations wherein the closed configuration quenches the fluorophore and the open position separates the fluorophore from the quencher to allow fluorescence. Hybridization to target opens the otherwise closed probes.

Sequences are "sufficiently complementary" if they allow stable hybridization of two nucleic acid sequences, e.g., stable hybrids of probe and target sequences, although the sequences need not be completely complementary. That is, a "sufficiently complementary" sequence that hybridizes to another sequence by hydrogen bonding between a subset series of complementary nucleotides by using standard base pairing (e.g., G:C, A:T, or A:U), although the two sequences may contain one or more residues (including abasic positions) that are not complementary so long as the entire sequences in appropriate hybridization conditions to form a stable hybridization complex. Sufficiently complementary sequences may be at least about 80%, at least about 90%, or completely complementary in the sequences that hybridize together. Appropriate hybridization conditions are well-known to those skilled in the art, can be predicted based on sequence composition, or can be determined empirically by using routine testing (e.g., Sambrook et al., *Molecular Cloning, A Laboratory Manual,* $2^{nd}$ ed. at §§ 1.90-1.91, 7.37-7.57, 9.47-9.51 and 11.47-11.57, particularly §§ 9.50-9.51, 11.12-11.13, 11.45-11.47 and 11.55-11.57).

A "non-extendable" oligomer includes a blocking moiety at or near its 3'-terminus to prevent extension. A blocking group near the 3' end is in some embodiments within five residues of the 3' end and is sufficiently large to limit binding of a polymerase to the oligomer, and other embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin. Further examples of blocking moieties include a 3'-deoxy nucleotide (e.g., a 2',3'-dideoxy nucleotide); a 3'-phosphorylated nucleotide; a fluorophore, quencher, or other label that interferes with extension; an inverted nucleotide (e.g., linked to the preceding nucleotide through a 3'-to-3' phosphodiester, optionally with an exposed 5'-OH or phosphate); or a protein or peptide joined to the oligonucleotide so as to prevent further extension of a nascent nucleic acid chain by a polymerase. A non-extendable oligonucleotide of the present disclosure may be at least 10 bases in length, and may be up to 15, 20, 25, 30, 35, 40, 50 or more nucleotides in length. Non-extendable oligonucleotides that comprise a detectable label can be used as probes.

References, particularly in the claims, to "the sequence of SEQ ID NO: X" refer to the base sequence of the corresponding sequence listing entry and do not require identity of the backbone (e.g., RNA, 2'-O-Me RNA, or DNA) or base modifications (e.g., methylation of cytosine residues) unless the context clearly dictates otherwise.

"Sample preparation" refers to any steps or method that treats a sample for subsequent amplification and/or detection of *Bordetella pertussis* and/or *Bordetella parapertussis* nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. "Separating" or "purifying" does not connote any degree of purification. Typically, separating or purifying removes at least 70%, or at least 80%, or at least 95% of the target nucleic acid from other sample components.

The term "non-linear surfactant," as used herein, means a surfactant having a branched chain structure. A non-linear surfactant may include one or more ring structures, which may be, for example, in a principal chain and/or in one or more branch chains. Exemplary non-linear surfactants include polysorbate 20, polysorbate 40, polysorbate 60, and digitonin. In certain variations, a non-linear surfactant is non-ionic.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

The term "kit" is used herein to refer to a packaged combination of reagents, including, e.g., one or more oligomers disclosed herein. For example, a kit can include a packaged combination of one or more vials, tubes, or cartridges having a plurality of chambers containing reagents suitable for methods described herein. The reagents can include oligonucleotide primers and probes such as those described herein, as well as nucleotide polymerizing enzymes (e.g., a DNA polymerase, a reverse transcriptase, an RNA polymerase, etc.). In certain embodiments, the reagents can be in liquid form, in solid form (e.g., a lyophilisate), or a semi-solid form (e.g., a glass). In some embodiments, oligonucleotide reagents and enzyme reagents are present in the kit as components of a single lyophilized composition (e.g., a pellet). In such an instance, primers, probes, and one or more enzymes (e.g., a nucleotide polymerizing enzyme) can be disposed in the same reaction chamber or vessel in a lyophilized form that can be reconstituted with an aqueous reagent, where a separate vial or tube containing the aqueous reagent is included in the same kit. The kits may further include a number of optional components such as, for example, other oligomers. Other reagents that may be present in the kits include reagents suitable for performing in vitro amplification such as buffers, salt solutions, and/or appropriate nucleotide triphosphates (e.g., dATP, dCTP, dGTP, dTTP; and/or ATP, CTP, GTP and UTP). Kits further can include a solid support material (e.g., magnetically attractable particles, e.g., magnetic beads) for immobilizing the oligomers, either directly or indirectly, in a sample-preparation procedure. In certain embodiments, the kit further includes a set of instructions for practicing methods in accordance with the present disclosure, where the instructions may be associated with a package insert and/or the packaging of the kit or the components thereof.

DETAILED DESCRIPTION

The present invention provides compositions, kits, and methods for amplifying and detecting *Bordetella pertussis* and/or *Bordetella parapertussis* nucleic acid from a sample. Preferably, the samples are biological samples. The compositions, kits, and methods provide oligonucleotide sequences that recognize target the IS481 and IS1001 gene sequences of *B. pertussis* and *B. parapertussis*, respectively, or their complementary sequences. Such oligonucleotides may be used as amplification oligonucleotides, which may include primers, promoter primers, blocked oligonucleotides, and promoter provider oligonucleotides, whose functions have been described previously (see, e.g., U.S. Pat. Nos. 4,683,195; 4,683,202; 4,800,159; 5,399,491; 5,554,516; 5,824,518; and 7,374,885; each incorporated by reference herein). Other oligonucleotides may be used as probes for detecting amplified sequences of *B. pertussis* or *B. parapertussis*, or for capture of *B. pertussis* or *B. parapertussis* target nucleic acid.

The methods provide for the sensitive and specific detection of *B. pertussis* and/or *B. parapertussis* nucleic acids. The methods include performing a nucleic acid amplification of a *B. pertussis* target region and/or a *B. parapertussis* target region and detecting the amplified product by, for example, specifically hybridizing the amplified product with a nucleic acid detection probe that provides a signal to indicate the presence of *B. pertussis* and/or *B. parapertussis* in the sample. The amplification step includes contacting the sample with one or more amplification oligomers specific for a target sequence in a *B. pertussis* and/or *B. parapertussis* target nucleic acid to produce an amplified product if *B. pertussis* or *B. parapertussis* nucleic acid is present in the sample. Amplification synthesizes additional copies of the target sequence or its complement by using at least one nucleic acid polymerase and an amplification oligomer to produce the copies from a template strand (e.g., by extending the sequence from a primer using the template strand). One embodiment for detecting the amplified product uses a hybridizing step that includes contacting the amplified product with at least one detection probe oligomer specific for a sequence amplified by the selected amplification oligomers, e.g., a sequence contained in the target sequence flanked by a pair of selected amplification oligomers.

In some aspects, the compositions of the instant invention are configured to specifically hybridize to *Bordetella pertussis* or *Bordetella parapertussis* nucleic acid with minimal cross-reactivity to one or more non-Bp or non-Bpp pathogens. In some embodiments, the compositions of the instant invention are configured to specifically hybridize to *B. pertussis* or *B. parapertussis* nucleic acid with minimal cross-reactivity to one or more non-*Bordetella* pathogens listed in Table 19 (see Example 7, infra). In other, non-mutually exclusive embodiments, the compositions of the instant invention are configured to specifically hybridize to *B. pertussis* or *B. parapertussis* nucleic acid with minimal cross-reactivity to one or more non-Bp or non-Bpp *Bordetella* pathogens. In one aspect, the compositions of the instant invention are part of a multiplex system that further includes components and methods for detecting one of more of these non-Bp or non-Bpp pathogens.

In certain aspects of the invention, a composition comprising at least two amplification oligomers is provided for determining the presence or absence of *Bordetella pertussis* and/or *Bordetella parapertussis* in a sample. In some embodiments, the composition includes at least two amplification oligomers for amplifying a target region of a Bp target nucleic acid corresponding to the sequence of SEQ ID NO:1. In other, non-mutually exclusive embodiments, the composition includes at least two amplification oligomers for amplifying a target region of a Bpp target nucleic acid corresponding to the sequence of SEQ ID NO:2. In such embodiments, at least one amplification oligomer comprises a target-hybridizing sequence in the sense orientation ("sense THS") and at least one amplification oligomer comprises a target-hybridizing sequence in the antisense orientation ("antisense THS"), where the sense THS and antisense THS are each configured to specifically hybridize to a Bp or Bpp target sequence corresponding to a sequence contained within SEQ ID NO:1 or SEQ ID NO:2, respectively, and where the target-hybridizing sequences are selected such that the Bp or Bpp sequence targeted by antisense THS is situated downstream of the Bp or Bpp sequence targeted by the sense THS (i.e., the at least two amplification oligomers are situated such that they flank the target region to be amplified).

In some variations, a composition includes (i) a *Bordetella pertussis* (Bp)-specific amplification oligomer comprising a Bp-specific target-hybridizing sequence substantially corresponding to, or identical to, the sequence shown in SEQ ID NO:3, SEQ ID NO: 5, SEQ ID NO:6, SEQ ID NO:8, SEQ ID NO:9, SEQ ID NO: 11, SEQ ID NO: 12, SEQ ID NO: 14, SEQ ID NO:15, SEQ ID NO: 17, SEQ ID NO: 18, SEQ ID NO:20, SEQ ID NO:21, SEQ ID NO:23, SEQ ID NO:24, SEQ ID NO:26, SEQ ID NO:27, SEQ ID NO:29, SEQ ID NO: 45, or SEQ ID NO:46, or an RNA equivalent or DNA/RNA chimeric thereof. In some variations, a composition includes (ii) a *Bordetella parapertussis* (Bpp)-specific amplification oligomer comprising a Bpp-specific target-hybridizing sequence substantially corresponding to, or identical to, the sequence shown in SEQ ID NO:30, SEQ ID NO:32, SEQ ID NO:33, SEQ ID NO:35, SEQ ID NO:36, SEQ ID NO:38, SEQ ID NO:39, SEQ ID NO:41, SEQ ID NO: 42, or SEQ ID NO:44, or an RNA equivalent or DNA/RNA chimeric thereof. In variations comprising a Bp-specific or Bpp-specific amplification oligomer of (i) or (ii) as above, the oligomer combination includes at least one an amplification oligomer comprising an Bp-specific or Bpp-specific target-hybridizing sequence of the opposite polarity (sense vs. antisense or vice versa) as the target-hybridizing sequence of the oligomer of (i) or (ii), such that at least two amplification oligomers flank a target region to be amplified. In certain embodiments, the composition is provided as an aqueous or dried formulation for amplification of Bp and/or Bpp nucleic acid, or a reaction mixture comprising or reconstituted from such a formulation.

In more specific embodiments of the present invention, a composition for determining the presence or absence of *Bordetella pertussis* or *Bordetella parapertussis* in a sample includes (1) at least one amplification oligomer comprising a Bp-specific or Bpp-specific target-hybridizing region substantially corresponding to at least one sense oligomer sequence depicted in Table 1 below, and (2) at least one amplification oligomer comprising a Bp-specific or Bpp-specific target hybridizing region substantially corresponding to at least one antisense oligomer sequence depicted in Table 1. In some such embodiments, the composition includes a first Bp-specific amplification oligomer and a first Bpp-specific amplification oligomer of (1) above and a second Bp-specific and second Bpp-specific amplification oligomer of (2) above. In particular variations, the sense and/or antisense target-hybridizing sequence(s) of an amplification oligomer combination comprises or consists of the sense and/or antisense sequence(s) selected from Table 1.

TABLE 1

Exemplary Sense and Antisense Amplification Oligomer Target-hybridizing Sequences for Amplification of *B. pertussis* or *B. parapertussis* Target Regions

| SEQ ID NO | Sequence (5' → 3') | Sense/ Anti-sense[1] | Target Pathogen/ Gene |
|---|---|---|---|
| 3 | TTGCGTGAGTGGGCTTA | Sense | Bp/IS481 |
| 5 | ATGCCAGTTGTAGTGGTGTA | Antisense | Bp/IS481 |
| 6 | CCTTGCGTGAGTGGGCTTAC | Sense | Bp/IS481 |
| 8 | GTGGGGTCGATGCCAGTTGT | Antisense | Bp/IS481 |
| 9 | TTACGCTCACACCTACCA | Sense | Bp/IS481 |
| 11 | AGTCTGGAGATGGGTACAG | Antisense | Bp/IS481 |
| 12 | CCGATGCCATGAAATCCT | Sense | Bp/IS481 |
| 14 | GTATTCGTCCAGGTTGAGTC | Antisense | Bp/IS481 |
| 15 | CACATATATCGCCGACAGC | Sense | Bp/IS481 |
| 17 | CGCCACCTTGAAGTCATT | Antisense | Bp/IS481 |
| 18 | CCGAACCGGATTTGAGAAAC | Sense | Bp/IS481 |
| 20 | TAGGAAGGTCAATCGGGCAT | Antisense | Bp/IS481 |
| 21 | GATTCAATAGGTTGTATGCATGGTT | Sense | Bp/IS481 |
| 23 | TTCAGGCACACAAACTTGATGGGCG | Antisense | Bp/IS481 |
| 24 | ATCGGGCATGCTTATGGGTGTTCA | Antisense | Bp/IS481 |
| 26 | GCGGGCTAACTGTGAAGATTCAATAG | Sense | Bp/IS481 |
| 27 | GATTCAATAGGTTGTATGCATGG | Sense | Bp/IS481 |
| 29 | TTCAGGCACACAAACTTGATGG | Antisense | Bp/IS481 |
| 30 | GAGATCGTCTATGACTTGTTCC | Sense | Bpp/IS1001 |
| 32 | ACGATCCTGGCGTAGTT | Antisense | Bpp/IS1001 |
| 33 | TTCGAGTATCGGGTCGTT | Sense | Bpp/IS1001 |
| 35 | ATCCGTCACCCGTTGATA | Antisense | Bpp/IS1001 |
| 36 | CACCGCCTACGAGTTCGAGAT | Sense | Bpp/IS1001 |
| 38 | CCTCGACAATGCTGGTGTTCA | Antisense | Bpp/IS1001 |
| 39 | CCATGTCGTGGCCAAGTATG | Sense | Bpp/IS1001 |
| 41 | GCTGGTTGGCTTGCAGCAAT | Antisense | Bpp/IS1001 |
| 42 | TCAAGACGCTGGACAAGGCT | Sense | Bpp/IS1001 |
| 44 | GCAGGGCAAACTCGTCCATC | Antisense | Bpp/IS1001 |

TABLE 1-continued

Exemplary Sense and Antisense Amplification Oligomer Target-hybridizing Sequences for Amplification of *B. pertussis* or *B. parapertussis* Target Regions

| SEQ ID NO | Sequence (5' → 3') | Sense/ Anti-sense[1] | Target Pathogen/ Gene |
|---|---|---|---|
| 45 | CTTACGCTCACACCTACCA | Sense | Bp/IS481 |
| 46 | CGATGCCAGTTGTAGTGGT | Antisense | Bp/IS481 |

[1]The Sense/Antisense designation of these sequences is for exemplary purposes only. Such designation does not necessarily limit a sequence to the accompanying designation.

In certain variations, a composition for determining the presence or absence of *Bordetella pertussis* and/or *Bordetella parapertussis* in a sample as described herein further comprises at least one detection probe oligomer configured to specifically hybridize to a Bp or Bpp target sequence that is amplifiable using the first and second amplification oligomers (e.g., a Bp or Bpp target sequence contained within SEQ ID NO:1 or SEQ ID NO:2, or the complement thereof, that is flanked by the target-hybridizing sequences of the first and second amplification oligomers). Particularly suitable Bp-specific detection probe oligomers include, for example, oligomers comprising a Bp-specific target-hybridizing sequence substantially corresponding to, or identical to, the sequence shown in SEQ ID NO:4, SEQ ID NO: 7, SEQ ID NO:10, SEQ ID NO:13, SEQ ID NO:16, SEQ ID NO: 19, SEQ ID NO:22, SEQ ID NO:25 or SEQ ID NO:28, or the complement thereof or an RNA equivalent or DNA/RNA chimeric thereof. Particularly suitable Bpp-specific detection probe oligomers include, for example, oligomers comprising a Bpp-specific target-hybridizing sequence substantially corresponding to, or identical to, the sequence shown in SEQ ID NO:31, SEQ ID NO: 34, SEQ ID NO:37, SEQ ID NO:40, or SEQ ID NO:43, or the complement thereof or an RNA equivalent or DNA/RNA chimeric thereof. A detection probe oligomer may contain a 2'-methoxy backbone at one or more linkages in the nucleic acid backbone. In some variations, a composition includes at least two detection probe oligomers. In certain embodiments, a detection probe oligomer is provided in an aqueous or dried formulation for detection of Bp and/or Bpp nucleic acid, or a reaction mixture comprising or reconstituted from such a formulation.

Table 2 shows exemplary combinations of detection probe target hybridizing sequences together with first and second amplification oligomer target-hybridizing sequences ("Amp 1" and "Amp 2") for detection of *B. pertussis* or *B. parapertussis*.

TABLE 2

Exemplary Combinations of Amplification Oligomer and Detection Probe Target-hybridizing Sequences

| Amplification Oligomer THSs | | Detection Probe |
|---|---|---|
| Amp 1 (SEQ ID NO) | Amp 2 (SEQ ID NO) | THS (SEQ ID NO) |
| 3 | 5 | 4 |
| 6 | 8 | 7 |
| 9 | 11 | 10 |
| 12 | 14 | 13 |

TABLE 2-continued

Exemplary Combinations of Amplification Oligomer and Detection Probe Target-hybridizing Sequences

| Amplification Oligomer THSs | | Detection Probe |
|---|---|---|
| Amp 1 (SEQ ID NO) | Amp 2 (SEQ ID NO) | THS (SEQ ID NO) |
| 15 | 17 | 16 |
| 18 | 20 | 19 |
| 21 | 23 | 22 |
| 24 | 26 | 25 |
| 27 | 29 | 28 |
| 30 | 32 | 31 |
| 33 | 35 | 34 |
| 36 | 38 | 37 |
| 39 | 41 | 40 |
| 42 | 44 | 43 |
| 45 | 46 | 4 |

Typically, a detection probe oligomer in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein). A label, such as, e.g., a fluorescent or chemiluminescent label, is typically attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein).

In some embodiments, a probe (e.g., comprising a fluorescent label) further includes a second label that interacts with the first label. For example, the second label can be a quencher. Detection probes comprising both a fluorescent label and a quencher, a combination are particularly useful in fluorescence resonance energy transfer (FRET) assays. Specific variations of such detection probes include, e.g., a TaqMan™ detection probe (Roche Molecular Diagnostics) and a "molecular beacon" (see, e.g., Tyagi et al., Nature Biotechnol. 16:49-53, 1998; U.S. Pat. Nos. 5,118,801 and 5,312,728; each incorporated by reference herein). TaqMan™ probes (or similar dual-labeled linear probes comprising both a fluorescent label and a quencher), can be used in assays where hybridization of the probe to a target or amplicon followed by nucleolysis by a polymerase comprising 5'-3' exonuclease activity results in liberation of the fluorescent label and thereby increased fluorescence, or fluorescence independent of the interaction with the second label.

In some applications, a detection probe exhibiting at least some degree of self-complementarity are used to facilitate detection of probe:target duplexes in a test sample without first requiring the removal of unhybridized probe prior to detection. Specific embodiments of such detection probes include, for example, probes that form conformations held by intramolecular hybridization, such as conformations generally referred to as hairpins. Suitable hairpin probes include a "molecular torch" (see, e.g., U.S. Pat. Nos. 6,849,412; 6,835,542; 6,534,274; and 6,361,945) and a "molecular beacon" (see, e.g., U.S. Pat. Nos. 5,118,801 and 5,312,728). Molecular torches include distinct regions of self-complementarity (coined "the target binding domain" and "the target closing domain") which are connected by a joining region (e.g., a $-(CH_2CH_2O)_3-$ linker) and which hybridize to one another under predetermined hybridization assay conditions. When exposed to an appropriate target or denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith.

In other embodiments, a detection probe is a linear oligomer that does not substantially form conformations held by intramolecular bonds. In specific variations, a linear detection probe oligomer includes a chemiluminescent compound as the label (e.g., an acridinium ester (AE) compound). In other embodiments, a linear detection probe oligomer includes a fluorophore as the label. In some embodiments of a linear detection probe oligomer comprising a fluorophore, the oligomer further includes a quenching moiety (e.g., a TaqMan probe).

Examples of interacting donor/acceptor label pairs that may be used in connection with the disclosure, making no attempt to distinguish FRET from non-FRET pairs, include fluorescein/tetramethylrhodamine, IAEDANS/fluorescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. Non-fluorescent acceptors such as DABCYL and the QSY7 dyes advantageously eliminate the potential problem of background fluorescence resulting from direct (i.e., non-sensitized) acceptor excitation. Exemplary fluorophore moieties that can be used as one member of a donor-acceptor pair include fluorescein, ROX, and the CY dyes (such as CY5). Exemplary quencher moieties that can be used as another member of a donor-acceptor pair include DABCYL and the BLACK HOLE QUENCHER moieties which are available from Biosearch Technologies, Inc., (Novato, Calif.).

In some embodiments, a labeled oligomer (e.g., a detection probe) is non-extendable. For example, the labeled oligomer can be rendered non-extendable by 3'-phosphorylation, having a 3'-terminal 3'-deoxynucleotide (e.g., a terminal 2',3'-dideoxynucleotide), having a 3'-terminal inverted nucleotide (e.g., in which the last nucleotide is inverted such that it is joined to the penultimate nucleotide by a 3' to 3' phosphodiester linkage or analog thereof, such as a phosphorothioate), or having an attached fluorophore, quencher, or other label that interferes with extension (possibly but not necessarily attached via the 3' position of the terminal nucleotide). In some embodiments, the 3'-terminal nucleotide is not methylated.

Also provided by the present invention are compositions comprising one or more detection probe oligomers as described herein.

In some aspects, the present invention provides methods utilizing an oligomer or oligomer combination as described herein. Any method disclosed herein is also to be understood as a disclosure of corresponding uses of materials involved in the method directed to the purpose of the method. Any of the oligomers comprising a *Bordetella pertussis* or *Bordetella parapertussis* target-hybridizing sequence and any combinations (e.g., kits and compositions) comprising such an oligomer are to be understood as also disclosed for use in detecting or quantifying Bp and/or Bpp, and for use in the preparation of a composition for detecting or quantifying Bp and/or Bpp.

Broadly speaking, methods may comprise one or more of the following components: target capture, in which Bp or Bpp nucleic acid (e.g., from a sample, such as a clinical sample) is annealed to a capture oligomer; isolation, e.g., washing, to remove material not associated with a capture oligomer; amplification; and amplicon detection, e.g., amplicon quantification, which may be performed in real time with amplification. Certain embodiments involve each of the foregoing steps. Certain embodiments involve exponential amplification, optionally with a preceding linear amplification step. Certain embodiments involve exponential amplification and amplicon detection. Certain embodiments involve any two of the components listed above. Certain embodiments involve any two components listed adjacently above, e.g., washing and amplification, or amplification and detection.

In some embodiments, the present invention provides a method for determining the presence or absence of *Bordetella pertussis* and/or *Bordetella parapertussis* in a sample using an oligomer combination as described herein. Such a method generally includes (1) contacting the sample with at least two amplification oligomers for amplifying a Bp and/or Bpp nucleic acid target region corresponding to a Bp and/or Bpp target nucleic acid, where the at least two amplification oligomers are as described above; (2) performing an in vitro nucleic acid amplification reaction, where any Bp and/or Bpp target nucleic acid present in the sample is used as a template for generating an amplification product; and (3) detecting the presence or absence of the amplification product, thereby determining the presence or absence of Bp and/or Bpp in the sample. A detection method in accordance with the present invention typically further includes the step of obtaining the sample to be contacted with the at least two amplification oligomers. In certain embodiments, "obtaining" a sample to be used in steps (1)-(3) includes, for example, receiving the sample at a testing facility or other location where one or more steps of the method are performed, and/or retrieving the sample from a location (e.g., from storage or other depository) within a facility where one or more steps of the method are performed.

Amplifying a *Bordetella pertussis* and/or *Bordetella parapertussis* target sequence utilizes an in vitro amplification reaction using at least two amplification oligomers that flank a target region to be amplified. In particular embodiments, the target region to be amplified is a Bp target region substantially corresponding to SEQ ID NO: 1 from about nucleotide position 2471 to about nucleotide position 2622, or substantially corresponding to a region contained therein (e.g., a target region from about nucleotide position 2473 to about nucleotide position 2562, or from about nucleotide position 2487 to about nucleotide position 2606). In other embodiments, the target region to be amplified is a Bp target region substantially corresponding to SEQ ID NO: 1 from about nucleotide position 1605 to about nucleotide position 1785, or substantially corresponding to a region contained therein (e.g., a target region from about nucleotide position 1634 to about nucleotide position 1731). Particularly suitable oligomer combinations for amplification of these Bp target regions are described herein. For example, in some embodiments, an amplification oligomer combination for amplifying a Bp target region includes first and second Bp-specific amplification oligomers comprising, respectively, (A) a first Bp-specific target-hybridizing sequence that is SEQ ID NO:3, SEQ ID NO:6, SEQ ID NO:9, SEQ ID NO: 12, or SEQ ID NO: 45, or a sequence substantially corresponding to SEQ ID NO:3, SEQ ID NO:6, SEQ ID NO: 9, SEQ ID NO: 12, or SEQ ID NO:45, or an RNA equivalent or DNA/RNA chimeric thereof, and (B) a second Bp-specific target-hybridizing sequence that is SEQ ID NO:5, SEQ ID NO: 8, SEQ ID NO:11, SEQ ID NO: 14, or SEQ ID NO:46, or a sequence substantially corresponding to SEQ ID NO:5, SEQ ID NO:8, SEQ ID NO: 11, SEQ ID NO: 14, or SEQ ID NO: 46, or an RNA equivalent or DNA/RNA chimeric thereof. In other embodiments, an amplification oligomer combination for amplifying a Bp target region includes first and second Bp-specific amplification oligomers comprising, respectively, (A) a first Bp-specific target-hybridizing sequence that is SEQ ID NO: 15 or a sequence substantially corresponding to SEQ ID NO: 15, or an RNA equivalent or DNA/RNA chimeric thereof, and (B) a second Bp-specific target-hybridizing sequence that is SEQ ID NO:17 or a sequence substantially corresponding to SEQ ID NO:17, or an RNA equivalent or DNA/RNA chimeric thereof. In other embodiments, an amplification oligomer combination for amplifying a Bp target region includes first and second Bp-specific amplification oligomers comprising, respectively, (A) a first Bp-specific target-hybridizing sequence that is SEQ ID NO: 18, SEQ ID NO:21, or SEQ ID NO: 27, or a sequence substantially corresponding to SEQ ID NO: 18, SEQ ID NO:21, or SEQ ID NO:27, or an RNA equivalent or DNA/RNA chimeric thereof, and (B) a second Bp-specific target-hybridizing sequence that is SEQ ID NO:20, SEQ ID NO:23, or SEQ ID NO: 29, or a sequence substantially corresponding to SEQ ID NO:20, SEQ ID NO:23, or SEQ ID NO: 29, or an RNA equivalent or DNA/RNA chimeric thereof.

In other embodiments, the target region to be amplified is a Bpp target region substantially corresponding to SEQ ID NO:2 from about nucleotide position 649 to about nucleotide position 1112, or substantially corresponding to a region contained therein (e.g., a target region from about nucleotide position 692 to about nucleotide position 790, or from about nucleotide position 712 to about nucleotide position 899). In other embodiments, the target region to be amplified is a Bpp target region substantially corresponding to SEQ ID NO: 2 from about nucleotide position 200 to about nucleotide position 313. In other embodiments, the target region to be amplified is a Bpp target region substantially corresponding to SEQ ID NO:2 from about nucleotide position 399 to about nucleotide position 491. Particularly suitable oligomer combinations for amplification of these Bpp target regions are described herein. For example, in some embodiments, an amplification oligomer combination for amplifying a Bpp target region includes first and second Bpp-specific amplification oligomers comprising, respectively, (A') a first Bpp-specific target-hybridizing sequence that is SEQ ID NO:30, SEQ ID NO:36, or SEQ ID NO:39, or a sequence substantially corresponding to SEQ ID NO:30, SEQ ID NO:36, or SEQ ID NO:39, or an RNA equivalent or DNA/RNA chimeric thereof, and (B') a second Bpp-specific target-hybridizing sequence that is SEQ ID NO:32, SEQ ID NO:38, or SEQ ID NO:41, or a sequence substantially corresponding to SEQ ID NO:32, SEQ ID NO:38, or SEQ ID NO:41, or an RNA equivalent or DNA/RNA chimeric thereof. In other embodiments, an amplification oligomer combination for amplifying a Bpp target region includes first and second Bpp-specific amplification oligomers comprising, respectively, (A') a first Bpp-specific target-hybridizing sequence that is SEQ ID NO:33 or a sequence substantially corresponding to SEQ ID NO:33, or an RNA equivalent or DNA/RNA chimeric thereof, and (B') a second Bpp-specific target-hybridizing sequence that is SEQ ID NO:35 or a sequence substantially corresponding to SEQ ID NO:35, or an RNA equivalent or DNA/RNA chimeric thereof. In other embodiments, an amplification oligomer combination for amplifying a Bpp target region includes first and second Bpp-specific amplification oligomers comprising, respectively, (A') a first Bpp-specific target-hybridizing sequence that is SEQ ID NO:42, or a sequence substantially corresponding to SEQ ID NO:42, or an RNA equivalent or DNA/RNA chimeric thereof, and (B') a second Bpp-specific target-hybridizing sequence that is SEQ ID NO: 44, or a sequence substantially corresponding to SEQ ID NO:44, or an RNA equivalent or DNA/RNA chimeric thereof.

In some embodiments where a target region to be amplified is a *Bordetella pertussis* target region, the first (A) and second (B) Bp-specific target-hybridizing sequences are selected from (i) (A) SEQ ID NO:3, or a sequence substantially corresponding to SEQ ID NO: 3, or an RNA equivalent or DNA/RNA chimeric thereof, and (B) SEQ ID NO:5, or a sequence substantially corresponding to SEQ ID NO: 5, or an RNA equivalent or DNA/RNA chimeric thereof;

(ii) (A) SEQ ID NO:6, or a sequence substantially corresponding to SEQ ID NO: 6, or an RNA equivalent or DNA/RNA chimeric thereof, and (B) SEQ ID NO:8, or a sequence substantially corresponding to SEQ ID NO: 8, or an RNA equivalent or DNA/RNA chimeric thereof;

(iii) (A) SEQ ID NO:9, or a sequence substantially corresponding to SEQ ID NO: 9, or an RNA equivalent or DNA/RNA chimeric thereof, and (B) SEQ ID NO:11, or a sequence substantially corresponding to SEQ ID NO: 11, or an RNA equivalent or DNA/RNA chimeric thereof;

(iv) (A) SEQ ID NO:12, or a sequence substantially corresponding to SEQ ID NO: 12, or an RNA equivalent or DNA/RNA chimeric thereof, and (B) SEQ ID NO:14, or a sequence substantially corresponding to SEQ ID NO: 14, or an RNA equivalent or DNA/RNA chimeric thereof;

(v) (A) SEQ ID NO: 15, or a sequence substantially corresponding to SEQ ID NO: 15, or an RNA equivalent or DNA/RNA chimeric thereof, and (B) SEQ ID NO:17, or a sequence substantially corresponding to SEQ ID NO: 17, or an RNA equivalent or DNA/RNA chimeric thereof;

(vi) (A) SEQ ID NO:18, or a sequence substantially corresponding to SEQ ID NO: 18, or an RNA equivalent or DNA/RNA chimeric thereof, and (B) SEQ ID NO:20, or a sequence substantially corresponding to SEQ ID NO: 20, or an RNA equivalent or DNA/RNA chimeric thereof;

(vii) (A) SEQ ID NO:21, or a sequence substantially corresponding to SEQ ID NO: 21, or an RNA equivalent or DNA/RNA chimeric thereof, and (B) SEQ ID NO:23, or a sequence substantially corresponding to SEQ ID NO: 23, or an RNA equivalent or DNA/RNA chimeric thereof; and (viii) (A) SEQ ID NO:27, or a sequence substantially corresponding to SEQ ID NO: 27, or an RNA equivalent or DNA/RNA chimeric thereof, and (B) SEQ ID NO:29, or a sequence substantially corresponding to SEQ ID NO: 29, or an RNA equivalent or DNA/RNA chimeric thereof.

In some embodiments where a target region to be amplified is a *Bordetella parapertussis* target region, the first (A') and second (B') Bpp-specific target-hybridizing sequences are selected from (i') (A') SEQ ID NO:30, or a sequence substantially corresponding to SEQ ID NO: 30, or an RNA equivalent or DNA/RNA chimeric thereof, and (B') SEQ ID NO:32, or a sequence substantially corresponding to SEQ ID NO: 32, or an RNA equivalent or DNA/RNA chimeric thereof;

(ii') (A') SEQ ID NO:33, or a sequence substantially corresponding to SEQ ID NO: 33, or an RNA equivalent or DNA/RNA chimeric thereof, and (B') SEQ ID NO:35, or a sequence substantially corresponding to SEQ ID NO: 35, or an RNA equivalent or DNA/RNA chimeric thereof;

(iii') (A') SEQ ID NO:36, or a sequence substantially corresponding to SEQ ID NO: 36, or an RNA equivalent or DNA/RNA chimeric thereof, and (B') SEQ ID NO:38, or a sequence substantially corresponding to SEQ ID NO: 38, or an RNA equivalent or DNA/RNA chimeric thereof;

(iv') (A') SEQ ID NO:39, or a sequence substantially corresponding to SEQ ID NO: 39, or an RNA equivalent or DNA/RNA chimeric thereof, and (B') SEQ ID NO:41, or a sequence substantially corresponding to SEQ ID NO: 41, or an RNA equivalent or DNA/RNA chimeric thereof; and (v') (A') SEQ ID NO:42, or a sequence substantially corresponding to SEQ ID NO: 42, or an RNA equivalent or DNA/RNA chimeric thereof, and (B') SEQ ID NO:44, or a sequence substantially corresponding to SEQ ID NO: 44, or an RNA equivalent or DNA/RNA chimeric thereof.

In some embodiments where both a *Bordetella pertussis* target region and a *Bordetella parapertussis* target region are to be amplified, a first amplification oligomer combination as disclosed herein for amplification of a Bp target region is used in combination with a second amplification oligomer combination as disclosed herein for amplification of a Bpp target region. For example, a first amplification oligomer combination where the first (A) and second (B) Bp-specific target-hybridizing sequences are selected from (i)-(viii) as set forth above may be used in combination with second amplification oligomer combination where the first (A') and second (B') Bpp-specific target hybridizing sequences are selected from (i')-(v') as set forth above. In particular variations, a combination of first and second Bp-specific target-hybridizing sequences together with first and second Bpp-specific target-hybridizing sequences is any one of combinations C1-C20 indicated in Table 3 below (where each "C[#]" designation represents a specific combination of first and second Bp-specific target hybridizing sequences (THSs) with first and second Bpp-specific target-hybridizing sequences (THSs). An oligomer combination of any one of combinations C1-C20 may be used in further combination with Bp and/or Bpp detection probe oligomers as described herein.

TABLE 3

*B. pertussis* Oligomer Target Hybridizing Sequences in Combination with *B. parapertussis* Oligomer Target Hybridizing Sequences

| | | Bpp THSs ($1^{st}/2^{nd}$ SEQ ID NOs) | | | | |
|---|---|---|---|---|---|---|
| | | 30/32 | 33/35 | 36/38 | 39/41 | 42/44 |
| Bp THSs ($1^{st}/2^{nd}$ SEQ ID NOs) | 3/5 | C1 | C2 | C3 | C4 | C5 |
| | 6/8 | C6 | C7 | C8 | C9 | C10 |
| | 9/11 | C11 | C12 | C13 | C14 | C15 |
| | 12/14 | C16 | C17 | C18 | C19 | C20 |
| | 15/17 | C21 | C22 | C23 | C24 | C25 |
| | 18/20 | C26 | C27 | C28 | C29 | C30 |
| | 21/23 | C31 | C32 | C33 | C34 | C35 |
| | 27/29 | C36 | C37 | C38 | C39 | C40 |

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the *Bordetella pertussis* and/or *Bordetella parapertussis* target nucleic acid from other components in the sample, e.g., before an amplification, such as before a capture step. Such purification may include methods of separating and/or concentrating organisms contained in a sample from other sample components, or removing or degrading non-nucleic acid sample components, e.g., protein, carbohydrate, salt, lipid, etc. In some embodiments, DNA in the sample is degraded, e.g., with DNase, and optionally removing or inactivating the DNase or removing degraded DNA.

In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Bordetella pertussis* and/or *Bordetella parapertussis* nucleic acid and other sample components.

Target capture typically occurs in a solution phase mixture that contains one or more capture probe oligomers that hybridize to the Bp or Bpp target sequence under hybridizing conditions. For embodiments comprising a capture probe tail, the Bp-target:capture-probe or Bpp-target:capture-probe complex is captured by adjusting the hybridization conditions so that the capture probe tail hybridizes to an immobilized probe. Certain embodiments use a particulate solid support, such as paramagnetic beads.

Isolation can follow capture, where, for example, the complex on the solid support is separated from other sample components. Isolation can be accomplished by any appropriate technique, e.g., washing a support associated with the Bp or Bpp target-sequence one or more times (e.g., two or three times) to remove other sample components and/or unbound oligomer. In embodiments using a particulate solid support, such as paramagnetic beads, particles associated with the Bp or Bpp target may be suspended in a washing solution and retrieved from the washing solution, in some embodiments by using magnetic attraction. To limit the number of handling steps, the Bp or Bpp target nucleic acid may be amplified by simply mixing the target sequence in the complex on the support with amplification oligomers and proceeding with amplification steps.

Exponentially amplifying a *Bordetella pertussis* and/or *Bordetella parapertussis* target sequence utilizes an in vitro amplification reaction using at least two amplification oligomers that flank a target region to be amplified. In some embodiments, at least first and second oligomers as described herein are provided. In some embodiments, a plurality of pairs of oligomers is provided; in some such variations, a plurality of oligomer pairs comprises oligomer pairs configured to hybridize to at least two Bp and/or Bpp target nucleic acids (e.g., at least one oligomer pair configured to hybridized to a Bp target nucleic acid and at least one oligomer pair configured to hybridize to a Bpp target nucleic acid). The amplification reaction can be cycled or isothermal. Suitable amplification methods include, for example, replicase-mediated amplification, polymerase chain reaction (PCR), ligase chain reaction (LCR), strand-displacement amplification (SDA), and transcription-mediated or transcription-associated amplification (TMA).

A detection step may be performed using any of a variety of known techniques to detect a signal specifically associated with the amplified target sequence, such as, e.g., by hybridizing the amplification product with a labeled detection probe and detecting a signal resulting from the labeled probe (including from label released from the probe following hybridization in some embodiments). In some embodiments, the labeled probe comprises a second moiety, such as a quencher or other moiety that interacts with the first label, as discussed above. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see. e.g., U.S. Pat. Nos. 5,639,604 and 5,283,174). In some embodiments, the nucleic acids are associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the *Bordetella pertussis* or *Bordetella parapertussis* gene, and a probe will bind directly or indirectly to a sequence contained in the amplified product to indicate the presence of *B. pertussis* or *B. parapertussis* nucleic acid in the tested sample.

In embodiments that detect the amplified product near or at the end of the amplification step, a linear detection probe may be used to provide a signal to indicate hybridization of the probe to the amplified product. One example of such detection uses a luminescentally labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product (e.g., a dual-labeled hairpin probe comprising both a fluorescent label and a quenching moiety). In other embodiments for real-time detection, the detection probe is a linear oligomer such as, e.g., an oligomer labeled with both a fluorophore and a quenching moiety (e.g., a TaqMan probe). Such probes may comprise target-hybridizing sequences and non-target-hybridizing sequences. Various forms of such probes have been described previously (see, e.g., U.S. Pat. Nos. 5,210,015; 5,487,972; 5,118,801; 5,312,728; 5,925,517; 6,150,097; 6,849,412; 6,835,542; 6,534,274; and 6,361,945; and US Patent Application Pub. Nos. 20060194240A1; each incorporated by reference herein).

Assays for detection of the *Bordetella pertussis* and/or *Bordetella parapertussis* nucleic acid may optionally include a non-Bp/Bpp internal control (IC) nucleic acid that is amplified and detected in the same assay reaction mixtures by using amplification and detection oligomers specific for the IC sequence. IC nucleic acid sequences can be, e.g., a DNA plasmid, an RNA template sequence (e.g., an in vitro transcript), or a synthetic nucleic acid that is spiked into a sample. Alternatively, the IC nucleic acid sequence may be a cellular component, which may be from exogenous cellular sources or endogenous cellular sources relative to the specimen. In these instances, an internal control nucleic acid is co-amplified with the Bp and/or Bpp nucleic acid in the amplification reaction mixtures. The internal control amplification product and the Bp and/or Bpp target sequence amplification product can be detected independently.

In certain embodiments, amplification and detection of a signal from an amplified IC sequence demonstrates that the assay reagents, conditions, and performance of assay steps were properly used in the assay if no signal is obtained for the intended target Bp and/or Bpp nucleic acid (e.g., samples that test negative for Bp and/or Bpp). An IC may also be used as an internal calibrator for the assay when a quantitative result is desired, i.e., the signal obtained from the IC amplification and detection is used to set a parameter used in an algorithm for quantitating the amount of Bp and/or Bpp nucleic acid in a sample based on the signal obtained for an amplified Bp and/or Bpp target sequence. ICs are also useful for monitoring the integrity of one or more steps in an assay. The primers and probe for the IC target sequence are configured and synthesized by using any well-known method provided that the primers and probe function for amplification of the IC target sequence and detection of the amplified IC sequence using substantially the same assay conditions used to amplify and detect the Bp and/or Bpp target sequence. In preferred embodiments that include a target capture-based purification step, it is preferred that a target capture probe specific for the IC target be included in the assay in the target capture step so that the IC is treated in the assay in a manner analogous to that for the intended Bp and/or Bpp analyte in all of the assay steps.

Also provided by the subject invention are formulations for determining the presence or absence of *Bordetella pertussis* and/or *Bordetella parapertussis* in a sample. In some embodiments, a formulation is an aqueous formulation comprising (1) (a) at least two Bp-specific amplification oligomers for amplification of a Bp target region as described herein and/or (b) at least two Bpp-specific amplification oligomers for amplification of a Bpp target region as described herein and (2) an organic buffer. An aqueous formulation for amplification of a Bp and/or Bpp nucleic acid may include one or more additional components such as, e.g., a DNA polymerase enzyme, a reverse transcriptase enzyme, or a detection probe oligomer. In some embodiments, a formulation is an aqueous formulation comprising (1) a Bp-specific and/or Bpp-specific detection probe oligomer as described herein and (2) an organic buffer. An aqueous formulation for comprising or more detection probe oligomers may include one or more additional components such as, e.g., a surfactant, a DNA polymerase enzyme, a reverse transcriptase enzyme, or at least one amplification oligomer. Particularly suitable surfactants include, for example, polyethylene glycol mono [4-(1,1,3,3-tetramethylbutyl) phenyl] ether and polyoxyethylene sorbitan fatty acid esters (e.g., polysorbate 20, polysorbate 40, or polysorbate 60). In some embodiments, a surfactant in an aqueous detection probe formulation is a non-linear surfactant such as, for example, a polyoxyethylene sorbitan fatty acid ester (e.g., polysorbate 20, polysorbate 40, or polysorbate 60) or digitonin. An aqueous formulation as above for amplification or detection of Bp and/or Bpp nucleic acid may further include a bulking agent such as, e.g., trehalose, raffinose, or a combination thereof. In some embodiments, an aqueous formulation as above contains at inorganic salt such as, e.g., magnesium, potassium, or sodium; in some such variations, the concentration of the inorganic salt is 4 mM or less. A particularly suitable organic buffer for an aqueous formulation as above is Tris (2-amino-2-(hydroxymethyl)-1,3-propanediol).

In a related aspect, for long-term storage, an aqueous formulation as described herein may be aliquoted into, e.g., vials, ampules, or other containers and dried (e.g., lyophilized) according to procedures known in the art. The dried product typically appears as a powder or cake. The containers are then sealed. Methods of preparing such dried formulations from the aqueous formulation, as well as the dried formulations prepared by such methods, are additional aspects of the present invention. In yet another aspect, the present invention provides a dried formulation that enables reconstitution into an aqueous formulation as described herein. Dried formulations for amplification or detection of *Bordetella pertussis* and/or *Bordetella parapertussis* nucleic acid typically contain, in addition to one or more amplification oligomers and/or detection probes as described herein, a bulking agent such as, e.g., trehalose, raffinose, or a combination thereof. In some embodiments further comprising an inorganic salt, the percent mass of the inorganic salt to the mass of the dried formulation is 0.249% or less, 0.222% or less, or 0.195% or less. Methods of preparing a dried formulation from a lyophilized formulation as described herein are also encompassed by the present invention; such methods generally include dissolving the dried formulation in a suitable diluent (e.g., an organic buffer or water) to provide a reconstituted formulation.

Also provided by the subject invention is a reaction mixture for determining the presence or absence of a *Bordetella pertussis* and/or *Bordetella parapertussis* target nucleic acid in a sample. A reaction mixture in accordance with the present disclosure includes one or both of (1) an oligomer combination as described herein for amplification of a *B. pertussis* and/or *B. parapertussis* target nucleic acid and (2) one or more detection probe oligomers as described herein for determining the presence or absence of a *B. pertussis* and/or *B. parapertussis* amplification product. The reaction mixture may further include a number of optional components such as, for example, capture probes, e.g., poly-(k) capture probes as described in US 2013/0209992, which is incorporated herein by reference. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, and dTTP; and/or ATP, CTP, GTP and UTP), and/or enzymes (e.g., a thermostable DNA polymerase, or reverse transcriptase and/or RNA polymerase), and will typically include test sample components, in which a *B. pertussis* or *B. parapertussis* target nucleic acid may or may not be present. A reaction mixture may include amplification oligomers for only one target region of a *B. pertussis* or *B. parapertussis* genome, or it may include amplification oligomers for multiple *B. pertussis* and/or *B. parapertussis* target regions (e.g., both a *B. pertussis* target region and a *Bordetella parapertussis* target region). In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture). In some embodiments, a reaction mixture comprises an aqueous formulation as described above. In some embodiments, a reaction mixture is reconstituted with water or an organic buffer from a dried formulation as described above.

Also provided by the subject invention are kits for practicing the methods as described herein. A kit in accordance with the present disclosure includes one or both of (1) an oligomer combination as described herein for amplification of a *B. pertussis* and/or *B. parapertussis* target nucleic acid and (2) one or more detection probe oligomers as described herein for determining the presence or absence of a *B. pertussis* and/or *B. parapertussis* amplification product. In some embodiments, any oligomer combination described herein is present in the kit. The kits may further include a number of optional components such as, for example, capture probes, e.g., poly-(k) capture probes as described in US 2013/0209992. Other reagents that may be present in the kits include reagents suitable for performing in vitro amplification such as, e.g., buffers, salt solutions, appropriate nucleotide triphosphates (e.g., dATP, dCTP, dGTP, dTTP; and/or ATP, CTP, GTP and UTP), and/or enzymes (e.g., a thermostable DNA polymerase, or a reverse transcriptase and/or RNA polymerase). Oligomers as described herein may be packaged in a variety of different embodiments, and those skilled in the art will appreciate that the disclosure embraces many different kit configurations. For example, a kit may include amplification oligomers for only one target region of a Bp or Bpp genome, or it may include amplification oligomers for multiple Bp and/Bpp target regions (e.g., both a Bp target region and a Bpp target region). In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present disclosure, where the instructions may be associated with a package insert and/or the packaging of the kit or the components thereof.

The invention is further illustrated by the following non-limiting examples.

Example 1: *Bordetella pertussis* and *Bordetella parapertussis* Detection in Simplex Experiments were performed on the Applied Biosystems® (ABI) 7500 FAST Real-Time PCR System (ABI) with the Fast cycling option using the following PCR cycles: step 1-2 minutes at 95° C. (1 cycle); step 2-eight seconds at 95° C., 30 seconds at 60° C. (45 cycles).

*Bordetella pertussis*—Experiment 1

The Bp primer/probe (P/P) sets shown in Table 4 were tested.

TABLE 4

Primer/Probe Sets for *Bordetella pertussis* Detection

| P/P Set No. | Forward Primer (SEQ ID NO) | Reverse Primer (SEQ ID NO) | Probe (SEQ ID NO) |
|---|---|---|---|
| 1 | 9 | 11 | 10 |
| 2 | 12 | 14 | 13 |
| 3 | 15 | 17 | 16 |
| 4 | 18 | 20 | 19 |
| 5 | 21 | 23 | 22 |
| 6 | 24 | 26 | 25 |
| 7 | 27 | 29 | 28 |

Each P/P set for Bp detection (set 1 to 7) was tested in simplex at an initial concentration of 300 nM for the primers and 100 nM for the probes (300/100 nM) on 0.6 c/μL (estimated concentration from ATCC stock) of Bp genomic DNA (gDNA). P/P sets 1, 4, 5, and 7 gave the highest fluorescence emission and lowest Ct value and were selected for further evaluation. Mean Ct values are shown in Table 5.

TABLE 5

| | Simplex on gDNA Bp | | |
|---|---|---|---|
| P/P Set | Mean Ct | SD | N |
| 1 | 36.5 | 0.8 | 3 |
| 2 | 38.4 | 0.5 | 3 |
| 3 | — | — | 3 |
| 4 | 36.4 | 0.5 | 3 |
| 5 | 36.8 | 0.5 | 3 |
| 6 | 39.6 | 0.3 | 3 |
| 7 | 36.8 | 0.3 | 3 |

*Bordetella pertussis*—Experiment 2

P/P sets for Bp detection selected from Experiment 1 above, together with an additional set of P/P for Bp detection (set 0; forward primer, reverse primer, and probe of SEQ ID NO:6, SEQ ID NO:8, and SEQ ID NO:7, respectively), were tested on more concentrated Bp gDNA (6.4c/μL, estimated concentration from ATCC stock). All sets were tested at a P/P concentration of 300/100 nM. P/P set 0 gave the highest fluorescence emission and the lowest Ct value. Mean Ct values are shown in Table 6.

TABLE 6

| | Simplex on gDNA Bp | | |
|---|---|---|---|
| P/P Set | Mean Ct | SD | N |
| 0 | 32.8 | 0.1 | 3 |
| 1 | 33.7 | 0.5 | 3 |
| 4 | 34.4 | 0.4 | 3 |
| 5 | 34.0 | 0.5 | 3 |
| 7 | 34.8 | 0.9 | 3 |

*Bordetella parapertussis*

The Bpp primer/probe (P/P) sets shown in Table 7 were tested.

TABLE 7

Primer/Probe Sets for *Bordetella parapertussis* Detection

| P/P Set No. | Forward Primer (SEQ ID NO) | Reverse Primer (SEQ ID NO) | Probe (SEQ ID NO) | Dye |
|---|---|---|---|---|
| 8 | 30 | 32 | 31 | FAM |
| 9 | 33 | 35 | 34 | FAM |
| 10 | 36 | 38 | 37 | FAM |
| 11 | 39 | 41 | 40 | FAM |
| 12 | 42 | 44 | 43 | YD |
| 13 | 39 | 41 | 40 | YD |

Each P/P set for Bpp detection (set 8 to 13) was tested in simplex at an initial concentration of 300/100 nM with a low concentration of Bpp gDNA (estimated concentration from ATCC stock=0.9 C/μL). P/P set 8 gave the highest fluorescence emission and the lowest Ct value. Mean Ct values are shown in Table 8.

TABLE 8

| | Simplex on gDNA Bp | | |
|---|---|---|---|
| P/P Set | Mean Ct | SD | N |
| 8 | 33.8 | 0.5 | 3 |
| 9 | 35.5 | 0.1 | 3 |
| 10 | 39.3 | 0.6 | 3 |
| 11 | 35.3 | 0.4 | 3 |
| 12 | 35.4 | 0.5 | 3 |
| 13 | 35.5 | 0.4 | 3 |

Example 2: *Bordetella pertussis* and *parapertussis* Detection in Duplex

Four sets of Bp P/P and four sets of Bpp P/P were tested in simplex and combined in duplex (16 combinations) at a concentration of 300/100 nM each. As all Bp and Bpp probes were labeled with FAM dye, samples were composed either by Bp or Bpp gDNA at approximatively 8c/μL (estimated from ATCC stock).

Mean Ct and delta Ct (ΔCt) values obtained for Bp detection in simplex and duplex are listed in Table 9. The lowest Ct values obtained for Bp detection in duplex (in bold text in Table 9) were with combined sets 0/11 (34.4), 0/8 (34.5), 0/13 (35.0), and 4/11 (35.1). All of these sets have a ΔCt value≤0.6 (between simplex and duplex Ct mean).

TABLE 9

| | | Simplex on gDNA Bp | | | Duplex on gDNA Bp | | | |
|---|---|---|---|---|---|---|---|---|
| PP Bp | PP Bpp | Mean Ct | SD | N | Mean Ct | SD | N | ΔCt |
| Set 0 | Set 8 | 34.9 | 0.2 | 3 | **34.5** | 0.2 | 3 | 0.4 |
| | Set 11 | | | | **34.4** | 0.3 | 3 | 0.5 |
| | Set 12 | | | | 35.2 | 0.2 | 3 | 0.3 |
| | Set 13 | | | | **35.5** | 0.4 | 3 | 0.1 |
| Set 4 | Set 8 | 35.7 | 0.2 | 3 | 35.3 | 0.3 | 3 | 0.4 |
| | Set 11 | | | | **35.1** | 0.5 | 3 | 0.6 |
| | Set 12 | | | | 35.7 | 0.3 | 3 | 0.0 |
| | Set 13 | | | | 35.4 | 0.3 | 3 | 0.3 |
| Set 5 | Set 8 | 36.5 | 0.1 | 3 | 36.4 | 0.2 | 3 | 0.1 |
| | Set 11 | | | | 36.0 | 0.4 | 3 | 0.5 |
| | Set 12 | | | | 42.6 | 0.5 | 3 | 6.2 |
| | Set 13 | | | | 36.8 | 0.5 | 3 | 0.4 |
| Set 7 | Set 8 | 37.2 | 0.7 | 3 | 37.0 | 0.4 | 3 | 0.2 |
| | Set 11 | | | | 36.8 | 0.7 | 3 | 0.3 |
| | Set 12 | | | | 37.3 | 0.9 | 3 | 0.2 |
| | Set 13 | | | | 37.1 | 0.7 | 3 | 0.1 |

Mean Ct and ΔCt values obtained for Bpp detection in simplex and duplex are listed in Table 10. The lowest Ct values obtained for Bpp detection in duplex (in bold text in Table 10) were with combined sets 7/8 (34.9), 5/8 (34.9), 0/12 (35.0), and 0/8 (35.3). All these sets have a ΔCt value≤0.5 (between simplex and duplex Ct mean).

TABLE 10

| | | Simplex on gDNA Bpp | | | Duplex on gDNA Bpp | | | |
|---|---|---|---|---|---|---|---|---|
| PP Bp | PP Bpp | Mean Ct | SD | N | Mean Ct | SD | N | ΔCt |
| Set 0 | Set 8 | 35.3 | 0.3 | 3 | **35.3** | 0.1 | 3 | 0.0 |
| | Set 11 | 35.7 | 0.1 | 3 | 36.3 | 0.7 | 3 | 0.6 |
| | Set 12 | 34.9 | 1.1 | 3 | **35.0** | 0.5 | 3 | 0.1 |
| | Set 13 | 36.2 | 0.5 | 3 | 36.6 | 0.2 | 3 | 0.4 |
| Set 4 | Set 8 | 35.3 | 0.3 | 3 | 35.4 | 0.4 | 3 | 0.1 |
| | Set 11 | 35.7 | 0.1 | 3 | 36.4 | 0.6 | 3 | 0.7 |
| | Set 12 | 34.9 | 1.1 | 3 | 35.9 | 0.7 | 3 | 1.0 |
| | Set 13 | 36.2 | 0.5 | 3 | 36.9 | 0.5 | 3 | 0.7 |
| Set 5 | Set 8 | 35.4 | 0.6 | 3 | **34.9** | 0.8 | 3 | 0.5 |
| | Set 11 | 35.8 | 0.5 | 3 | 35.8 | 0.7 | 3 | 0.0 |
| | Set 12 | 35.9 | 0.2 | 3 | 44.1 | 0.2 | 3 | 8.2 |
| | Set 13 | 36.4 | 0.4 | 3 | 36.5 | 0.2 | 3 | 0.1 |
| Set 7 | Set 8 | 35.4 | 0.6 | 3 | **34.9** | 0.5 | 3 | 0.5 |
| | Set 11 | 35.8 | 0.5 | 3 | 36.1 | 0.2 | 3 | 0.3 |
| | Set 12 | 35.9 | 0.2 | 3 | 36.2 | 0.5 | 3 | 0.3 |
| | Set 13 | 36.4 | 0.4 | 3 | 36.4 | 0.3 | 3 | 0.0 |

Based on these results (mean Ct in duplex, ΔCt) and considering Ct values for both Bp and Bpp detection, the combination of sets 0/8 was selected for further evaluation.

Example 3: *Bordetella pertussis* and *parapertussis* Co-Infection Testing

The co-infection experiment evaluates the capacity of the *Bordetella* assay to detect low concentrated Bp or Bpp in a sample containing high concentration of the other pathogen. To assess the co-infection detection of the assay, Bp and Bpp were tested with and without coinfecting target:

- gDNA Bp spiked at low concentration (0.6 C/μL) with or without gDNA Bpp at high concentration (9160 C/μL)
- gDNA Bpp spiked at low concentration (0.9 C/μL) with or without gDNA Bp at high concentration (6410 C/μL).

Testing was performed with Bp P/P set 0 at 500/200 nM and Bpp P/P set 8 at 300/150 nM.

Ct values obtained for Bp and Bpp were not impacted by co-infection or not. End-points fluorescence were at the same level for Bp with and without co-infection (around 2,500,000 RFU), and for Bpp (around 550,000 RFU). IC Ct values were the same for all tested conditions and end-point fluorescence values were the same for all conditions (around 180,000 RFU).

Example 4: Negative Human Matrixes Testing

To confirm that the *Bordetella* assay does not cross react with the components and the microorganisms consortium present in a negative human matrix, the assay was tested on one pool of 10 negative NPA. Each of them was previously diagnosed negative for Bp and Bpp with Diagenode commercial kit after extraction on the suitable MagNA Pure 96 system. Testing was performed with Bp P/P set 0 at 500/200 nM and Bpp P/P set 8 at 300/150 nM. All of the results were confirmed negative for Bp and Bpp and the IC was correctly detected with a mean Ct value of 32.

Conclusions: No a specific reaction was observed for the *Bordetella* assay when tested on representative negative human NPA matrixes.

Example 5: PCR Linearity

The linearity and efficiency of the PCR was assessed directly on ABI (without extraction) with quantified Bp and Bpp gDNA from Vircell. Testing was performed with Bp P/P set 0 at 500/200 nM and Bpp P/P set 8 at 300/150 nM. The IC target was added to the PCR well at 500c/mL. Results are summarized in Tables 11 and 12 below.

TABLE 11

Mean Bp and Bpp Ct Values

| | Vircell concentration (c/mL) | Mean Ct | Log conc. | SD |
|---|---|---|---|---|
| Bp | 5000 | 25.7 | 3.70 | 0.1 |
| | 500 | 29.1 | 2.70 | 0.2 |
| | 50 | 32.5 | 1.70 | 0.3 |
| | 5 | 35.7 | 0.70 | 0.2 |
| Bpp | 16500 | 26.3 | 4.22 | 0.2 |
| | 1650 | 29.8 | 3.22 | 0.2 |
| | 165 | 32.9 | 2.22 | 0.1 |
| | 16.5 | 35.9 | 1.22 | 0.7 |

TABLE 12

Bp and Bpp PCR Efficiency

| | Acceptance Criteria | Bp | Bpp |
|---|---|---|---|
| Slope | Between −3.6 and −3.0 | −3.32 | −3.2 |
| Efficiency PCR | Between 90% | 1.00 | 1.06 |
| Efficiency PCR (%) | and 110% | 100.0% | 105.5% |
| $R^2$ | Between 0.95 and 1.00 | 1.00 | 1.00 |

Conclusions: The amplification for Bp and Bpp was linear and the PCR efficiency was close to 100%.

Example 6: Analytical Sensitivity/Limit of Detection (LoD)

$LoD_{95\%}$ of Bp (ATCC 9340) and Bpp (ATCC 53893) in ESwab matrix were assessed on the ABI 7500 FAST Real-Time PCR System after KINGFISHER™ extraction. Testing was performed with Bp P/P set 0 at 500/200 nM and Bpp P/P set 8 at 300/150 nM. Bp and Bpp ATCC strains were quantified by UZB (the Belgian reference center for *Bordetella* in Belgium). For each strain, 6 to 8 different concentrations were extracted in 5 replicates on the KINGFISHER system with wave 1 workflow. Eluates were pooled, and PCR was performed on the ABI system in 20 replicates for each concentration. The results were analyzed using a Probit analysis with MINITAB® 17 Software. Results are summarized in Tables 13-18.

Bp on ESwab

TABLE 13

| Concentration (CFU/mL) | Mean Ct | Positive call | Trials | % Positive Call |
|---|---|---|---|---|
| 8.16 | 37.85 | 20 | 20 | 100 |
| 4.08 | 38.49 | 20 | 20 | 100 |
| 1.02 | 39.52 | 12 | 20 | 60 |
| 0.51 | 40.87 | 9 | 20 | 45 |
| 0.13 | 40.87 | 1 | 20 | 5 |
| 0.06 | — | 0 | 10 | 0 |

TABLE 14

| Assumed distribution | P value for Regression | P value for goodness of fit Pearson method | P value for goodness of fit Deviance method |
|---|---|---|---|
| Weibull | 0.000 | 0.811 | 0.763 |
| Lognormal | 0.000 | 0.796 | 0.708 |
| Loglogistic | 0.000 | 0.677 | 0.551 |

TABLE 15

| Assumed distribution | LoD95% (CFU/mL) | Lower | Upper |
|---|---|---|---|
| Weibull | 2.2 | 1.4 | 6.0 |

Bpp on ESwab

TABLE 16

| Concentration (CFU/mL) | Mean Ct | Positive call | Trials | % Positive Call |
|---|---|---|---|---|
| 5.08 | 34.38 | 20 | 20 | 100 |
| 2.54 | 36.10 | 19 | 20 | 95 |
| 1.27 | 37.21 | 18 | 20 | 90 |
| 0.63 | 37.56 | 15 | 20 | 75 |
| 0.32 | 39.10 | 6 | 20 | 30 |
| 0.16 | 38.04 | 3 | 20 | 15 |
| 0.08 | 39.21 | 3 | 20 | 15 |
| 0.04 | 38.10 | 2 | 20 | 10 |
| 0.02 | — | 0 | 10 | 0 |

TABLE 17

| Assumed distribution | P value for Regression | P value for goodness of fit Pearson method | P value for goodness of fit Deviance method |
|---|---|---|---|
| Weibull | 0.000 | 0.679 | 0.655 |
| Lognormal | 0.000 | 0.390 | 0.419 |
| Loglogistic | 0.000 | 0.459 | 0.483 |

TABLE 18

| Assumed distribution | LoD95% (CFU/mL) | Lower | Upper |
|---|---|---|---|
| Weibull | 12.6 | 8.9 | 25.3 |

Conclusions: The LoD-95% determined for Bp in ESwab was 2.2 CFU/ml and the $LoD_{95\%}$ determined for Bpp in ESwab was 1.9 CFU/ml.

Example 7: Analytical Specificity

Analytical specificity was assessed by testing a panel of gDNA from 46 pathogens (most of them are from the respiratory tract) including four from *Bordetella* species (*Bordetella pertussis, Bordetella parapertussis, Bordetella holmesii*, and *Bordetella bronchiseptica*) (see Table 19). All pathogens were grouped by 3 to 5 but those from *Bordetella* species. Testing was performed with Bp P/P set 0 at 500/200 nM and Bpp P/P set 8 at 300/150 nM. Each group was tested by PCR only on the ABI 7500 AST Real-Time PCR System (no extraction). The final concentration of each target was equal or superior to $10^6$ C/μL.

TABLE 19

| Pathogen | Pathogen group |
|---|---|
| *Acinetobacter baumanii* | Group 1 |
| *Bacteroides fragilis* | |
| *Candida albicans* | |
| *Chlamydia pneumoniae* | |
| *Chlamydia trachomatis* | Group 2 |
| *Corynebacterium diptheriae* | |
| *Enterococcus faecalis* | |
| *Escherichia coli* | |
| *Haemophilus influenzae* | |
| *Klebsiella pneumoniae* | Group 3 |
| *Lactobacillus acidophilus* | |
| *Legionella pneumophilia* | |
| *Moraxella catarrhalis* | |
| *Mycobacterium tuberculosis* (avirulent) | Group 4 |
| *Mycoplasma genitalium* | |
| *Mycoplasma hominis* | |
| *Neisseria gonorrhoeae* | Group 5 |
| *Neisseria meningitidis* | |
| *Proteus vulgaris* | |
| *Pseudomonas aeruginosa* | |
| *Staphylococcus aureus* (MRSA) | Group 6 |
| *Stenotrophomonas maltophilia* | |
| *Streptococcus pneumoniae* | |
| *Streptococcus pyogenes* | |
| *Streptococcus salivarius* | |
| *Ureaplasma urealyticum* | Group 7 |
| Adenovirus 1 | |
| Coronavirus OC43 | |
| Cytomegalovirus | |
| HSV Type 1 | |
| HSV Type 2 (G) | Group 8 |
| Influenza A HINl | |
| Influenza B | |
| Measles virus | |
| Mumps virus | Group 9 |
| Parainfluenza Type 1 | |
| Parainfluenza Type 2 | |
| Parainfluenza Type 3 | |
| Parainfluenza Type 4 | |
| Respiratory Syncytial Virus A | Group 10 |
| Rhinovirus 17 | |
| Respiratory Syncytial Virus B | |
| *Bordetella bronchiseptica* | Group 11 |
| *Bordetella holmesii* | Group 12 |
| *Bordetella parapertussis* | Group 13 |
| *Bordetella pertussis* | Group 14 |

Regarding the non-*Bordetella* pathogens (groups 1 to 10), no specific amplification curve was observed, only a high background level for groups 4 and 5. As expected for *Bordetella* species: *B. pertussis* and *B. holmesii* were recognized as they have the targeted IS481 sequence and *B. parapertussis* was recognized. *B. bronchiseptica* was not recognized by either by Bp or Bpp. *B. bronchiseptica* strain BAA-588 from ATCC is an old strain that is not clinically relevant and contains none of the targeted sequence IS481 or IS1001 or the IS1002 repetition in its genome (see Parkhill et al., *Nat. Genet.* 35:32-40, 2003). No a-specific reaction was observed for the IC.

Example 8: Interfering Substances

Mucin, whole blood, and a number of exogenous substances (belonging to a class of antibiotic, antivirus, decongestant, local anesthetic, and glucocorticoids) that may be present in the nasopharynx were evaluated as interfering substances for the detection of Bp and Bpp. Bp and Bpp strains (ATCC 9797 and 53893) were spiked at $LoD_{95\%}$ into ESwab and NPA matrix. Clinically relevant amounts of the potential interfering substances were spiked to the samples. All samples are extracted on the KINGFISHER™ system and tested in five replicates on the ABI 7500 AST Real-Time PCR System. All the substances tested are listed in the Table 20 below.

TABLE 20

| Interfering substance | Active ingredient | Concentration tested |
|---|---|---|
| Mucin | Mucin | 60 μg/mL |
| Blood | Blood | 2% (volume/volume) |
| Neo-Synephrine | Phenylaphrine | 15% (volume/volume) |
| Anefrin nasal spray | Oxymetazoline | 75 μg/mL |
| Zicam nasal gel | Zicam nasal gel | 5% (volume/volume) |
| Saline nasal spray | NaCl 3% | 4.5 mg/mL |
| Chloraseptic throat lozenges | Throat lozenges | 1 mg/mL benzocaine |
| | | 1.7 mg/mL menthol |
| Relenza | Zanamivir | 3.3 mg/mL |
| Trobamycin | Trobamycin | 4 μg/mL |
| Mupirocin | Mupirocin | 6.6 mg/mL |
| Rebitol | Ribarivin | 20 mg/mL |
| TamiFlu | Oseltamivir phosphate | 25 mg/mL |
| Beconase AQ | Beclomethasone dipropionate | 210 μg/mL |

Compared with the Ct value of references (ESwab or NPA), none of the substances totally inhibited the detection of Bp or Bpp. Only the Oseltamivir phosphate (an antiviral medicine used in the treatment and prevention of influenza A and B) gave higher Ct values or less positive calls than the reference sample (without interfering substance) depending on the matrix and target.

Example 9: Lyophilized *Bordetella* Assay

Lyophilized and Liquid Format Comparison on ABI

The objective of this experiment was to compare a dried-down assay to a liquid assay format in order to assess is suitability of the assay for lyophilization. The *Bordetella* P/P and Hologic Master Mix were dried-down in Hologic PCR cartridges. Lyophilized pellets were reconstituted with the PANTHER FUSION® reconstitution buffer prior to be tested on Bp and Bpp gDNA (25c/μL and 5c/μL estimated from ATCC stock) and IC target at 500 C/ml directly on ABI 7500 AST Real-Time PCR System.

Three P/P Mix concentrations were lyophilized:

Nominal: Bp 500/200 nM; Bpp 300/150 nM; IC 200/300 nM

Nominal: −50%

Nominal: +50%

The couples fluorophores/quenchers used were respectively FAM/BHQI for Bp, JOE/BHQI for Bpp, and Quasar/BHQ2 for the IC.

At nominal and +50% concentration of P/P, dried-down and liquid assay formats gave comparable results in terms of Ct values and end-points fluorescence for Bp, Bpp, and IC detection. Compared to the nominal concentration, no Ct or RFU improvement was observed when the P/P was increased by 50%. When the concentration of P/P was decreased by 50%, Ct values and RFU were impacted negatively when lyophilized.

Testing of Lyophilized Format on PANTHER FUSION System

The *Bordetella* software implemented on the PANTHER FUSION system used the wave 1 extraction workflow and reagents and 5 μL eluate as sample. One *Bordetella* cartridge of each P/P concentration ratio (−50%, nominal, and +50% concentration) is tested on the PANTHER FUSION system with the *Bordetella* software on samples containing 25 and 17 CFU/ml of Bp and Bpp strains.

All the samples containing Bp and Bpp strains generated positive results in FAM and JOE channel respectively. As previously shown on the ABI, nominal and +50% concentration of P/P give comparable results in terms of Ct values and end-points fluorescence for Bp, Bpp, and IC detection. Compared to the nominal concentration, no major Ct or RFU improvement was observed when the P/P was increased by 50%. When the concentration of P/P was decreased by 50%, Ct values and RFU were impacted negatively.

Based on these results, the nominal concentrations of P/P (Bp 500/200 nM; Bpp 300/150 nM, and IC 200/300 nM) were selected for further evaluation.

Example 10: Limit of Detection (LoD) Determination on PANTHER FUSION System $LoD_{95\%}$ of Bp (ATCC 9340) and Bpp (ATCC 53893) in ESwab matrix were assessed on the PANTHER FUSION® system. For each strain, seven different concentrations of quantified Bp and Bpp strains were processed in 20 replicates on the PANTHER FUSION system. The results were analyzed using a Probit analysis with MINITAB® 17 Software. Results are summarized in Tables 21-26.

Bp on ESwab

TABLE 21

| Concentration (CFU/mL) | Mean Ct | Positive call | Trials | % Positive Call |
|---|---|---|---|---|
| 68 | 37.6 | 20 | 20 | 100 |
| 34 | 38 | 18 | 20 | 90 |
| 17 | 38.6 | 17 | 20 | 85 |
| 8.5 | 39.2 | 15 | 20 | 75 |
| 4.3 | 39.3 | 6 | 20 | 30 |
| 2.1 | 39.6 | 4 | 20 | 20 |
| 1.1 | 39.2 | 1 | 20 | 5 |

TABLE 22

| Assumed distribution | P value for Regression | P value for goodness of fit Pearson method | P value for goodness of fit Deviance method |
|---|---|---|---|
| Weibull | 0.000 | 0.331 | 0.344 |
| Lognormal | 0.000 | 0.671 | 0.658 |
| Loglogistic | 0.000 | 0.707 | 0.673 |

TABLE 23

| Assumed distribution | LoD95% (CFU/mL) | Lower | Upper |
|---|---|---|---|
| Loglogistic | 35 | 21.5 | 82.1 |

Bpp on ESwab

TABLE 24

| Concentration (CFU/mL) | Mean Ct | Positive call | Trials | % Positive Call |
|---|---|---|---|---|
| 12 | 38.31 | 20 | 20 | 100 |
| 6 | 40.35 | 20 | 20 | 100 |
| 3 | 40.54 | 19 | 20 | 95 |
| 1.5 | 41.36 | 17 | 20 | 85 |
| 0.7 | 41.59 | 12 | 20 | 60 |
| 0.4 | 41.63 | 3 | 20 | 15 |
| 0.2 | 42.44 | 2 | 20 | 10 |

TABLE 25

| Assumed distribution | P value for Regression | P value for goodness of fit Pearson method | P value for goodness of fit Deviance method |
|---|---|---|---|
| Weibull | 0.000 | 0.534 | 0.545 |
| Lognormal | 0.000 | 0.789 | 0.764 |
| Loglogistic | 0.000 | 0.830 | 0.798 |

TABLE 26

| Assumed distribution | LoD95% (CFU/mL) | Lower | Upper |
|---|---|---|---|
| Weibull | 12.6 | 8.9 | 25.3 |

Conclusions: The LoD95% determined for Bp in ESwab was 35 CFU/ml and the LoD95% determined for Bpp in ESwab was 2.5 CFU/ml.

Example 11: Design of Alternative Bp Oligonucleotides

Previous experiments on the ABI 7500 AST Real-Time PCR System showed that the selected sets of oligonucleotides targeting *Bordetella pertussis* (Bp) IS481 (set 0) and *Bordetella parapertussis* (Bpp) IS1001 (set 8) were the most appropriate oligonucleotide combination for the detection of Bp and Bpp in multiplex. Later experiments on the PANTHER FUSION system showed a significant decrease in RFU in the detection of surrogate NPS and NPA matrixes spiked with Bp. Further investigations showed that mucin, a PCR inhibitor, contained in NPS and NPA matrixes, mainly affected the Bp detection compared to Bpp or IC. In order to counteract this undesired inhibitory effect, new Bp oligonucleotides were designed close to the initial Bp amplicon. The new oligonucleotide sets are shown in Table 27.

TABLE 27

| Bp Oligo | Sequence | SEQ ID NO |
|---|---|---|
| Forward 1 | TTGCGTGAGTGGGCTTA | 3 |
| Forward 2 | CTTACGCTCACACCTACCA | 45 |
| Reverse 1 | CGATGCCAGTTGTAGTGGT | 46 |
| Reverse 2 | ATGCCAGTTGTAGTGGTGTA | 5 |
| Probe1 | AACACCGAGCCGATGCCATG | 4 |

The new Bp oligonucleotides were designed in the same region as the initial oligonucleotides. All possible combinations of these oligonucleotides were tested on spiked matrixes, and the combination of Forward 1 (SEQ ID NO:3), Reverse 2 (SEQ ID NO:5), and Probe 1 (SEQ ID NO:4) was selected for further evaluation in simplex and in multiplex together with the Bpp P/P set of SEQ ID NO:30, SEQ ID NO:32, and SEQ ID NO:31. These oligonucleotides showed excellent thermodynamic properties and gave excellent results in both liquid and lyophilized format on the PANTHER FUSION system. The new Bp oligonucleotides did not exhibit the previously observed decrease in RFU in the detection of surrogate NPS and NPA matrixes spiked with Bp.

SEQUENCES

TABLE 28

| SEQ ID NO | Description | Sequence (5′ → 3′) |
|---|---|---|
| 1 | *Bordetella pertussis* (Bp) prn1 gene, insertion sequence IS481 (GenBank Accession No. AB670737.1) | ATGAACATGTCTCTGTCACGCATTGTCAAGGCGGCGC<br>CCCTGCGCCGCACCACGCTGGCCATGGCGCTGGGCGC<br>GCTGGGCGCCGCCCCGGCGGCGCATGCCGACTGGAAC<br>AACCAGTCCATCGTCAAGACCGGTGAGCGCCAGCATG<br>GCATCCATATCCAGGGCTCCGACCCGGGCGGCGTACG<br>GACCGCCAGCGGAACCACCATCAAGGTAAGCGGCCGT<br>CAGGCCCAGGGCATCCTGCTAGAAAATCCCGCGGCCG<br>AGCTGCAGTTCCGGAACGGCAGTGTCACGTCGTCGGG<br>ACAGTTGTCCGACGATGGCATCCGGCGCTTTCTGGGC<br>ACCGTCACCGTCAAGGCCGGCAAGCTGGTCGCCGATC |

TABLE 28-continued

| SEQ ID NO | Description | Sequence (5′ → 3′) |
|---|---|---|
| | | ACGCCACGCTGGCCAACGTTGGCGACACCTGGGACGA<br>CGACGGCATCGCGCTCTATGTGGCCGGCGAACAGGCC<br>CAGGCCAGCATCGCCGACAGCACCCTGCAGGGCGCTG<br>GCGGCGTGCAGATCGAGCGCGGCGCCAATGTCACGGT<br>CCAACGCAGCGCCATCGTCGACGGGGGCTTGCATATC<br>GGCGCCCTGCAGTCATTGCAGCCGGAAGACCTTCCGC<br>CCAGCCGGGTGGTGCTGCGCGACACCAACGTGACCGC<br>CGTGCCCGCCAGCGGCGCGCCCGCGGCGGTGTCTGTG<br>TTGGGGGCCAGTGAGCTTACGCTCGACGGCGGGCACA<br>TCACCGGCGGGCGGGCAGCGGGGGTGGCGGCCATGCA<br>AGGGGCGGTCGTGCATCTGCAGCGCGCGACGATACGG<br>CGCGGGGACGCGCCTGCCGGCGGTGCGGTTCCCGGCG<br>GTGCGGTTCCCGGTGGTGCGGTTCCCGGCGGCTTCGG<br>TCCCGGCGGCTTCGGTCCCGTCCTCGACGGCTGGTAT<br>GGCGTGGACGTATCGGGCTCCAGCGTGGAGCTCGCCC<br>AGTCGATCGTCGAGGCGCCGGAGCTGGGCGCCGCAAT<br>CCGGGTGGGCCGCGGCGCCAGGGTGACGGTGTCGGGC<br>GGCAGCTTGTCCGCACCGCACGGCAATGTCATCGAGA<br>CCGGCGGCGCGCGTCGCTTTGCGCCTCAAGCCGCGCC<br>CCTGTCGATCACCTTGCAGGCCGGCGCGCATGCCCAG<br>GGGAAAGCGCTGCTGTACCGGGTCCTGCCGGAGCCCG<br>TGAAGCTGACGCTGACCGGGGGCGCCGATGCGCAGGG<br>CGACATCGTCGCGACGGAGCTGCCCTCCATTCCCGGC<br>ACGTCGATCGGGCCGCTCGACGTGGCGCTGGCCAGCC<br>AGGCCCGATGGACGGGCGCTACCCGCGCGGTCGACTC<br>GCTGTCCATCGACAACGCCACCTGGGTCATGACGGAC<br>AACTCGAACGTCGGTGCGCTACGGCTGGCCAGCGACG<br>GCAGCGTCGATTTCCAGCAGCCGGCCGAAGCTGGGCG<br>GTTCAAGGTCCTGACGGTCAATACGCTGGCGGGTTCG<br>GGGCTGTTCCGCATGAATGTCTTCGCGGACCTGGGGC<br>TGAGCGACAAGCTGGTCGTCATGCAGGACGCCAGCGG<br>CCAGCACAGGCTGTGGGTCCGCAACAGCGGCAGCGAG<br>CCGGCCAGCGCCAACACCCTGCTGCTGGTGCAGACGC<br>CACTAGGTGTGAAGATTCAATAGGTTGTATGCATGGT<br>TCATCCGAACCGGATTTGAGAAACTGGAAATCGCCAA<br>CCCCCCAGTTCACTCAAGGAGCCCGGCCGGATGAACA<br>CCCATAAGCATGCCCGATTGACCTTCCTACGTCGACT<br>CGAAATGGTCCAGCAATTGATCGCCCATCAAGTTTGT<br>GTGCCTGAAGCGGCCCGCGCCTATGGGGTCACCGCGC<br>CGACTGTGCGCAAATGGCTGGGCCGCTTCCTGGCTCA<br>GGGCCAGGCGGGCTTGGCCGATGCGTCCTCGCGCCCG<br>ACGGTCTCGCCCCGAGCGATTGCGCCGGCCAAGGCGC<br>TGGCTATCGTGGAGCTGCGCCGCAAGCGGCTGACCCA<br>AGCGCGCATCGCCCAGGCGCTGGGCGTGTCAGCCAGC<br>ACCGTCAGCCGCGTCCTGGCCCGCGCCGGTCTGTCGC<br>ACCTGGCCGACCTGGAGCCGGCCGAGCCGGTGGTGCG<br>CTACGAGCATCAGGCCCCCGGCGATCTGCTGCACATC<br>GACATCAAGAAGCTGGGACGTATCCAGCGCCCTGGTC<br>ACCGGGTCACGGGCAACCGACGCGATACCGTTGAGGG<br>GGCCGGCTGGGACTTCGTCTTCGTGGCCATCGATGAC<br>CACGCCCGCGTGGCCTTCACCGACATCCACCCCGACG<br>AGCGCTTCCCCAGCGCCGTCCAGTTCCTCAAGGACGC<br>AGTGGCCTACTACCAGCGCCTGGGCGTGACCATCCAG<br>CGCTTGCTCACCGACAATGGCTCGGCCTTTCGCAGCC<br>GCGCCTTCGCCGCGCTGTGCCATGAGCTGGGCATCAA<br>GCACCGCTTTACCCGACCTTACCGCCCACAGACCAAT<br>GGCAAGGCCGAACGCTTCATCCAGTCGGCCTTGCGTG<br>AGTGGGCTTACGCTCACACCTACCAGAACTCCCAACA<br>CCGAGCCGATGCCATGAAATCCTGGCTACACCACTAC<br>AACTGGCATCGACCCCACCAAGGCATCGGGCGCGCTG<br>TACCCATCTCCAGACTCAACCTGGACGAATACAACCT<br>ATTGACAGTTCACAACTAGGCAGCGCGGCGACCTTTA<br>CCCTTGCCAACAAGGACGGCAAGGTCGATATCGGTAC<br>CTATCGCTATCGATTGGCCGCCAACGGCAATGGGCAG<br>TGGAGCCTGGTGGGCGCGAAGGCGCCGCCGGCGCCCA<br>AGCCCGCGCCGCAGCCGGGTCCCCAGCCGCCGCAGCC<br>GCCGCAGCCGCAGCCGGAAGCGCCGGCGCCGCAACCG<br>CCGGCGGGCAGGGAGTIGTCCGCCGCCGCCAACGCGG<br>CGGTCAACACGGGTGGGGTGGGCCTGGCCAGCACGCT<br>CTGGTACGCCGAAAGCAATGCGTTGTCCAAGCGCCTG<br>GGCGAGTTGCGCCTGAATCCGGACGCCGGCGGCGCCT<br>GGGGCCGCGGCTTCGCGCAACGCCAGCAGCTGGACAA<br>CCGCGCCGGGCGGCGCTTCGACCAGAAGGTGGCCGGC<br>TTCGAGCTGGGCGCCGACCACGCGGTGGCGGTGGCCG<br>GCGGACGCTGGCACCTGGGCGGGCTGGCCGGCTATAC<br>GCGCGGCGACCGCGGCTTCACCGGCGACGGCGGCGGC |

TABLE 28-continued

| SEQ ID NO | Description | Sequence (5′ → 3′) |
|---|---|---|
| | | CACACCGACAGCGTGCATGTCGGGGGCTATGCCACAT ATATCGCCGACAGCGGTTTCTACCTGGACGCGACGCT GCGCGCCAGCCGCCTGGAGAATGACTTCAAGGTGGCG GGCAGCGACGGGTACGCGGTCAAGGGCAAGTACCGCA CCCATGGGGTGGGCGCCTCGCTCGAGGCGGGCCGGCG CTTTACCCATGCCGACGGCTGGTTCCTCGAGCCGCAG GCCGAGCTGGCGGTATTCCGGGCCGGCGGCGGTGCGT ACCGCGCGGCCAACGGCCTGCGGGTGCGCGACGAAGG CGGCAGCTCGGTGCTGGGTCGCCTGGGCCTGGAGGTC GGCAAGCGCATCGAACTGGCAGGCGGCAGGCAGGTGC AGCCATACATCAAGGCCAGCGTGCTGCAGGAGTTCGA CGGCGCGGGTACGGTACACACCAACGGCATCGCGCAC CGCACCGAACTGCGCGGCACGCGCGCCGAACTGGGCC TGGGCATGGCCGCCGCGCTGGGCCGCGGCCACAGCCT GTATGCCTCGTACGAGTACTCCAAGGGCCCGAAGCTG GCCATGCCGTGGACCTTCCACGCGGGCTACCGGTACA GCTGGTAAAGCGAGGAG |
| 2 | *Bordetella parapertussis* (Bpp) strain FR4640 insertion sequence IS1001 (GenBank Accession No. JX013522.1) | GCTGGATCGCAAGTTGCTGGAGTCGCTGGGAGGCTGG CAGGGCTATGGCGTCGAACGCGTGGAATGGCCCGAAG ACCCAGGGCGCACGCTGTCGATCTATTTGAAGCCAAC GGCCAAGGTGATGCTGTGCGAGCAGTGCGGCGCGCGG TGTCGCCAGGTGCATGAGACCACGGTTCGACGGGTGC GAGATCTGCCGTTATTCGAGTATCGGGTCGTTCTGCA CGTGCCGCGCCGACGCTTGTGGTGTGAGCAATGCGGC GGCCCGCGCCTGGAGCGGCTTGCCTGGCTGGGGCGAT ATCAACGGGTGACGGATCGGCTGGCGCAGGCCTGCAG CCAATTGCTGCAATCGAGCAACGTGCAGGCGGTGGCG AGGTTCTTCGAGCTGGGTTGGCATACCGTCAAGACGC TGGACAAGGCTCGGCTGCGTGCGTCGGTGCGCGAACC GGATTGGTCCAAGATCGAGTATTTGGCGATGGACGAG TTTGCCCTGCACAAAGGGCATCGCTACGCGACAGTGG TGGTCGATCCGATCGGCAGGCAGGTGCTGTGGATTGG CCCAGGACGCTCACGCGAGACGGCCCGGGCGTTCTTC GAACAATTGCCGCCTGGGGCCGCCCAACGCATCAAGG CCGTTGCCATCGACATGACCACCGCCTACGAGTTGGA GATCCAGGCCCACAGCCCACAGGCGGAGATCGTCTAT GACTTGTTCCATGTCGTGGCCAAGTATGGACGAGAGG TCATTGATCGGGTGCGCGTGGATCAGGCCAATCAACT ACGCCAGGATCGTCCCGCACGCAGGATCATCAAATCG AGTCGCTGGCTGCTGCTGCGCAACCGTGACAACCTGG ATCGGCAGCAGGCCGTCCGGCTCGACGAATTGCTGCA AGCCAACCAGCCGCTGCTGACGGTCTATGTCCTGCGT GACGAACTCAAACGGCTCTGGTTCTACCAAAGACCTG CCTGGGCAAGACAAGCCTGGAACCACTGGTACGAGCA GGCCGAGCAAAGCGGAATAGCCGCCTTGAACACCTTC GCTCAGCGCTTGAAAGGCTATCTGCACGGCATCCTGG CCAGATGCCGACATCCCCTGAACACCAGCATTGTCGA GGGCATCAACAACACTATCAAGGTCATCAAGCGGCGC GCTTACGGCTACCGCGACCAGGAATACTTCTTCCTCA AAATCC |
| 3 | Bp sense oligomer | TTGCGTGAGTGGGCTTA |
| 4 | Bp sense oligomer | AACACCGAGCCGATGCCATG |
| 5 | Bp antisense oligomer | ATGCCAGTTGTAGTGGTGTA |
| 6 | Bp sense oligomer | CCTTGCGTGAGTGGGCTTAC |
| 7 | Bp sense oligomer | CCCAACACCGAGCCGATGCC |
| 8 | Bp antisense oligomer | GTGGGGTCGATGCCAGTTGT |
| 9 | Bp sense oligomer | TTACGCTCACACCTACCA |
| 10 | Bp sense oligomer | TACACCACTACAACTGGCATCGAC |
| 11 | Bp antisense oligomer | AGTCTGGAGATGGGTACAG |
| 12 | Bp sense oligomer | CCGATGCCATGAAATCCT |
| 13 | Bp sense oligomer | TACACCACTACAACTGGCATCGAC |

TABLE 28-continued

| SEQ ID NO | Description | Sequence (5′ → 3′) |
|---|---|---|
| 14 | Bp antisense oligomer | GTATTCGTCCAGGTTGAGTC |
| 15 | Bp sense oligomer | CACATATATCGCCGACAGC |
| 16 | Bp sense oligomer | TTTCTACCTGGACGCGACGC |
| 17 | Bp antisense oligomer | CGCCACCTTGAAGTCATT |
| 18 | Bp sense oligomer | CCGAACCGGATTTGAGAAAC |
| 19 | Bp sense oligomer | CCGGCCGGATGAACACCCATAA |
| 20 | Bp antisense oligomer | TAGGAAGGTCAATCGGGCAT |
| 21 | Bp sense oligomer | GATTCAATAGGTTGTATGCATGGTT |
| 22 | Bp sense oligomer | TCGCCAACCCCCCAGTTCACTCA |
| 23 | Bp antisense oligomer | TTCAGGCACACAAACTTGATGGGCG |
| 24 | Bp antisense oligomer | ATCGGGCATGCTTATGGGTGTTCA |
| 25 | Bp antisense oligomer | CTTGAGTGAACTGGGGGGTCGGCGATTTCCAGTT |
| 26 | Bp sense oligomer | GCGGGCTAACTGTGAAGATTCAATAG |
| 27 | Bp sense oligomer | GATTCAATAGGTTGTATGCATGG |
| 28 | Bp sense oligomer | ATAAGCATGCCCGATTGACCTTCC |
| 29 | Bp antisense oligomer | TTCAGGCACACAAACTTGATGG |
| 30 | Bpp sense oligomer | GAGATCGTCTATGACTTGTTCC |
| 31 | Bpp antisense oligomer | AATGACCTCTCGTCCATACTTGGC |
| 32 | Bpp antisense oligomer | ACGATCCTGGCGTAGTT |
| 33 | Bpp sense oligomer | TTCGAGTATCGGGTCGTT |
| 34 | Bpp sense oligomer | CTTGTGGTGTGAGCAATGCGG |
| 35 | Bpp antisense oligomer | ATCCGTCACCCGTTGATA |
| 36 | Bpp sense oligomer | CACCGCCTACGAGTTCGAGAT |
| 37 | Bpp sense oligomer | GTTCTACCAAAGACCTGCCTGGGC |
| 38 | Bpp antisense oligomer | CCTCGACAATGCTGGTGTTCA |
| 39 | Bpp sense oligomer | CCATGTCGTGGCCAAGTATG |
| 40 | Bpp sense oligomer | ACGCAGGATCATCAAATCGAGTCG |
| 41 | Bpp antisense oligomer | GCTGGTTGGCTTGCAGCAAT |
| 42 | Bpp sense oligomer | TCAAGACGCTGGACAAGGCT |
| 43 | Bpp sense oligomer | CGGCTGCGTGCGTCGGTG |
| 44 | Bpp antisense oligomer | GCAGGGCAAACTCGTCCATC |

TABLE 28-continued

| SEQ ID NO | Description | Sequence (5′ → 3′) |
|---|---|---|
| 45 | Bp sense oligomer | CTTACGCTCACACCTACCA |
| 46 | Bp antisense oligomer | CGATGCCAGTTGTAGTGGT |

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes. To the extent that any material incorporated by reference is inconsistent with the express content of this disclosure, the express content controls.

What is claimed is:

1. A composition for determining the presence or absence of each of *Bordetella pertussis* (Bp) and *Bordetella parapertussis* (Bpp) in a sample, said composition comprising:

a first amplification oligomer combination and a second amplification oligomer combination, wherein (I) the first amplification oligomer combination comprises first and second Bp-specific amplification oligomers capable of amplifying a target region of a Bp target nucleic acid, wherein the first and second Bp-specific amplification oligomers comprise, respectively, a first Bp-specific target-hybridizing sequence and a second Bp-specific target-hybridizing sequence, wherein (a) the first Bp-specific target hybridizing sequence is SEQ ID NO:9, SEQ ID NO: 12, SEQ ID NO:45, a sequence having at least 85% identity with SEQ ID NO: 3, a sequence having at least 85% identity with SEQ ID NO:6, or an RNA equivalent or DNA/RNA chimeric thereof, and the second Bp-specific target-hybridizing sequence is SEQ ID NO:5, SEQ ID NO: 8, or SEQ ID NO:11, or an RNA equivalent or DNA/RNA chimeric thereof; or (b) the first Bp-specific target-hybridizing sequence is SEQ ID NO:18, SEQ ID NO: 21, or SEQ ID NO:27, or an RNA equivalent or DNA/RNA chimeric thereof, and the second Bp-specific target-hybridizing sequence is SEQ ID NO:20 or SEQ ID NO:23, or an RNA equivalent or DNA/RNA chimeric thereof;

and (II) the second amplification oligomer combination comprises first and second Bpp-specific amplification oligomers capable of amplifying a target region of a Bpp target nucleic acid, wherein the first and second Bpp-specific amplification oligomers comprise, respectively, first and second Bpp-specific target-hybridizing sequences, wherein (a) the first Bpp-specific target-hybridizing sequence is SEQ ID NO:30, SEQ ID NO: 36, or SEQ ID NO:39, or an RNA equivalent or DNA/RNA chimeric thereof, and the second Bpp-specific target-hybridizing sequence is SEQ ID NO:32, SEQ ID NO: 38, or SEQ ID NO:41, or an RNA equivalent or DNA/RNA chimeric thereof;

(b) the first Bpp-specific target-hybridizing sequence is SEQ ID NO:33, or an RNA equivalent or DNA/RNA chimeric thereof, and the second Bpp-specific target-hybridizing sequence is SEQ ID NO:35, or an RNA equivalent or DNA/RNA chimeric thereof; or (c) the first Bpp-specific target-hybridizing sequence is SEQ ID NO:42, or an RNA equivalent or DNA/RNA chimeric thereof, and the second Bpp-specific target-hybridizing sequence is SEQ ID NO:44, or an RNA equivalent or DNA/RNA chimeric thereof; and at least one detection probe oligomer configured to specifically hybridize to a Bp or Bpp target sequence that is amplifiable using the first and second Bp-specific amplification oligomers or the first and second Bpp-specific amplification oligomers, wherein the at least one detection probe oligomer comprises a fluorescent or chemiluminescent label.

2. The composition of claim 1, wherein the first and second Bp-specific target-hybridizing sequences are, respectively, selected from the group consisting of (i) SEQ ID NO:3, or an RNA equivalent or DNA/RNA chimeric thereof, and SEQ ID NO:5, or an RNA equivalent or DNA/RNA chimeric thereof;

(ii) SEQ ID NO:6, or an RNA equivalent or DNA/RNA chimeric thereof, and SEQ ID NO:8, or an RNA equivalent or DNA/RNA chimeric thereof;

(iii) SEQ ID NO:9, or an RNA equivalent or DNA/RNA chimeric thereof, and SEQ ID NO:11, or an RNA equivalent or DNA/RNA chimeric thereof;

(iv) SEQ ID NO:18, or an RNA equivalent or DNA/RNA chimeric thereof, and SEQ ID NO:20, or an RNA equivalent or DNA/RNA chimeric thereof; and (v) SEQ ID NO:21, or an RNA equivalent or DNA/RNA chimeric thereof, and SEQ ID NO:23, or an RNA equivalent or DNA/RNA chimeric thereof.

3. The composition of claim 2, wherein the at least one detection probe oligomer comprises a Bp-specific detection probe oligomer comprising a Bp-specific detection probe target-hybridizing sequence that is from about 15 to about 35 nucleotides in length and is configured to hybridize to a target sequence contained within a Bp amplicon amplifiable by the first and second Bp-specific amplification oligomers; optionally wherein the first and second Bp-specific target-hybridizing sequences are target-hybridizing sequences of (i) and the Bp-specific detection probe target-hybridizing sequence is a sequence having at least 85% identity with SEQ ID NO:4, or an RNA equivalent or DNA/RNA chimeric thereof;

the first and second Bp-specific target-hybridizing sequences are target-hybridizing sequences of (ii) and the Bp-specific detection probe target-hybridizing sequence is a sequence having at least 85% identity with SEQ ID NO:7, or an RNA equivalent or DNA/RNA chimeric thereof;

the first and second Bp-specific target-hybridizing sequences are target-hybridizing sequences of (iii) and the Bp-specific detection probe target-hybridizing sequence is SEQ ID NO:10, or an RNA equivalent or DNA/RNA chimeric thereof;

the first and second Bp-specific target-hybridizing sequences are target-hybridizing sequences of (iv) and the Bp-specific detection probe target-hybridizing sequence is SEQ ID NO: 16, or an RNA equivalent or DNA/RNA chimeric thereof; or the first and second Bp-specific target-hybridizing sequences are target-hybridizing sequences of (v) and the Bp-specific detection probe target-hybridizing sequence is SEQ ID NO: 19, or an RNA equivalent or DNA/RNA chimeric thereof.

4. The composition of claim 1, wherein the first and second Bpp-specific target-hybridizing sequences are, respectively, selected from the group consisting of (i') SEQ ID NO:30, or an RNA equivalent or DNA/RNA chimeric thereof, and SEQ ID NO:32, or an RNA equivalent or DNA/RNA chimeric thereof;

(ii') SEQ ID NO:33, or an RNA equivalent or DNA/RNA chimeric thereof, and SEQ ID NO:35, or an RNA equivalent or DNA/RNA chimeric thereof;

(iii') SEQ ID NO:36, or an RNA equivalent or DNA/RNA chimeric thereof, and SEQ ID NO:38, or an RNA equivalent or DNA/RNA chimeric thereof;

(iv') SEQ ID NO:39, or an RNA equivalent or DNA/RNA chimeric thereof, and SEQ ID NO:41, or an RNA equivalent or DNA/RNA chimeric thereof; and (v') SEQ ID NO:42, or an RNA equivalent or DNA/RNA chimeric thereof, and SEQ ID NO:44, or an RNA equivalent or DNA/RNA chimeric thereof.

5. The composition of claim 4, wherein the at least one detection probe oligomer comprises a Bpp-specific detection probe oligomer comprising a Bpp-specific detection probe target-hybridizing sequence that is from about 15 to about 35 nucleotides in length and is configured to hybridize to a target sequence contained within a Bpp amplicon amplifiable by the first and second Bpp-specific amplification oligomers; optionally wherein the first and second Bpp-specific target-hybridizing sequences are target-hybridizing sequences of (i') and the Bpp-specific detection probe target-hybridizing sequence is SEQ ID NO:31, or an RNA equivalent or DNA/RNA chimeric thereof;

the first and second Bpp-specific target-hybridizing sequences are target-hybridizing sequences of (ii') and the Bpp-specific detection probe target-hybridizing sequence is SEQ ID NO:34, or an RNA equivalent or DNA/RNA chimeric thereof;

the first and second Bpp-specific target-hybridizing sequences are target-hybridizing sequences of (iii') and the Bpp-specific detection probe target-hybridizing sequence is SEQ ID NO:37, or an RNA equivalent or DNA/RNA chimeric thereof;

the first and second Bpp-specific target-hybridizing sequences are target-hybridizing sequences of (iv') and the Bpp-specific detection probe target-hybridizing sequence is SEQ ID NO:40, or an RNA equivalent or DNA/RNA chimeric thereof; or the first and second Bpp-specific target-hybridizing sequences are target-hybridizing sequences of (v') and the Bpp-specific detection probe target-hybridizing sequence is SEQ ID NO:43, or an RNA equivalent or DNA/RNA chimeric thereof.

6. A kit for determining the presence or absence of each of *Bordetella pertussis* (Bp) and *Bordetella parapertussis* (Bpp) in a sample, said kit comprising the composition of claim 1.

7. A method for determining the presence or absence of each of *Bordetella pertussis* (Bp) and *Bordetella parapertussis* (Bpp) in a sample, said method comprising:

(1) contacting a sample suspected of containing at least one of *Bordetella pertussis* (Bp) and *Bordetella parapertussis* (Bpp) with the first amplification oligomer combination and the second amplification oligomer combination according to claim 1;

(2) performing an in vitro nucleic acid amplification reaction, wherein any Bp target nucleic acid, if present in the sample, is used as a template for generating one or more amplicons corresponding to the Bp target region, and wherein any Bpp target nucleic acid, if present in the sample, is used as a template for generating one or more amplicons corresponding to the Bpp target region; and (3) detecting the presence or absence of the one or more amplicons, thereby determining the presence or absence of Bp and Bpp in the sample.

8. The composition of claim 1, wherein the first Bp-specific target-hybridizing sequence having at least 85% identity with SEQ ID NO:3 is SEQ ID NO:3 or SEQ ID NO:6, or an RNA equivalent or DNA/RNA chimeric thereof.

9. The composition of claim 3, wherein the Bp-specific detection probe target-hybridizing sequence having at least 85% identity with SEQ ID NO:4 is SEQ ID NO:4 or SEQ ID NO:7, or an RNA equivalent or DNA/RNA chimeric thereof.

10. The method of claim 7, wherein the first Bp-specific target-hybridizing sequence having at least 85% identity with SEQ ID NO:3 is SEQ ID NO:3 or SEQ ID NO:6, or an RNA equivalent or DNA/RNA chimeric thereof.

11. The composition of claim 1, wherein the first and second Bp-specific amplification oligomers comprise the first and second Bp-specific target-hybridizing sequences of (I)(a).

12. The composition of claim 11, wherein the first Bp-specific target-hybridizing sequence is the sequence having at least 85% identity with SEQ ID NO:3, a sequence having at least 85% identity with SEQ ID NO:6, or an RNA equivalent or DNA/RNA chimeric thereof.

13. The composition of claim 12, wherein the second Bp-specific target-hybridizing sequence is SEQ ID NO:5 or SEQ ID NO:8, or an RNA equivalent or DNA/RNA chimeric thereof.

14. The composition of claim 13, wherein the at least one detection probe oligomer comprises a Bp-specific detection probe oligomer comprising a Bp-specific detection probe target-hybridizing sequence that is a sequence having at least 85% identity with SEQ ID NO: 4, a sequence having at least 85% identity with SEQ ID NO:7, or an RNA equivalent or DNA/RNA chimeric thereof.

15. The composition of claim 1, wherein the first and second Bpp-specific amplification oligomers comprise the first and second Bpp-specific target-hybridizing sequences of (II)(a).

16. The composition of claim 15, wherein the first Bpp-specific target-hybridizing sequence is SEQ ID NO:30, or an RNA equivalent or DNA/RNA chimeric thereof.

17. The composition of claim 16, wherein the second Bpp-specific target-hybridizing sequence is SEQ ID NO:32, or an RNA equivalent or DNA/RNA chimeric thereof.

18. The composition of claim 17, wherein the at least one detection probe oligomer comprises a Bpp-specific detection probe oligomer comprising a Bpp-specific detection probe target-hybridizing sequence that is SEQ ID NO:31, or an RNA equivalent or DNA/RNA chimeric thereof.

19. The composition of claim 13, wherein the first Bpp-specific target-hybridizing sequence is SEQ ID NO:30, or an RNA equivalent or DNA/RNA chimeric thereof.

20. The composition of claim 19, wherein the second Bpp-specific target-hybridizing sequence is SEQ ID NO:32, or an RNA equivalent or DNA/RNA chimeric thereof.

* * * * *